(12) United States Patent
Hsueh et al.

(10) Patent No.: US 12,059,433 B2
(45) Date of Patent: Aug. 13, 2024

(54) TREATMENT FOR AUTISTIC SPECTRUM DISORDER (ASD) AND RELEVANT SYMPTOMS

(71) Applicant: ACADEMIA SINICA, Taipei (TW)

(72) Inventors: Yi-Ping Hsueh, Taipei (TW); Tzyy-Nan Huang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 638 days.

(21) Appl. No.: 17/077,504

(22) Filed: Oct. 22, 2020

(65) Prior Publication Data

US 2021/0113610 A1 Apr. 22, 2021

Related U.S. Application Data

(60) Provisional application No. 62/924,269, filed on Oct. 22, 2019.

(51) Int. Cl.
| | | |
|---|---|---|
| *A61K 31/198* | (2006.01) | |
| *A01K 67/0276* | (2024.01) | |
| *A01K 67/0278* | (2024.01) | |
| *A23K 20/142* | (2016.01) | |
| *A23K 20/20* | (2016.01) | |
| *A23L 33/16* | (2016.01) | |
| *A23L 33/175* | (2016.01) | |
| *A61K 9/00* | (2006.01) | |
| *A61K 9/68* | (2006.01) | |
| *A61K 33/30* | (2006.01) | |
| *A61K 49/00* | (2006.01) | |
| *A61P 25/00* | (2006.01) | |
| *G01N 33/68* | (2006.01) | |

(52) U.S. Cl.
CPC .......... *A61K 33/30* (2013.01); *A01K 67/0276* (2013.01); *A01K 67/0278* (2013.01); *A23K 20/142* (2016.05); *A23K 20/30* (2016.05); *A23L 33/16* (2016.08); *A23L 33/175* (2016.08); *A61K 9/0056* (2013.01); *A61K 9/0058* (2013.01); *A61K 9/0095* (2013.01); *A61K 31/198* (2013.01); *A61K 49/0008* (2013.01); *A61P 25/00* (2018.01); *G01N 33/6806* (2013.01); *A01K 2217/072* (2013.01); *A01K 2217/075* (2013.01); *A01K 2227/105* (2013.01); *A01K 2267/0306* (2013.01); *A23V 2002/00* (2013.01)

(58) Field of Classification Search
CPC .............................. A61K 31/198; A61K 9/053
See application file for complete search history.

(56) References Cited

PUBLICATIONS

Meguid et al (The role of zinc supplementation on the metallothionein system in children with autism spectrum disorder; Acta Neurologica Belgica, 119:577-583, 2019) (Year: 2019).*
Hu et al (The Involvement of Neuron-Specific Factors in Dendritic Spinogenesis: Molecular Regulation and Association with Neurological Disorders, Neural Plasticity, vol. 2016) (Year: 2016).*
Dufour et al (Modulation of absence seizures by branched-chain amino acids: correlation with brain amino acid concentrations, Neuroscience Research 40, 2001, 255-263) (Year: 2001).*
Jacome et al (D-serine improves dimensions of the sociability deficit of the genetically-inbred Balb/c mouse strain, Brain Research Bulletin 84, 2011, 12-16) (Year: 2011).*

* cited by examiner

*Primary Examiner* — Micah Paul Young
(74) *Attorney, Agent, or Firm* — Birch, Stewart, Kolasch & Birch, LLP

(57) ABSTRACT

The present invention relates to a method for treating autism spectrum disorders (ASD) or ASD-like symptom, particularly by administering a zinc ion source and/or a serine component e.g. D-serine or its precursor/analogue, optionally in combination with a mixture of branched-chain amino acids (BCAAs). The present invention also relates to a combination, kit or composition for performing the method for treatment as described herein. Further described is use of a zinc ion source and/or a serine component and optional BCAAs for manufacturing a medicament for treating a symptom or disease characteristics associated with ASD or ASD-associated disorder or as a food supplement for ameliorating relevant symptoms in a subject in need thereof. The present invention further provides an animal model for autistic spectrum disorder (ASD) with deficient CTTNBP2 gene, and a method for identifying an ingredient effective in the treatment of ASD by using such animal model.

21 Claims, 36 Drawing Sheets
Specification includes a Sequence Listing.

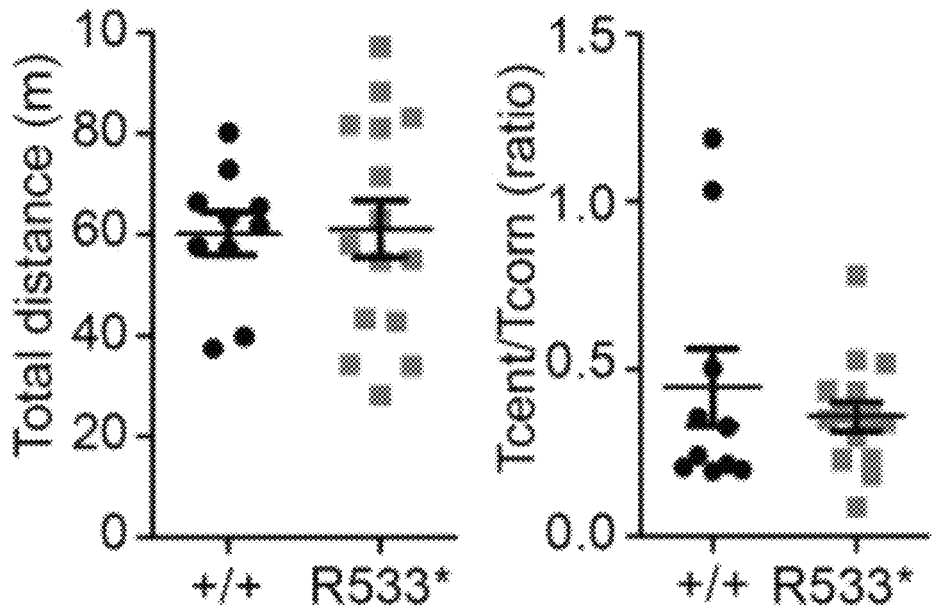
Fig. 3F
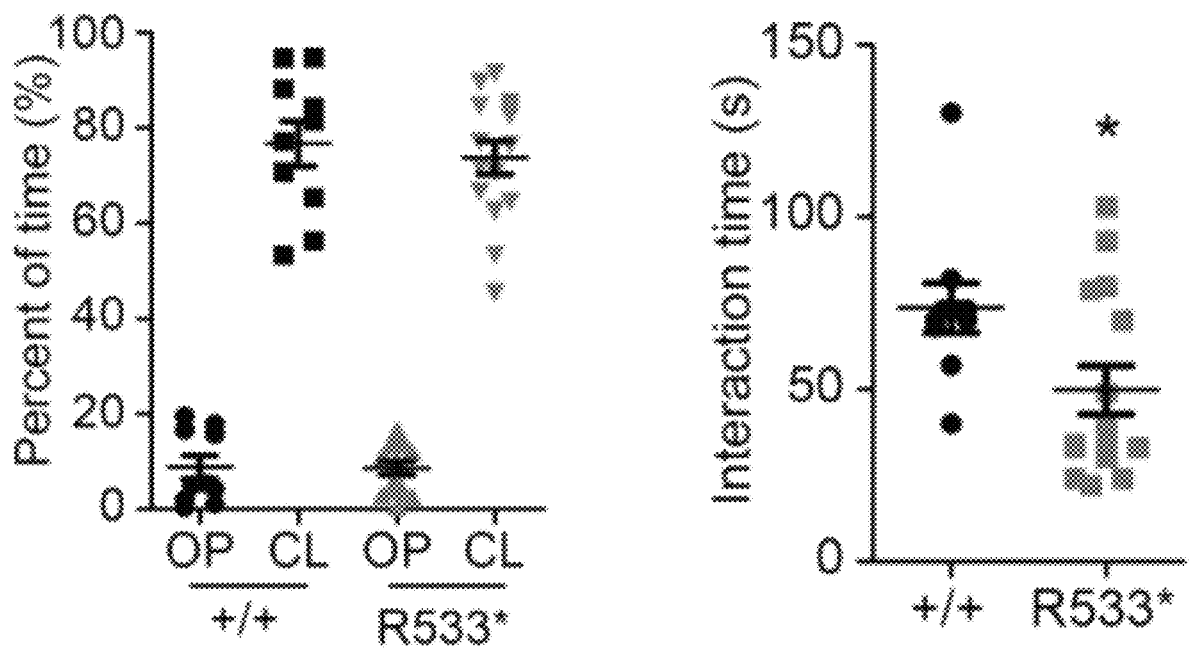
Fig. 3G
Fig. 3H

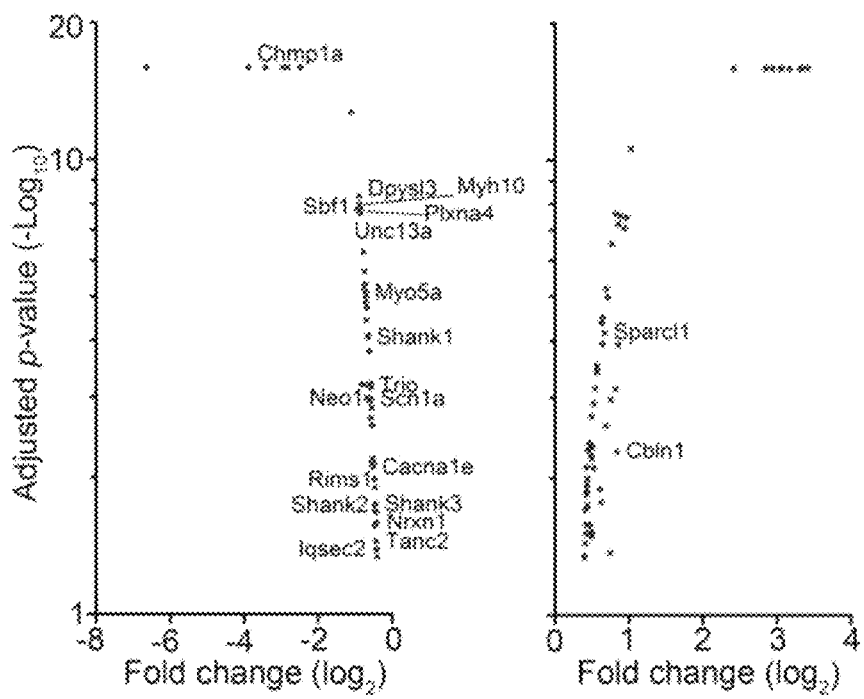

Fig. 6D

| Gene | SFARI/SPARK | Molecular function |
|---|---|---|
| Shank3*# | 1.1/SPARK | PSD scaffold |
| Trio | 2.1/SPARK | GTP exchange factor, actin regulator |
| Shank2*# | 2.1/SPARK | PSD scaffold |
| Nrxn1 | 2.1/SPARK | Synaptic adhesion molecule |
| Chmp1a | 3.1 | ESCRT III complex, vesicle trafficing |
| Cacna1e | 3.1 | Voltage-sensitive calcium channel subunit |
| Sparcl1 | 3.1 | Secreted protein regulating synapse formation |
| Scn1a | 3.1/SPARK | Ion channel |
| Rims1 | 3.1/SPARK | Synaptic vesicle tethering |
| Tanc2 | 3.1 | Scaffold protein with unknown function |
| Shank1 | 3.1 | PSD scaffold |
| Plxna4 | 3.1 | Semaphorin-plexin signaling pathway |
| Myo5a | 3.1 | Actin-based motor protein |
| Sbf1 | 3.1 | A member of protein tyrosine phosphatase family |
| Myh10 | 3.1 | Non-muscle myosin |
| Neo1 | 4.1 | Cell-adheision and axon guidance |
| Dpysl3* | 4.1S | CRMP4, downstream of Plexin |
| Unc13a | 4.1S | Synaptic vesicle recycling |
| Iqsec2 | 4.1S/SPARK | Endocytosis and protein scaffolding |
| Cbln1 | 5.1S | Synapse formation |
| Kras | SPARK | Signaling downstream of NMDAR |

Notes: S, Syndromic; *, immunoblotting validated; #, IP validated

Fig. 6E

SEQUENCE LISTING

```
<160> NUMBER OF SEQ ID NOS: 11

<210> SEQ ID NO 1
<211> LENGTH: 1663
<212> TYPE: PRT
<213> ORGANISM: Homo sapiens

<400> SEQUENCE: 1

Met Ala Thr Asp Gly Ala Ser Cys Glu Pro Asp Leu Ser Arg Ala Pro
1               5                   10                  15

Glu Asp Ala Ala Gly Ala Ala Ala Glu Ala Ala Lys Lys Glu Phe Asp
            20                  25                  30

Val Asp Thr Leu Ser Lys Ser Glu Leu Arg Met Leu Leu Ser Val Met
        35                  40                  45

Glu Gly Glu Leu Glu Ala Arg Asp Leu Val Ile Glu Ala Leu Arg Ala
    50                  55                  60

Arg Arg Lys Glu Val Phe Ile Gln Glu Arg Tyr Gly Arg Phe Asn Leu
65                  70                  75                  80

Asn Asp Pro Phe Leu Ala Leu Gln Arg Asp Tyr Glu Ala Gly Ala Gly
                85                  90                  95

Asp Lys Glu Lys Lys Pro Val Cys Thr Asn Pro Leu Ser Ile Leu Glu
            100                 105                 110

Ala Val Met Ala His Cys Lys Lys Met Gln Glu Arg Met Ser Ala Gln
        115                 120                 125

Leu Ala Ala Ala Glu Ser Arg Gln Lys Lys Leu Glu Met Glu Lys Leu
    130                 135                 140

Gln Leu Gln Ala Leu Glu Gln Glu His Lys Lys Leu Ala Ala Arg Leu
145                 150                 155                 160

Glu Glu Glu Arg Gly Lys Asn Lys Gln Val Val Leu Met Leu Val Lys
                165                 170                 175
```

```
Glu Cys Lys Gln Leu Ser Gly Lys Val Ile Glu Ala Gln Lys Leu
            180                 185                 190
Glu Asp Val Met Ala Lys Leu Glu Glu Lys Lys Thr Asn Glu
        195                 200                 205
Leu Glu Glu Glu Leu Ser Ala Glu Lys Arg Ser Thr Glu Met Glu
        210                 215                 220
Ala Gln Met Glu Lys Gln Leu Ser Glu Phe Asp Thr Glu Arg Glu Gln
225                 230                 235                 240
Leu Arg Ala Lys Leu Asn Arg Glu Glu Ala His Thr Thr Asp Leu Lys
                245                 250                 255
Glu Glu Ile Asp Lys Met Arg Lys Met Ile Glu Gln Leu Lys Arg Gly
            260                 265                 270
Ser Asp Ser Lys Pro Ser Leu Ser Leu Pro Arg Lys Thr Lys Asp Arg
            275                 280                 285
Arg Leu Val Ser Ile Ser Val Gly Thr Glu Gly Thr Val Thr Arg Ser
        290                 295                 300
Val Ala Cys Gln Thr Asp Leu Val Thr Glu Asn Ala Asp His Met Lys
305                 310                 315                 320
Lys Leu Pro Leu Thr Met Pro Val Lys Pro Ser Thr Gly Ser Pro Leu
                325                 330                 335
Val Ser Ala Asn Ala Lys Gly Ser Val Cys Thr Ser Ala Thr Met Ala
            340                 345                 350
Arg Pro Gly Ile Asp Arg Gln Ala Ser Tyr Gly Asp Leu Ile Gly Ala
        355                 360                 365
Ser Val Pro Ala Phe Pro Pro Ser Ala Asn Lys Ile Glu Glu Asn
370                 375                 380
Gly Pro Ser Thr Gly Ser Thr Pro Asp Pro Thr Ser Thr Pro Pro
385                 390                 395                 400
Leu Pro Ser Asn Ala Ala Pro Pro Thr Ala Gln Thr Pro Gly Ile Ala
                405                 410                 415
Pro Gln Asn Ser Gln Ala Pro Pro Met His Ser Leu His Ser Pro Cys
            420                 425                 430
Ala Asn Thr Ser Leu His Pro Gly Leu Asn Pro Arg Ile Gln Ala Ala
            435                 440                 445
Arg Phe Arg Phe Gln Gly Asn Ala Asn Asp Pro Asp Gln Asn Gly Asn
        450                 455                 460
Thr Thr Gln Ser Pro Pro Ser Arg Asp Val Ser Pro Thr Ser Arg Asp
465                 470                 475                 480
Asn Leu Val Ala Lys Gln Leu Ala Arg Asn Thr Val Thr Gln Ala Leu
                485                 490                 495
Ser Arg Phe Thr Ser Pro Gln Ala Gly Ala Pro Ser Arg Pro Gly Val
            500                 505                 510
Pro Pro Thr Gly Asp Val Gly Thr His Pro Pro Val Gly Arg Thr Ser
            515                 520                 525
Leu Lys Thr His Gly Val Ala Arg Val Asp Arg Gly Asn Pro Pro
        530                 535                 540
Ile Pro Pro Lys Lys Pro Gly Leu Ser Gln Thr Pro Ser Pro His
545                 550                 555                 560
Pro Gln Leu Lys Val Ile Ile Asp Ser Ser Arg Ala Ser Asn Thr Gly
                565                 570                 575
Ala Lys Val Asp Asn Lys Thr Val Ala Ser Thr Pro Ser Ser Leu Pro
            580                 585                 590
Gln Gly Asn Arg Val Ile Asn Glu Glu Asn Leu Pro Lys Ser Ser Ser
```

```
                595                 600                 605
Pro Gln Leu Pro Pro Lys Pro Ser Ile Asp Leu Thr Val Ala Pro Ala
610                 615                 620

Gly Cys Ala Val Ser Ala Leu Ala Thr Ser Gln Val Gly Ala Trp Pro
625                 630                 635                 640

Ala Ala Thr Pro Gly Leu Asn Gln Pro Ala Cys Ser Asp Ser Ser Leu
                645                 650                 655

Val Ile Pro Thr Thr Ile Ala Phe Cys Ser Ser Ile Asn Pro Val Ser
                660                 665                 670

Ala Ser Ser Cys Arg Pro Gly Ala Ser Asp Ser Leu Leu Val Thr Ala
                675                 680                 685

Ser Gly Trp Ser Pro Ser Leu Thr Pro Leu Leu Met Ser Gly Gly Pro
690                 695                 700

Ala Pro Leu Ala Gly Arg Pro Thr Leu Leu Gln Gln Ala Ala Ala Gln
705                 710                 715                 720

Gly Asn Val Thr Leu Leu Ser Met Leu Leu Asn Glu Glu Gly Leu Asp
                725                 730                 735

Ile Asn Tyr Ser Cys Glu Asp Gly His Ser Ala Leu Tyr Ser Ala Ala
                740                 745                 750

Lys Asn Gly His Thr Asp Cys Val Arg Leu Leu Leu Ser Ala Glu Ala
                755                 760                 765

Gln Val Asn Ala Ala Asp Lys Asn Gly Phe Thr Pro Leu Cys Ala Ala
770                 775                 780

Ala Ala Gln Gly His Phe Glu Cys Val Glu Leu Leu Ile Ser Tyr Asp
785                 790                 795                 800

Ala Asn Ile Asn His Ala Ala Asp Gly Gly Gln Thr Pro Leu Tyr Leu
                805                 810                 815

Ala Cys Lys Asn Gly Asn Lys Glu Cys Ile Lys Leu Leu Leu Glu Ala
                820                 825                 830

Gly Thr Asn Arg Ser Val Lys Thr Thr Asp Gly Trp Thr Pro Val His
                835                 840                 845

Ala Ala Val Asp Thr Gly Asn Val Asp Ser Leu Lys Leu Leu Met Tyr
850                 855                 860

His Arg Ile Pro Ala His Gly Asn Ser Phe Asn Glu Glu Ser Glu
865                 870                 875                 880

Ser Ser Val Phe Asp Leu Asp Gly Gly Glu Ser Pro Glu Gly Ile
                885                 890                 895

Ser Lys Pro Val Val Pro Ala Asp Leu Ile Asn His Ala Asn Arg Glu
                900                 905                 910

Gly Trp Thr Ala Ala His Ile Ala Ala Ser Lys Gly Phe Lys Asn Cys
                915                 920                 925

Leu Glu Ile Leu Cys Arg His Gly Gly Leu Glu Pro Glu Arg Arg Asp
930                 935                 940

Lys Cys Asn Arg Thr Val His Asp Val Ala Thr Asp Asp Cys Lys His
945                 950                 955                 960

Leu Leu Glu Asn Leu Asn Ala Leu Lys Ile Pro Leu Arg Ile Ser Val
                965                 970                 975

Gly Glu Ile Glu Pro Ser Asn Tyr Gly Ser Asp Leu Glu Cys Glu
                980                 985                 990

Asn Thr Ile Cys Ala Leu Asn Ile Arg Lys Gln Thr Ser Trp Asp Asp
                995                1000                1005

Phe Ser Lys Ala Val Ser Gln Ala Leu Thr Asn His Phe Gln Ala
    1010                1015                1020
```

```
Ile Ser Ser Asp Gly Trp Trp Ser Leu Glu Asp Val Thr Cys Asn
1025                1030                1035

Asn Thr Thr Asp Ser Asn Ile Gly Leu Ser Ala Arg Ser Ile Arg
1040                1045                1050

Ser Ile Thr Leu Gly Asn Val Pro Trp Ser Val Gly Gln Ser Phe
1055                1060                1065

Ala Gln Ser Pro Trp Asp Phe Met Arg Lys Asn Lys Ala Glu His
1070                1075                1080

Ile Thr Val Leu Leu Ser Gly Pro Gln Glu Gly Cys Leu Ser Ser
1085                1090                1095

Val Thr Tyr Ala Ser Met Ile Pro Leu Gln Met Met Gln Asn Tyr
1100                1105                1110

Leu Arg Leu Val Glu Gln Tyr His Asn Val Ile Phe His Gly Pro
1115                1120                1125

Glu Gly Ser Leu Gln Asp Tyr Ile Val His Gln Leu Ala Leu Cys
1130                1135                1140

Leu Lys His Arg Gln Met Ala Ala Gly Phe Ser Cys Glu Ile Val
1145                1150                1155

Arg Ala Glu Val Asp Ala Gly Phe Ser Lys Glu Gln Leu Leu Asp
1160                1165                1170

Leu Phe Ile Ser Ser Ala Cys Leu Ile Pro Val Lys Gln Ser Pro
1175                1180                1185

Ser Lys Lys Lys Ile Ile Ile Leu Glu Asn Leu Glu Lys Ser
1190                1195                1200

Ser Leu Ser Glu Leu Leu Arg Asp Phe Leu Ala Pro Leu Glu Asn
1205                1210                1215

Arg Ser Thr Glu Ser Pro Cys Thr Phe Gln Lys Gly Asn Gly Leu
1220                1225                1230

Ser Glu Cys Tyr Tyr Phe His Glu Asn Cys Phe Leu Met Gly Thr
1235                1240                1245

Ile Ala Lys Ala Cys Leu Gln Gly Ser Asp Leu Leu Val Gln Gln
1250                1255                1260

His Phe Arg Trp Val Gln Leu Arg Trp Asp Gly Glu Pro Met Gln
1265                1270                1275

Gly Leu Leu Gln Arg Phe Leu Arg Arg Lys Val Val Asn Lys Phe
1280                1285                1290

Lys Gly Gln Ala Pro Ser Pro Cys Asp Pro Val Cys Lys Ile Val
1295                1300                1305

Asp Trp Ala Leu Ser Val Trp Arg Gln Leu Asn Ser Cys Leu Ala
1310                1315                1320

Arg Leu Gly Thr Pro Glu Ala Leu Leu Gly Pro Lys Tyr Phe Leu
1325                1330                1335

Ser Cys Pro Val Val Pro Gly His Ala Gln Val Thr Val Lys Trp
1340                1345                1350

Met Ser Lys Leu Trp Asn Gly Val Ile Ala Pro Arg Val Gln Glu
1355                1360                1365

Ala Ile Leu Ser Arg Ala Ser Val Lys Arg Gln Pro Gly Phe Gly
1370                1375                1380

Gln Thr Thr Ala Lys Arg His Pro Ser Gln Gly Gln Gln Ala Val
1385                1390                1395

Val Lys Ala Ala Leu Ser Ile Leu Leu Asn Lys Ala Val Leu His
1400                1405                1410
```

```
Gly Cys Pro Leu Pro Arg Ala Glu Leu Asp Gln His Thr Ala Asp
    1415                1420                1425

Phe Lys Gly Gly Ser Phe Pro Leu Ser Ile Val Ser Ser Tyr Asn
    1430                1435                1440

Thr Cys Asn Lys Lys Gly Glu Ser Gly Ala Trp Arg Lys Val
    1445                1450                1455

Asn Thr Ser Pro Arg Arg Lys Ser Gly Arg Phe Ser Leu Pro Thr
    1460                1465                1470

Trp Asn Lys Pro Asp Leu Ser Thr Glu Gly Met Lys Asn Lys Thr
    1475                1480                1485

Ile Ser Gln Leu Asn Cys Asn Arg Asn Ala Ser Leu Ser Lys Gln
    1490                1495                1500

Lys Ser Leu Glu Asn Asp Leu Ser Leu Thr Leu Asn Leu Asp Gln
    1505                1510                1515

Arg Leu Ser Leu Gly Ser Asp Glu Ala Asp Leu Val Lys Glu
    1520                1525                1530

Leu Gln Ser Met Cys Ser Ser Lys Ser Glu Ser Asp Ile Ser Lys
    1535                1540                1545

Ile Ala Asp Ser Arg Asp Asp Leu Arg Met Phe Asp Ser Ser Gly
    1550                1555                1560

Asn Asn Pro Val Leu Ser Ala Thr Ile Asn Asn Leu Arg Met Pro
    1565                1570                1575

Val Ser Gln Lys Glu Val Ser Pro Leu Ser Ser His Gln Thr Thr
    1580                1585                1590

Glu Cys Ser Asn Ser Lys Ser Lys Thr Glu Leu Gly Val Ser Arg
    1595                1600                1605

Val Lys Ser Phe Leu Pro Val Pro Arg Ser Lys Val Thr Gln Cys
    1610                1615                1620

Ser Gln Asn Thr Lys Arg Ser Ser Ser Ser Asn Thr Arg Gln
    1625                1630                1635

Ile Glu Ile Asn Asn Asn Ser Lys Glu Val Asn Trp Asn Leu His
    1640                1645                1650

Lys Asn Glu His Leu Glu Lys Pro Asn Lys
    1655                1660

<210> SEQ ID NO 2
<211> LENGTH: 2839
<212> TYPE: PRT
<213> ORGANISM: Homo sapiens

<400> SEQUENCE: 2

Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
                20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
        50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110
```

```
Leu Leu Pro Glu Ile Cys His Phe Leu His Thr Cys Arg Glu Gly Asn
            115                 120                 125

Gln His Ala Ala Glu Leu Arg Asn Ser Ala Ser Gly Val Leu Phe Ser
        130                 135                 140

Leu Ser Cys Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                    165                 170                 175

Ile Glu Leu Leu Gln Tyr Ile Asn Val Asp Cys Ala Lys Leu Lys Arg
                180                 185                 190

Leu Leu Lys Glu Thr Ala Phe Lys Phe Lys Ala Leu Lys Lys Val Ala
            195                 200                 205

Gln Leu Ala Val Ile Asn Ser Leu Glu Lys Ala Phe Trp Asn Trp Val
        210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                    245                 250                 255

Ala Glu Ser Thr Lys Arg Lys Ala Ala Val Trp Pro Leu Gln Ile Ile
                260                 265                 270

Leu Leu Ile Leu Cys Pro Glu Ile Ile Gln Asp Ile Ser Lys Asp Val
            275                 280                 285

Val Asp Glu Asn Asn Met Asn Lys Lys Leu Phe Leu Asp Ser Leu Arg
        290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                    325                 330                 335

Glu Asp Asn Ser Val Ile Phe Leu Val Gln Ser Met Val Val Asp
                340                 345                 350

Leu Lys Asn Leu Leu Phe Asn Pro Ser Lys Pro Phe Ser Arg Gly Ser
            355                 360                 365

Gln Pro Ala Asp Val Asp Leu Met Ile Asp Cys Leu Val Ser Cys Phe
        370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                    405                 410                 415

Ile Ile Thr Asn Ser Ala Leu Asp Trp Trp Pro Lys Ile Asp Ala Val
                420                 425                 430

Tyr Cys His Ser Val Glu Leu Arg Asn Met Phe Gly Glu Thr Leu His
            435                 440                 445

Lys Ala Val Gln Gly Cys Gly Ala His Pro Ala Ile Arg Met Ala Pro
        450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Ser Met
                    485                 490                 495

Val Lys Leu Ile His Ala Asp Pro Lys Leu Leu Cys Asn Pro Arg
                500                 505                 510

Lys Gln Gly Pro Glu Thr Gln Gly Ser Thr Ala Glu Leu Ile Thr Gly
            515                 520                 525
```

-continued

```
Leu Val Gln Leu Val Pro Gln Ser His Met Pro Glu Ile Ala Gln Glu
    530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
    610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
        675                 680                 685

Val Ala Leu Tyr Met Phe Leu Trp Asn Pro Asp Thr Glu Ala Val Leu
    690                 695                 700

Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
            740                 745                 750

Ala Ala Leu Gln Lys Arg Val Met Ala Leu Leu Arg Arg Ile Glu His
        755                 760                 765

Pro Thr Ala Gly Asn Thr Glu Ala Trp Glu Asp Thr His Ala Lys Trp
    770                 775                 780

Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Ser Ile Asp Leu Ser Asp Thr Asp
            820                 825                 830

Ser Leu Gln Glu Trp Ile Asn Met Thr Gly Phe Leu Cys Ala Leu Gly
        835                 840                 845

Gly Val Cys Leu Gln Gln Arg Ser Asn Ser Gly Leu Ala Thr Tyr Ser
    850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
            900                 905                 910

Ile Arg Thr Asn Val Lys Asp Leu Val Gly Leu Glu Leu Ser Pro Ala
        915                 920                 925

Leu Tyr Pro Met Leu Phe Asn Lys Leu Lys Asn Thr Ile Ser Lys Phe
    930                 935                 940

Phe Asp Ser Gln Gly Gln Val Leu Leu Thr Asp Thr Asn Thr Gln Phe
```

-continued

```
945                 950                 955                 960
Val Glu Gln Thr Ile Ala Ile Met Lys Asn Leu Leu Asp Asn His Thr
                965                 970                 975
Glu Gly Ser Ser Glu His Leu Gly Gln Ala Ser Ile Glu Thr Met Met
                980                 985                 990
Leu Asn Leu Val Arg Tyr Val Arg Val Leu Gly Asn Met Val His Ala
            995                 1000                1005
Ile Gln Ile Lys Thr Lys Leu Cys Gln Leu Val Glu Val Met Met
    1010                1015                1020
Ala Arg Arg Asp Asp Leu Ser Phe Cys Gln Glu Met Lys Phe Arg
    1025                1030                1035
Asn Lys Met Val Glu Tyr Leu Thr Asp Trp Val Met Gly Thr Ser
    1040                1045                1050
Asn Gln Ala Ala Asp Asp Val Lys Cys Leu Thr Arg Asp Leu
    1055                1060                1065
Asp Gln Ala Ser Met Glu Ala Val Val Ser Leu Leu Ala Gly Leu
    1070                1075                1080
Pro Leu Gln Pro Glu Glu Gly Asp Gly Val Glu Leu Met Glu Ala
    1085                1090                1095
Lys Ser Gln Leu Phe Leu Lys Tyr Phe Thr Leu Phe Met Asn Leu
    1100                1105                1110
Leu Asn Asp Cys Ser Glu Val Glu Asp Glu Ser Ala Gln Thr Gly
    1115                1120                1125
Gly Arg Lys Arg Gly Met Ser Arg Arg Leu Ala Ser Leu Arg His
    1130                1135                1140
Cys Thr Val Leu Ala Met Ser Asn Leu Leu Asn Ala Asn Val Asp
    1145                1150                1155
Ser Gly Leu Met His Ser Ile Gly Leu Gly Tyr His Lys Asp Leu
    1160                1165                1170
Gln Thr Arg Ala Thr Phe Met Glu Val Leu Thr Lys Ile Leu Gln
    1175                1180                1185
Gln Gly Thr Glu Phe Asp Thr Leu Ala Glu Thr Val Leu Ala Asp
    1190                1195                1200
Arg Phe Glu Arg Leu Val Glu Leu Val Thr Met Met Gly Asp Gln
    1205                1210                1215
Gly Glu Leu Pro Ile Ala Met Ala Leu Ala Asn Val Val Pro Cys
    1220                1225                1230
Ser Gln Trp Asp Glu Leu Ala Arg Val Leu Val Thr Leu Phe Asp
    1235                1240                1245
Ser Arg His Leu Leu Tyr Gln Leu Leu Trp Asn Met Phe Ser Lys
    1250                1255                1260
Glu Val Glu Leu Ala Asp Ser Met Gln Thr Leu Phe Arg Gly Asn
    1265                1270                1275
Ser Leu Ala Ser Lys Ile Met Thr Phe Cys Phe Lys Val Tyr Gly
    1280                1285                1290
Ala Thr Tyr Leu Gln Lys Leu Leu Asp Pro Leu Leu Arg Ile Val
    1295                1300                1305
Ile Thr Ser Ser Asp Trp Gln His Val Ser Phe Glu Val Asp Pro
    1310                1315                1320
Thr Arg Leu Glu Pro Ser Glu Ser Leu Glu Glu Asn Gln Arg Asn
    1325                1330                1335
Leu Leu Gln Met Thr Glu Lys Phe Phe His Ala Ile Ile Ser Ser
    1340                1345                1350
```

```
Ser Ser Glu Phe Pro Pro Gln Leu Arg Ser Val Cys His Cys Leu
    1355            1360                1365

Tyr Gln Ala Thr Cys His Ser Leu Leu Asn Lys Ala Thr Val Lys
    1370            1375                1380

Glu Lys Lys Glu Asn Lys Lys Ser Val Val Ser Gln Arg Phe Pro
    1385            1390                1395

Gln Asn Ser Ile Gly Ala Val Gly Ser Ala Met Phe Leu Arg Phe
    1400            1405                1410

Ile Asn Pro Ala Ile Val Ser Pro Tyr Glu Ala Gly Ile Leu Asp
    1415            1420                1425

Lys Lys Pro Pro Pro Arg Ile Glu Arg Gly Leu Lys Leu Met Ser
    1430            1435                1440

Lys Ile Leu Gln Ser Ile Ala Asn His Val Leu Phe Thr Lys Glu
    1445            1450                1455

Glu His Met Arg Pro Phe Asn Asp Phe Val Lys Ser Asn Phe Asp
    1460            1465                1470

Ala Ala Arg Arg Phe Phe Leu Asp Ile Ala Ser Asp Cys Pro Thr
    1475            1480                1485

Ser Asp Ala Val Asn His Ser Leu Ser Phe Ile Ser Asp Gly Asn
    1490            1495                1500

Val Leu Ala Leu His Arg Leu Leu Trp Asn Asn Gln Glu Lys Ile
    1505            1510                1515

Gly Gln Tyr Leu Ser Ser Asn Arg Asp His Lys Ala Val Gly Arg
    1520            1525                1530

Arg Pro Phe Asp Lys Met Ala Thr Leu Leu Ala Tyr Leu Gly Pro
    1535            1540                1545

Pro Glu His Lys Pro Val Ala Asp Thr His Trp Ser Ser Leu Asn
    1550            1555                1560

Leu Thr Ser Ser Lys Phe Glu Glu Phe Met Thr Arg His Gln Val
    1565            1570                1575

His Glu Lys Glu Glu Phe Lys Ala Leu Lys Thr Leu Ser Ile Phe
    1580            1585                1590

Tyr Gln Ala Gly Thr Ser Lys Ala Gly Asn Pro Ile Phe Tyr Tyr
    1595            1600                1605

Val Ala Arg Arg Phe Lys Thr Gly Gln Ile Asn Gly Asp Leu Leu
    1610            1615                1620

Ile Tyr His Val Leu Leu Thr Leu Lys Pro Tyr Tyr Ala Lys Pro
    1625            1630                1635

Tyr Glu Ile Val Val Asp Leu Thr His Thr Gly Pro Ser Asn Arg
    1640            1645                1650

Phe Lys Thr Asp Phe Leu Ser Lys Trp Phe Val Val Phe Pro Gly
    1655            1660                1665

Phe Ala Tyr Asp Asn Val Ser Ala Val Tyr Ile Tyr Asn Cys Asn
    1670            1675                1680

Ser Trp Val Arg Glu Tyr Thr Lys Tyr His Glu Arg Leu Leu Thr
    1685            1690                1695

Gly Leu Lys Gly Ser Lys Arg Leu Val Phe Ile Asp Cys Pro Gly
    1700            1705                1710

Lys Leu Ala Glu His Ile Glu His Glu Gln Gln Lys Leu Pro Ala
    1715            1720                1725

Ala Thr Leu Ala Leu Glu Glu Asp Leu Lys Val Phe His Asn Ala
    1730            1735                1740
```

```
Leu Lys Leu Ala His Lys Asp Thr Lys Val Ser Ile Lys Val Gly
    1745                1750                1755
Ser Thr Ala Val Gln Val Thr Ser Ala Glu Arg Thr Lys Val Leu
    1760                1765                1770
Gly Gln Ser Val Phe Leu Asn Asp Ile Tyr Tyr Ala Ser Glu Ile
    1775                1780                1785
Glu Glu Ile Cys Leu Val Asp Glu Asn Gln Phe Thr Leu Thr Ile
    1790                1795                1800
Ala Asn Gln Gly Thr Pro Leu Thr Phe Met His Gln Glu Cys Glu
    1805                1810                1815
Ala Ile Val Gln Ser Ile Ile His Ile Arg Thr Arg Trp Glu Leu
    1820                1825                1830
Ser Gln Pro Asp Ser Ile Pro Gln His Thr Lys Ile Arg Pro Lys
    1835                1840                1845
Asp Val Pro Gly Thr Leu Leu Asn Ile Ala Leu Leu Asn Leu Gly
    1850                1855                1860
Ser Ser Asp Pro Ser Leu Arg Ser Ala Ala Tyr Asn Leu Leu Cys
    1865                1870                1875
Ala Leu Thr Cys Thr Phe Asn Leu Lys Ile Glu Gly Gln Leu Leu
    1880                1885                1890
Glu Thr Ser Gly Leu Cys Ile Pro Ala Asn Asn Thr Leu Phe Ile
    1895                1900                1905
Val Ser Ile Ser Lys Thr Leu Ala Ala Asn Glu Pro His Leu Thr
    1910                1915                1920
Leu Glu Phe Leu Glu Glu Cys Ile Ser Gly Phe Ser Lys Ser Ser
    1925                1930                1935
Ile Glu Leu Lys His Leu Cys Leu Glu Tyr Met Thr Pro Trp Leu
    1940                1945                1950
Ser Asn Leu Val Arg Phe Cys Lys His Asn Asp Asp Ala Lys Arg
    1955                1960                1965
Gln Arg Val Thr Ala Ile Leu Asp Lys Leu Ile Thr Met Thr Ile
    1970                1975                1980
Asn Glu Lys Gln Met Tyr Pro Ser Ile Gln Ala Lys Ile Trp Gly
    1985                1990                1995
Ser Leu Gly Gln Ile Thr Asp Leu Leu Asp Val Val Leu Asp Ser
    2000                2005                2010
Phe Ile Lys Thr Ser Ala Thr Gly Gly Leu Gly Ser Ile Lys Ala
    2015                2020                2025
Glu Val Met Ala Asp Thr Ala Val Ala Leu Ala Ser Gly Asn Val
    2030                2035                2040
Lys Leu Val Ser Ser Lys Val Ile Gly Arg Met Cys Lys Ile Ile
    2045                2050                2055
Asp Lys Thr Cys Leu Ser Pro Thr Pro Thr Leu Glu Gln His Leu
    2060                2065                2070
Met Trp Asp Asp Ile Ala Ile Leu Ala Arg Tyr Met Leu Met Leu
    2075                2080                2085
Ser Phe Asn Asn Ser Leu Asp Val Ala Ala His Leu Pro Tyr Leu
    2090                2095                2100
Phe His Val Val Thr Phe Leu Val Ala Thr Gly Pro Leu Ser Leu
    2105                2110                2115
Arg Ala Ser Thr His Gly Leu Val Ile Asn Ile Ile His Ser Leu
    2120                2125                2130
Cys Thr Cys Ser Gln Leu His Phe Ser Glu Glu Thr Lys Gln Val
```

-continued

|   |   |   | 2135 |   |   |   | 2140 |   |   |   | 2145 |
|---|---|---|---|---|---|---|---|---|---|---|---|

Leu Arg Leu Ser Leu Thr Glu Phe Ser Leu Pro Lys Phe Tyr Leu
            2150                2155              2160

Leu Phe Gly Ile Ser Lys Val Lys Ser Ala Ala Val Ile Ala Phe
            2165                2170              2175

Arg Ser Ser Tyr Arg Asp Arg Ser Phe Ser Pro Gly Ser Tyr Glu
            2180                2185              2190

Arg Glu Thr Phe Ala Leu Thr Ser Leu Glu Thr Val Thr Glu Ala
            2195                2200              2205

Leu Leu Glu Ile Met Glu Ala Cys Met Arg Asp Ile Pro Thr Cys
            2210                2215              2220

Lys Trp Leu Asp Gln Trp Thr Glu Leu Ala Gln Arg Phe Ala Phe
            2225                2230              2235

Gln Tyr Asn Pro Ser Leu Gln Pro Arg Ala Leu Val Val Phe Gly
            2240                2245              2250

Cys Ile Ser Lys Arg Val Ser His Gly Gln Ile Lys Gln Ile Ile
            2255                2260              2265

Arg Ile Leu Ser Lys Ala Leu Glu Ser Cys Leu Lys Gly Pro Asp
            2270                2275              2280

Thr Tyr Asn Ser Gln Val Leu Ile Glu Ala Thr Val Ile Ala Leu
            2285                2290              2295

Thr Lys Leu Gln Pro Leu Leu Asn Lys Asp Ser Pro Leu His Lys
            2300                2305              2310

Ala Leu Phe Trp Val Ala Val Ala Val Leu Gln Leu Asp Glu Val
            2315                2320              2325

Asn Leu Tyr Ser Ala Gly Thr Ala Leu Leu Glu Gln Asn Leu His
            2330                2335              2340

Thr Leu Asp Ser Leu Arg Ile Phe Asn Asp Lys Ser Pro Glu Glu
            2345                2350              2355

Val Phe Met Ala Ile Arg Asn Pro Leu Glu Trp His Cys Lys Gln
            2360                2365              2370

Met Asp His Phe Val Gly Leu Asn Phe Asn Ser Asn Phe Asn Phe
            2375                2380              2385

Ala Leu Val Gly His Leu Leu Lys Gly Tyr Arg His Pro Ser Pro
            2390                2395              2400

Ala Ile Val Ala Arg Thr Val Arg Ile Leu His Thr Leu Leu Thr
            2405                2410              2415

Leu Val Asn Lys His Arg Asn Cys Asp Lys Phe Glu Val Asn Thr
            2420                2425              2430

Gln Ser Val Ala Tyr Leu Ala Ala Leu Leu Thr Val Ser Glu Glu
            2435                2440              2445

Val Arg Ser Arg Cys Ser Leu Lys His Arg Lys Ser Leu Leu Leu
            2450                2455              2460

Thr Asp Ile Ser Met Glu Asn Val Pro Met Asp Thr Tyr Pro Ile
            2465                2470              2475

His His Gly Asp Pro Ser Tyr Arg Thr Leu Lys Glu Thr Gln Pro
            2480                2485              2490

Trp Ser Ser Pro Lys Gly Ser Glu Gly Tyr Leu Ala Ala Thr Tyr
            2495                2500              2505

Pro Thr Val Gly Gln Thr Ser Pro Arg Ala Arg Lys Ser Met Ser
            2510                2515              2520

Leu Asp Met Gly Gln Pro Ser Gln Ala Asn Thr Lys Lys Leu Leu
            2525                2530              2535

-continued

```
Gly Thr Arg Lys Ser Phe Asp His Leu Ile Ser Asp Thr Lys Ala
    2540                2545                2550

Pro Lys Arg Gln Glu Met Glu Ser Gly Ile Thr Thr Pro Pro Lys
    2555                2560                2565

Met Arg Arg Val Ala Glu Thr Asp Tyr Glu Met Glu Thr Gln Arg
    2570                2575                2580

Ile Ser Ser Ser Gln Gln His Pro His Leu Arg Lys Val Ser Val
    2585                2590                2595

Ser Glu Ser Asn Val Leu Leu Asp Glu Glu Val Leu Thr Asp Pro
    2600                2605                2610

Lys Ile Gln Ala Leu Leu Leu Thr Val Leu Ala Thr Leu Val Lys
    2615                2620                2625

Tyr Thr Thr Asp Glu Phe Asp Gln Arg Ile Leu Tyr Glu Tyr Leu
    2630                2635                2640

Ala Glu Ala Ser Val Val Phe Pro Lys Val Phe Pro Val Val His
    2645                2650                2655

Asn Leu Leu Asp Ser Lys Ile Asn Thr Leu Leu Ser Leu Cys Gln
    2660                2665                2670

Asp Pro Asn Leu Leu Asn Pro Ile His Gly Ile Val Gln Ser Val
    2675                2680                2685

Val Tyr His Glu Glu Ser Pro Pro Gln Tyr Gln Thr Ser Tyr Leu
    2690                2695                2700

Gln Ser Phe Gly Phe Asn Gly Leu Trp Arg Phe Ala Gly Pro Phe
    2705                2710                2715

Ser Lys Gln Thr Gln Ile Pro Asp Tyr Ala Glu Leu Ile Val Lys
    2720                2725                2730

Phe Leu Asp Ala Leu Ile Asp Thr Tyr Leu Pro Gly Ile Asp Glu
    2735                2740                2745

Glu Thr Ser Glu Glu Ser Leu Leu Thr Pro Thr Ser Pro Tyr Pro
    2750                2755                2760

Pro Ala Leu Gln Ser Gln Leu Ser Ile Thr Ala Asn Leu Asn Leu
    2765                2770                2775

Ser Asn Ser Met Thr Ser Leu Ala Thr Ser Gln His Ser Pro Gly
    2780                2785                2790

Ile Asp Lys Glu Asn Val Glu Leu Ser Pro Thr Thr Gly His Cys
    2795                2800                2805

Asn Ser Gly Arg Thr Arg His Gly Ser Ala Ser Gln Val Gln Lys
    2810                2815                2820

Gln Arg Ser Ala Gly Ser Phe Lys Arg Asn Ser Ile Lys Lys Ile
    2825                2830                2835

Val
```

<210> SEQ ID NO 3
<211> LENGTH: 682
<212> TYPE: PRT
<213> ORGANISM: Homo sapiens

<400> SEQUENCE: 3

```
Met Gln Leu Glu His Cys Leu Ser Pro Ser Ile Met Leu Ser Lys Lys
1               5                   10                  15

Phe Leu Asn Val Ser Ser Ser Tyr Pro His Ser Gly Gly Ser Glu Leu
                20                  25                  30

Val Leu His Asp His Pro Ile Ser Thr Thr Asp Asn Leu Glu Arg
            35                  40                  45
```

```
Ser Ser Pro Leu Lys Lys Ile Thr Arg Gly Met Thr Asn Gln Ser Asp
     50                  55                  60

Thr Asp Asn Phe Pro Asp Ser Lys Asp Ser Pro Gly Asp Val Gln Arg
 65                  70                  75                  80

Ser Lys Leu Ser Pro Val Leu Asp Gly Val Ser Glu Leu Arg His Ser
             85                  90                  95

Phe Asp Gly Ser Ala Ala Asp Arg Tyr Leu Leu Ser Gln Ser Ser Gln
            100                 105                 110

Pro Gln Ser Ala Ala Thr Ala Pro Ser Ala Met Phe Pro Tyr Pro Gly
        115                 120                 125

Gln His Gly Pro Ala His Pro Ala Phe Ser Ile Gly Ser Pro Ser Arg
        130                 135                 140

Tyr Met Ala His His Pro Val Ile Thr Asn Gly Ala Tyr Asn Ser Leu
145                 150                 155                 160

Leu Ser Asn Ser Ser Pro Gln Gly Tyr Pro Thr Ala Gly Tyr Pro Tyr
                165                 170                 175

Pro Gln Gln Tyr Gly His Ser Tyr Gln Gly Ala Pro Phe Tyr Gln Phe
            180                 185                 190

Ser Ser Thr Gln Pro Gly Leu Val Pro Gly Lys Ala Gln Val Tyr Leu
        195                 200                 205

Cys Asn Arg Pro Leu Trp Leu Lys Phe His Arg His Gln Thr Glu Met
210                 215                 220

Ile Ile Thr Lys Gln Gly Arg Arg Met Phe Pro Phe Leu Ser Phe Asn
225                 230                 235                 240

Ile Ser Gly Leu Asp Pro Thr Ala His Tyr Asn Ile Phe Val Asp Val
                245                 250                 255

Ile Leu Ala Asp Pro Asn His Trp Arg Phe Gln Gly Gly Lys Trp Val
            260                 265                 270

Pro Cys Gly Lys Ala Asp Thr Asn Val Gln Gly Asn Arg Val Tyr Met
        275                 280                 285

His Pro Asp Ser Pro Asn Thr Gly Ala His Trp Met Arg Gln Glu Ile
        290                 295                 300

Ser Phe Gly Lys Leu Lys Leu Thr Asn Asn Lys Gly Ala Ser Asn Asn
305                 310                 315                 320

Asn Gly Gln Met Val Val Leu Gln Ser Leu His Lys Tyr Gln Pro Arg
                325                 330                 335

Leu His Val Val Glu Val Asn Glu Asp Gly Thr Glu Asp Thr Ser Gln
            340                 345                 350

Pro Gly Arg Val Gln Thr Phe Thr Phe Pro Glu Thr Gln Phe Ile Ala
        355                 360                 365

Val Thr Ala Tyr Gln Asn Thr Asp Ile Thr Gln Leu Lys Ile Asp His
        370                 375                 380

Asn Pro Phe Ala Lys Gly Phe Arg Asp Asn Tyr Asp Thr Ile Tyr Thr
385                 390                 395                 400

Gly Cys Asp Met Asp Arg Leu Thr Pro Ser Pro Asn Asp Ser Pro Arg
                405                 410                 415

Ser Gln Ile Val Pro Gly Ala Arg Tyr Ala Met Ala Gly Ser Phe Leu
            420                 425                 430

Gln Asp Gln Phe Val Ser Asn Tyr Ala Lys Ala Arg Phe His Pro Gly
        435                 440                 445

Ala Gly Ala Gly Pro Gly Pro Gly Thr Asp Arg Ser Val Pro His Thr
        450                 455                 460
```

-continued

```
Asn Gly Leu Leu Ser Pro Gln Gln Ala Glu Asp Pro Gly Ala Pro Ser
465                 470                 475                 480

Pro Gln Arg Trp Phe Val Thr Pro Ala Asn Asn Arg Leu Asp Phe Ala
            485                 490                 495

Ala Ser Ala Tyr Asp Thr Ala Thr Asp Phe Ala Gly Asn Ala Ala Thr
        500                 505                 510

Leu Leu Ser Tyr Ala Ala Ala Gly Val Lys Ala Leu Pro Leu Gln Ala
    515                 520                 525

Ala Gly Cys Thr Gly Arg Pro Leu Gly Tyr Tyr Ala Asp Pro Ser Gly
530                 535                 540

Trp Gly Ala Arg Ser Pro Pro Gln Tyr Cys Gly Thr Lys Ser Gly Ser
545                 550                 555                 560

Val Leu Pro Cys Trp Pro Asn Ser Ala Ala Ala Ala Arg Met Ala
                565                 570                 575

Gly Ala Asn Pro Tyr Leu Gly Glu Glu Ala Glu Gly Leu Ala Ala Glu
            580                 585                 590

Arg Ser Pro Leu Pro Pro Gly Ala Ala Glu Asp Ala Lys Pro Lys Asp
            595                 600                 605

Leu Ser Asp Ser Ser Trp Ile Glu Thr Pro Ser Ser Ile Lys Ser Ile
        610                 615                 620

Asp Ser Ser Asp Ser Gly Ile Tyr Glu Gln Ala Lys Arg Arg Arg Ile
625                 630                 635                 640

Ser Pro Ala Asp Thr Pro Val Ser Glu Ser Ser Ser Pro Leu Lys Ser
                645                 650                 655

Glu Val Leu Ala Gln Arg Asp Cys Glu Lys Asn Cys Ala Lys Asp Ile
            660                 665                 670

Ser Gly Tyr Tyr Gly Phe Tyr Ser His Ser
        675                 680

<210> SEQ ID NO 4
<211> LENGTH: 630
<212> TYPE: PRT
<213> ORGANISM: Mus musculus

<400> SEQUENCE: 4

Met Ala Thr Asp Ser Ala Ser Cys Glu Pro Asp Leu Ser Arg Thr Pro
1               5                   10                  15

Gly Asp Thr Glu Gly Ala Thr Ala Glu Ala Ala Lys Lys Glu Phe Asp
            20                  25                  30

Val Asp Thr Leu Ser Lys Ser Glu Leu Arg Met Leu Leu Ser Val Met
        35                  40                  45

Glu Gly Glu Leu Glu Ala Arg Asp Leu Val Ile Glu Ala Leu Arg Ala
    50                  55                  60

Arg Arg Lys Glu Val Phe Ile Gln Glu Arg Tyr Gly Arg Phe Asn Leu
65                  70                  75                  80

Asn Asp Pro Phe Leu Ala Leu Gln Arg Asp Tyr Glu Ala Gly Pro Gly
            85                  90                  95

Asp Lys Glu Lys Pro Val Cys Thr Asn Pro Leu Ser Ile Leu Glu Ala
            100                 105                 110

Val Met Ala His Cys Arg Lys Met Gln Glu Arg Met Ser Ala Gln Leu
        115                 120                 125

Val Ala Ala Glu Ser Arg Gln Lys Lys Leu Glu Met Glu Lys Leu Gln
    130                 135                 140

Leu Gln Ala Leu Glu Gln Glu His Lys Lys Leu Ala Ala His Leu Glu
145                 150                 155                 160
```

```
Glu Glu Arg Gly Lys Asn Lys His Val Val Leu Met Leu Val Lys Glu
            165                 170                 175

Cys Lys Gln Leu Ser Gly Lys Val Val Glu Ala Gln Lys Leu Glu
            180                 185                 190

Glu Val Met Ala Gln Leu Glu Glu Lys Lys Thr Ser Glu Leu
        195                 200                 205

Glu Glu Gln Leu Ser Ala Glu Lys Gln Arg Ser Ser Gly Met Glu Ala
        210                 215                 220

Gln Leu Glu Lys Gln Leu Ser Glu Phe Asp Thr Glu Arg Glu Gln Leu
225                 230                 235                 240

Arg Ala Lys Leu Ser Arg Glu Glu Ala His Thr Thr Asp Leu Lys Glu
            245                 250                 255

Glu Ile Asp Lys Met Lys Lys Met Met Glu Gln Met Lys Lys Gly Ser
            260                 265                 270

Asp Gly Lys Pro Gly Leu Ser Leu Pro Arg Lys Thr Lys Asp Lys Arg
            275                 280                 285

Leu Ala Ser Ile Ser Val Ala Thr Glu Gly Pro Val Thr Arg Ser Val
            290                 295                 300

Ala Cys Gln Thr Asp Val Val Thr Glu Ser Thr Asp Pro Val Lys Lys
305                 310                 315                 320

Leu Pro Leu Thr Val Pro Ile Lys Pro Ser Thr Gly Ser Pro Leu Val
            325                 330                 335

Pro Thr Asn Thr Lys Gly Asn Val Gly Pro Ser Ala Leu Leu Ile Arg
            340                 345                 350

Pro Gly Ile Asp Arg Gln Ser Ser His Ser Asp Leu Gly Pro Ser Pro
            355                 360                 365

Pro Thr Ala Leu Pro Ser Ser Ala Asn Arg Ile Glu Glu Asn Gly Pro
            370                 375                 380

Ser Thr Gly Asn Ala Pro Asp Leu Ser Asn Ser Thr Pro Ser Thr Pro
385                 390                 395                 400

Ser Ser Thr Ala Pro Ala Ala Gln Thr Pro Gly Thr Ala Pro Gln
            405                 410                 415

Asn His Ser Gln Ala Pro Thr Val His Ser Leu His Ser Pro Cys Ala
            420                 425                 430

Asn Thr His Pro Gly Leu Asn Pro Arg Ile Gln Ala Ala Arg Phe Arg
            435                 440                 445

Phe Gln Gly Asn Ala Asn Asp Pro Asp Gln Asn Gly Asn Asn Thr Gln
            450                 455                 460

Ser Pro Pro Ser Arg Asp Val Ser Pro Thr Ser Arg Asp Asn Leu Val
465                 470                 475                 480

Ala Lys Gln Leu Ala Arg Asn Thr Val Thr Gln Ala Leu Ser Arg Phe
            485                 490                 495

Thr Ser Pro Gln Ala Gly Ala Ser Ser Arg Leu Gly Val Ser Pro Gly
            500                 505                 510

Gly Asp Ala Gly Thr Cys Pro Pro Val Gly Arg Thr Gly Leu Lys Thr
            515                 520                 525

Pro Gly Ala Ala Arg Val Asp Arg Gly Asn Pro Pro Ile Pro Pro
            530                 535                 540

Lys Lys Pro Gly Leu Ser Gln Thr Pro Ser Pro His Pro Gln Leu
545                 550                 555                 560

Arg Ala Ser Asn Ala Gly Ala Lys Val Asp Asn Lys Ile Val Ala Ser
            565                 570                 575
```

-continued

Pro Pro Ser Thr Leu Pro Gln Gly Thr Lys Val Val Asn Glu Asn
               580                 585                 590

Val Pro Lys Ser Ser Ser Pro Gln Leu Pro Pro Lys Pro Ser Ile Asp
        595                 600                 605

Leu Thr Val Ala Pro Ala Gly Cys Pro Val Ser Ala Leu Ala Thr Ser
610                 615                 620

Gln Ala Gly His Pro Pro
625                 630

<210> SEQ ID NO 5
<211> LENGTH: 630
<212> TYPE: PRT
<213> ORGANISM: Mus musculus

<400> SEQUENCE: 5

Met Ala Thr Asp Ser Ala Ser Cys Glu Pro Asp Leu Ser Arg Thr Pro
1               5                   10                  15

Gly Asp Thr Glu Gly Ala Thr Ala Glu Ala Ala Lys Lys Glu Phe Asp
            20                  25                  30

Val Asp Thr Leu Ser Lys Ser Glu Leu Arg Met Leu Leu Ser Val Met
        35                  40                  45

Glu Gly Glu Leu Glu Ala Arg Asp Leu Val Ile Glu Ala Leu Arg Ala
50                  55                  60

Arg Arg Lys Glu Val Phe Ile Gln Glu Arg Tyr Gly Arg Phe Asn Leu
65                  70                  75                  80

Asn Asp Pro Phe Leu Ala Leu Gln Arg Asp Tyr Glu Ala Gly Pro Gly
                85                  90                  95

Asp Lys Glu Lys Pro Val Cys Thr Asn Pro Leu Ser Ile Leu Glu Ala
            100                 105                 110

Val Met Ala His Cys Arg Lys Ile Gln Glu Arg Met Ser Ala Gln Leu
        115                 120                 125

Val Ala Ala Glu Ser Arg Gln Lys Lys Leu Glu Met Glu Lys Leu Gln
130                 135                 140

Leu Gln Ala Leu Glu Gln Glu His Lys Lys Leu Ala Ala His Leu Glu
145                 150                 155                 160

Glu Glu Arg Gly Lys Asn Lys His Val Val Leu Met Leu Val Lys Glu
                165                 170                 175

Cys Lys Gln Leu Ser Gly Lys Val Val Glu Glu Ala Gln Lys Leu Glu
            180                 185                 190

Glu Val Met Ala Gln Leu Glu Glu Lys Lys Thr Ser Glu Leu
        195                 200                 205

Glu Glu Gln Leu Ser Ala Glu Lys Gln Arg Ser Ser Gly Met Glu Ala
210                 215                 220

Gln Leu Glu Lys Gln Leu Ser Glu Phe Asp Thr Glu Arg Glu Gln Leu
225                 230                 235                 240

Arg Ala Lys Leu Ser Arg Glu Glu Ala His Thr Thr Asp Leu Lys Glu
                245                 250                 255

Glu Ile Asp Lys Met Lys Lys Met Glu Gln Met Lys Lys Gly Ser
            260                 265                 270

Asp Gly Lys Pro Gly Leu Ser Leu Pro Arg Lys Thr Lys Asp Lys Arg
        275                 280                 285

Leu Ala Ser Ile Ser Val Ala Thr Glu Gly Pro Val Thr Arg Ser Val
290                 295                 300

Ala Cys Gln Thr Asp Val Val Thr Glu Ser Thr Asp Pro Val Lys Lys
305                 310                 315                 320

```
Leu Pro Leu Thr Val Pro Ile Lys Pro Ser Thr Gly Ser Pro Leu Val
            325                 330                 335

Pro Thr Asn Thr Lys Gly Asn Val Gly Pro Ser Ala Leu Leu Ile Arg
            340                 345                 350

Pro Gly Ile Asp Arg Gln Ser His Ser Asp Leu Gly Pro Ser Pro
            355                 360                 365

Pro Thr Ala Leu Pro Ser Ser Ala Asn Arg Ile Glu Glu Asn Gly Pro
            370                 375                 380

Ser Thr Gly Asn Ala Pro Asp Leu Ser Asn Ser Thr Pro Ser Thr Pro
385                 390                 395                 400

Ser Ser Thr Ala Pro Ala Ala Gln Thr Pro Gly Thr Ala Pro Gln
            405                 410                 415

Asn His Ser Gln Ala Pro Thr Val His Ser Leu His Ser Pro Cys Ala
            420                 425                 430

Asn Thr His Pro Gly Leu Asn Pro Arg Ile Gln Ala Ala Arg Phe Arg
            435                 440                 445

Phe Gln Gly Asn Ala Asn Asp Pro Asp Gln Asn Gly Asn Asn Thr Gln
            450                 455                 460

Ser Pro Pro Ser Arg Asp Val Ser Pro Thr Ser Arg Asp Asn Leu Val
465                 470                 475                 480

Ala Lys Gln Leu Ala Arg Asn Thr Val Thr Gln Ala Leu Ser Arg Phe
            485                 490                 495

Thr Ser Pro Gln Ala Gly Ala Ser Ser Arg Leu Gly Val Ser Pro Gly
            500                 505                 510

Gly Asp Ala Gly Thr Cys Pro Pro Val Gly Arg Thr Gly Leu Lys Thr
            515                 520                 525

Pro Gly Ala Ala Arg Val Asp Arg Gly Asn Pro Pro Ile Pro Pro
            530                 535                 540

Lys Lys Pro Gly Leu Ser Gln Thr Pro Ser Pro Pro His Pro Gln Leu
545                 550                 555                 560

Arg Ala Ser Asn Ala Gly Ala Lys Val Asp Asn Lys Ile Val Ala Ser
            565                 570                 575

Pro Pro Ser Thr Leu Pro Gln Gly Thr Lys Val Val Asn Glu Glu Asn
            580                 585                 590

Val Pro Lys Ser Ser Ser Pro Gln Leu Pro Pro Lys Pro Ser Ile Asp
            595                 600                 605

Leu Thr Val Ala Pro Ala Gly Cys Pro Val Ser Ala Leu Ala Thr Ser
            610                 615                 620

Gln Ala Gly His Pro Pro
625                 630

<210> SEQ ID NO 6
<211> LENGTH: 532
<212> TYPE: PRT
<213> ORGANISM: Mus musculus

<400> SEQUENCE: 6

Met Ala Thr Asp Ser Ala Ser Cys Glu Pro Asp Leu Ser Arg Thr Pro
1               5                   10                  15

Gly Asp Thr Glu Gly Ala Thr Ala Glu Ala Ala Lys Lys Glu Phe Asp
            20                  25                  30

Val Asp Thr Leu Ser Lys Ser Glu Leu Arg Met Leu Leu Ser Val Met
            35                  40                  45

Glu Gly Glu Leu Glu Ala Arg Asp Leu Val Ile Glu Ala Leu Arg Ala
```

-continued

```
                 50                  55                  60
Arg Arg Lys Glu Val Phe Ile Gln Glu Arg Tyr Gly Arg Phe Asn Leu
 65                  70                  75                  80

Asn Asp Pro Phe Leu Ala Leu Gln Arg Asp Tyr Glu Ala Gly Pro Gly
                     85                  90                  95

Asp Lys Glu Lys Pro Val Cys Thr Asn Pro Leu Ser Ile Leu Glu Ala
                100                 105                 110

Val Met Ala His Cys Arg Lys Met Gln Glu Arg Met Ser Ala Gln Leu
            115                 120                 125

Val Ala Ala Glu Ser Arg Gln Lys Lys Leu Glu Met Glu Lys Leu Gln
130                 135                 140

Leu Gln Ala Leu Glu Gln Glu His Lys Lys Leu Ala Ala His Leu Glu
145                 150                 155                 160

Glu Glu Arg Gly Lys Asn Lys His Val Val Leu Met Leu Val Lys Glu
                165                 170                 175

Cys Lys Gln Leu Ser Gly Lys Val Val Glu Ala Gln Lys Leu Glu
                180                 185                 190

Glu Val Met Ala Gln Leu Glu Glu Lys Lys Lys Thr Ser Glu Leu
            195                 200                 205

Glu Glu Gln Leu Ser Ala Glu Lys Gln Arg Ser Ser Gly Met Glu Ala
210                 215                 220

Gln Leu Glu Lys Gln Leu Ser Glu Phe Asp Thr Glu Arg Glu Gln Leu
225                 230                 235                 240

Arg Ala Lys Leu Ser Arg Glu Glu Ala His Thr Thr Asp Leu Lys Glu
                245                 250                 255

Glu Ile Asp Lys Met Lys Lys Met Met Glu Gln Met Lys Lys Gly Ser
            260                 265                 270

Asp Gly Lys Pro Gly Leu Ser Leu Pro Arg Lys Thr Lys Asp Lys Arg
                275                 280                 285

Leu Ala Ser Ile Ser Val Ala Thr Glu Gly Pro Val Thr Arg Ser Val
            290                 295                 300

Ala Cys Gln Thr Asp Val Val Thr Glu Ser Thr Asp Pro Val Lys Lys
305                 310                 315                 320

Leu Pro Leu Thr Val Pro Ile Lys Pro Ser Thr Gly Ser Pro Leu Val
                325                 330                 335

Pro Thr Asn Thr Lys Gly Asn Val Gly Pro Ser Ala Leu Leu Ile Arg
                340                 345                 350

Pro Gly Ile Asp Arg Gln Ser Ser His Ser Asp Leu Gly Pro Ser Pro
                355                 360                 365

Pro Thr Ala Leu Pro Ser Ser Ala Asn Arg Ile Glu Glu Asn Gly Pro
370                 375                 380

Ser Thr Gly Asn Ala Pro Asp Leu Ser Asn Ser Thr Pro Ser Thr Pro
385                 390                 395                 400

Ser Ser Thr Ala Pro Ala Ala Ala Gln Thr Pro Gly Thr Ala Pro Gln
                405                 410                 415

Asn His Ser Gln Ala Pro Thr Val His Ser Leu His Ser Pro Cys Ala
                420                 425                 430

Asn Thr His Pro Gly Leu Asn Pro Arg Ile Gln Ala Ala Arg Phe Arg
            435                 440                 445

Phe Gln Gly Asn Ala Asn Asp Pro Asp Gln Asn Gly Asn Asn Thr Gln
450                 455                 460

Ser Pro Pro Ser Arg Asp Val Ser Pro Thr Ser Arg Asp Asn Leu Val
465                 470                 475                 480
```

```
Ala Lys Gln Leu Ala Arg Asn Thr Val Thr Gln Ala Leu Ser Arg Phe
            485                 490                 495

Thr Ser Pro Gln Ala Gly Ala Ser Ser Arg Leu Gly Val Ser Pro Gly
            500                 505                 510

Gly Asp Ala Gly Thr Cys Pro Pro Val Gly Arg Thr Gly Leu Lys Thr
            515                 520                 525

Pro Gly Ala Ala
    530

<210> SEQ ID NO 7
<211> LENGTH: 17
<212> TYPE: DNA
<213> ORGANISM: Mus musculus

<400> SEQUENCE: 7
tgcaagaaag gatgtcc                                                17

<210> SEQ ID NO 8
<211> LENGTH: 17
<212> TYPE: DNA
<213> ORGANISM: Mus musculus

<400> SEQUENCE: 8
gctgagagca gacaaaa                                                17

<210> SEQ ID NO 9
<211> LENGTH: 15
<212> TYPE: DNA
<213> ORGANISM: Mus musculus

<400> SEQUENCE: 9
gcacagctgg tggcc                                                  15

<210> SEQ ID NO 10
<211> LENGTH: 14
<212> TYPE: DNA
<213> ORGANISM: Mus musculus

<400> SEQUENCE: 10
gcacagtggt ggcc                                                   14

<210> SEQ ID NO 11
<211> LENGTH: 13
<212> TYPE: DNA
<213> ORGANISM: Mus musculus

<400> SEQUENCE: 11
gcacagggtg gcc                                                    13
```

TREATMENT FOR AUTISTIC SPECTRUM DISORDER (ASD) AND RELEVANT SYMPTOMS

RELATED APPLICATIONS

This application claims the benefit of U.S. provisional application No. 62/924,269, filed Oct. 22, 2019 under 35 U.S.C. § 119, the entire content of which is incorporated herein by reference.

TECHNOLOGY FIELD

The present invention relates to a method for treating autism spectrum disorders (ASD) or ASD-like symptom, particularly by administering a zinc ion source and/or a serine component e.g. D-serine or its precursor/analogue, optionally in combination with a mixture of branched-chain amino acids (BCAAs). The present invention also relates to a combination, kit or composition for performing the method for treatment as described herein. Further described is use of a zinc ion source and/or a serine component and optional BCAAs for manufacturing a medicament for treating a symptom or disease characteristics associated with ASD or ASD-associated disorder or as a food supplement for ameliorating relevant symptoms in a subject in need thereof. The present invention further provides an animal model for autistic spectrum disorder (ASD) with deficient CTTNBP2 gene, and a method for identifying an ingredient effective in the treatment of ASD by using such animal model.

BACKGROUND OF THE INVENTION

Autism spectrum disorders (ASD) are highly prevalent neurodevelopmental disorders characterized by two core behavioral symptoms; one is impaired social interaction and communication and the other is repetitive behaviors and sensory abnormality [1]. Genetic factors contribute significantly to around 83% of ASD cases [2]. Gene ontology analysis has further indicated that two categories of proteins are particularly important for ASD. One is a group of proteins involved in synaptic organization and signaling and the other group regulates gene expression by controlling transcription and chromatin conformation [3-5]. Investigating how synapse and gene expression defects result in behavioral deficits is expected to unravel ASD etiology.

Whole exome sequencing has revealed that Cortactin-binding protein 2 (CTTNBP2, also known as cortactin-binding protein 90 kDa, CBP90 in short) is one of 71 high-risk loci linked to ASD [3-5]. CTTNBP2 was named because of its ability to bind cortactin, a ubiquitously expressed actin cytoskeleton regulator controlling dendritic spine formation [6], via its proline (P)-rich motif [7]. Since CTTNBP2 is predominantly expressed in neurons [7-9], it has been proposed to guide cortactin's neuron-specific functions [9, 10]. CTTNBP2 is highly enriched at dendritic spines [9, 10] and is also associated with a postsynaptic density protein complex containing SHANK3, CYFIP2 and TNIK [11]. CTTNBP2 controls the mobility of cortactin at dendritic spines and regulates dendritic spine formation and maintenance in mature hippocampal neurons [9]. Cttnbp2 knockdown reduces the density and size of dendritic spines, as well as the frequency of miniature excitatory postsynaptic currents [9]. Before dendritic spines form, CTTNBP2 associates with microtubules via its middle domain, and controls microtubule stability and dendritic arborization [12]. Thus, CTTNBP2 is a critical regulator of actin and microtubule cytoskeletons, thereby controlling neuronal morphology and activity.

Based on sequence analysis of an expressed sequence tag (EST, https://www.ncbi.nlm.nih.gov/nuccore/?term=cttnbp2) in different tissues, the mouse Cttnbp2 gene expresses three different transcripts, namely long, short and intron-retention forms [9]. By means of RT-PCR and immunoblotting, the short form of CTTNBP2 was identified as the major transcript generating protein product (~90 kDa) in brain [9]. The long and intron-retention forms were undetectable in brain by RT-PCR and immunoblotting [9]. These results are consistent with an original SDS-PAGE study showing that CBP90, i.e. CTTNBP2, is a protein species of ~90 kDa [7]. Furthermore, expression of a Cttnbp2 short form silent mutant resistant to an RNAi knockdown construct could rescue the defects of dendritic spine formation and arborization caused by RNAi knockdown [9]. Consequently, the short form is the functional version of CTTNBP2 in the brain. Although CTTNBP2 has been identified as an ASD-associated gene and to be a neuron-predominant cytoskeleton regulator of dendritic spine formation, it remains unclear if and how CTTNBP2 is relevant to ASD via that activity.

SUMMARY OF THE INVENTION

In this report, we aim to explore the roles of CTTNBP2 in regulating brain function and mouse behaviors. Cttnbp2 knockout mice and ASD-associated mutant mice were generated for functional and mechanistic analyses. Since only the short form of CTTNBP2 is expressed in brain, we analyzed ASD-associated mutations within the short form. We performed behavioral analyses to demonstrate impaired social interaction in Cttnbp2 knockout and ASD-associated mutant mice, supporting the link between CTTNBP2 and ASD. We further characterized neuronal activation in vivo by C-FOS expression and assessed dendritic spine deficits. Molecular deficits at synapses of Cttnbp2 mutant mice were then analyzed using proteomic approaches and immunoblotting. The results suggest that CTTNBP2 controls synaptic expression of several protein networks, including NMDARs and their downstream scaffold proteins (such as SHANK3, SHANK2 and SHANK1) and signaling molecules (such as PP2A and RAS). Twenty-eight CTTNBP2-regulated synaptic proteins have been associated with ASD and other neurological diseases. Thus, CTTNBP2 may control synaptic expression of these disease-linked proteins to regulate ASD phenotypes. Finally, zinc supplementation and D-cycloserine treatment of Cttnbp2 mutant mice ameliorated their social deficits, confirming the molecular etiology of CTTNBP2-related ASD. Our results suggest that CTTNBP2 acts as an important regulator of the distribution of several synaptic proteins, including NMDAR and ASD-associated proteins, to control autism-like behaviors and our findings suggest a possible therapeutic treatment for ASD.

Specifically, in the present invention, it is disclosed that a zinc ion source and/or a serine component e.g. D-serine or its precursor/analogue may act as a CTTNBP2 rescuer to recover defects caused by impairment in CTTNBP2 and is effective in treating ASD or ASD-like symptoms. It is also disclosed that a zinc ion source and/or a serine component can be administered in combination with a mixture of branched-chain amino acids (BCAAs) to provide an improved effect improve the treatment.

Therefore, in one aspect, the present invention provides a method for treating a symptom or disease characteristics associated with ASD or ASD-associated disorder in a subject in need thereof, comprising administering to the subject an effective amount of a zinc ion source and/or an effective amount of a serine component including D-serine or its precursor/analogue, optionally in combination with BCAAs comprising leucine, isoleucine and valine.

In some embodiments, the subject suffers from ASD.

In some embodiments, the ASD-associated disorder is neurofibromatosis type 1 (NF1).

In some embodiments, the symptom or disease characteristics to be treated by the method include impaired social interaction, hyperactivity and/or anxiolytic effect.

In some embodiments, the impaired social interaction includes deficits in social novelty preference (social memory) and/or reciprocal social interaction.

In some embodiments, the subject has a mutation in an endogenous gene encoding CTNBP2 and/or TBR1 and/or neurofibromin resulting a defect in dendritic spine formation.

In certain embodiments. the mutation in the endogenous gene encoding CTTNBP2 results in a modification at an amino acid position corresponding to amino acid position 42, 113, 121, 343, 354, 536 and/or 580 of the amino acid sequence set forth in SEQ ID NO: 1.

In some embodiments, a zinc ion source, a serine component or BCAAs as described herein is administered in an amount resulting in an increased level in the subject compared with its basal level for the subject.

In some embodiments, such increased level is maintained for over relatively long periods of times (e.g., days, weeks, months, years, or even for a lifetime) as long as no severe side effects or complications occur. In some embodiments, such increased level is maintained for about 1-10 days or more, e.g. 1 day, 2 days, 3 days, 4 days, 5 days, 6 days, 7 days, 8 days, 9 days, 10 days or more.

In some embodiments, the method according to the present invention further comprise measuring the basal level before administration, and then a zinc ion source, a serine component or BCAAs as described herein is administered in an amount sufficient to provide an increased level compared with the basal level.

In some embodiments, a zinc ion source and a serine component as described herein are administered in amounts to provide an improved effect to in treating the symptom or disease characteristics associated with ASD or ASD-associated disorder.

In some embodiments, a zinc ion source and a serine component in combination with BCAAs as described herein are administered in amounts to provide an improved effect to in treating the symptom or disease characteristics associated with ASD or ASD-associated disorder.

In some embodiments, the BCAA mixture includes leucine, isoleucine and valine in a weight ratio of about 2:1:1.

In some embodiments, a zinc ion source as described herein is administered in an amount of about 0.10 mg to about 1.50 mg/kg body weight per day; for example, about 0.10 mg to about 1.20 mg/kg body weight per day, about 0.20 mg to about 0.90 mg/kg body weight per day, or about 0.30 mg to about 0.70 mg/kg body weight per day.

In some embodiments, a serine component as described herein is administered in an amount of about 0.01 g to about 0.50 g/kg body weight per day; for example, about 0.01 g to about 0.30 g/kg body weight per day, about 0.01 g to about 0.25 g/kg body weight per day, or about 0.05 g to about 0.20 g/kg body weight per day.

In some embodiments, BCAAs as described herein are administered in an amount of about 0.01 g/kg to about 0.50 g/kg body weight per day; for example, about 0.01 g/kg to about 0.25 g/kg body weight per day, about 0.01 g/kg to about 0.10 g/kg body weight per day, or about 0.03 g/kg to about 0.08 g/kg body weight per day.

In some embodiments, a zinc ion source and/or a serine component and optional BCAAs as described herein are administered daily for a 1-10 day period e.g. 1-7 days, optionally at a proper time interval as needed e.g. about 24 hours between each period.

In some embodiments, a zinc ion source and/or a serine component and optional BCAAs as described herein are administered together in a composition or separately as a combination therapy.

Also provided is a combination, kit or composition for performing the method of treatment as described herein, comprising an effective amount of a zinc ion source and/or an effective amount of a serine component including D-serine or its precursor/analogue, optionally in combination with branched-chain amino acids (BCAAs) comprising leucine, isoleucine and valine.

In some embodiments, the composition is in the form of a pill, tablet, capsule, powder, lozenge, or gum, or liquid.

In some embodiments, the composition is in the form of a food or beverage or drinking water.

Further provided is use of a zinc ion source and/or a serine component and optional BCAAs as described herein for manufacturing a medicament for treating a symptom or disease characteristics associated with ASD or ASD-associated disorder or as a food supplement for ameliorating relevant symptoms in a subject in need thereof.

The present invention still provides an animal model for autistic spectrum disorder (ASD) which comprises a non-human mammal with disabled function of CTTNBP2. In certain embodiments, the animal model is a rodent (e.g. a mouse) lacking one or both wild type alleles of the CTTNBP2 gene or wherein the function of the CTTNBP2 protein of the rodent is impaired.

The present invention still further provides a method for identifying an ingredient effective in the treatment of ASD, wherein the method comprises (a) administering an agent to an animal model with disabled function of CTTNBP2, wherein the animal model lacks one or both wild type alleles of the CTTNBP2 gene or wherein the function of the CTTNBP2 protein of the animal model is impaired; and (b) determining if one or more symptom or disease characteristics associated with ASD in the animal model have become reduced in result of the administration of the agent.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A shows sequences and targeting information of Cttnbp2 knockout mice (lines 3-1 and 1-9) generated by a TALEN approach. The PvuII cutting site in Exon 3 of the Cttnbp2 gene was chosen for targeting. The positions of primers for genotyping are indicated. SEQ ID NOs: 7 and 8 are the nucleotide sequences of the TALEN recognition sites at 5' end and 3' end in Exon 3 of the Cttnbp2 gene, respectively. SEQ ID No: 9 is the original nucleotide sequences in the spacer (without treatment of TALEN). SEQ ID No: 10 is the nucleotide sequence in the spacer after treatment of TALEN where one nucleotide is deleted resulting frame-shift knock-out mutation (line no. 3-1). SEQ ID No: 11 is the nucleotide sequences in the spacer after treatment of TALEN where two nucleotides are deleted resulting frame-shift knock-out mutation (line no. 1-9). FIG. 1B shows immunoblotting of CTNBP2 using whole brain lysates prepared from a Cttnbp2−/− mouse and wild-type littermate. HSP90 was used as a loading control. FIG. 1C shows DAB staining using CTTNBP2 antibody in sagittal brain sections. Cttnbp2+/+ and Cttnbp2−/− mouse brains were compared. FIG. 1D shows CTTNBP2 expression in different brain areas. VCP was used as a loading control. OB, olfactory bulb; Stn, striatum; Ctx, cerebral cortex; Hc, hippocampus; Th, thalamus; Cb, cerebellum; Md, midbrain. Scale bar, 2 mm. FIG. 1E shows open-field test. Total moving distance and the ratio of time spent at center (Tcent) to time spent at corners (Tcom) are shown. FIG. 1E shows elevated-plus maze. OP, open arm; CL, closed arm. Three different comparisons are presented; namely within the same genotype, within open arms and within closed arms. FIG. 1E shows reciprocal social interaction test (RSI). FIG. 1E shows sociability assessed by three-chamber test. FIG. 1I shows novelty preference assessed by three-chamber test. Heat maps of movement paths of mice (top), actual interaction times, the difference in interaction time between the left and right cages, and the preference index are shown. Ob, object; S1, stranger 1; S2, stranger 2. Data represent mean+/−SEM. Each dot represents the data of one animal. One-way ANOVA with Bonferroni multiple comparison test or Kruskal-Wallis test with Dunn's multiple comparison test was used to compare groups among three different genotypes; paired t-test or Wilcoxon matched-pairs signed rank test was used to compare differences in the same group of animals. *, $p<0.05$; , $p<0.01$; *, $p<0.001$.

FIG. 2A shows summary of ASD-associated mutations in the mouse Cttnbp2 gene and corresponding human CTTNBP2 gene mutations are indicated in parentheses. Schematic domain structure of CTTNBP2 is also shown. N, N-terminal region; CC, coiled-coil domain; Mid, middle region; P-rich, proline-rich domain. FIG. 2B shows representative image of dendrites of cultured hippocampal neurons that express WT or ASD-associated CTTNBP2 mutant proteins (viewed in red). Dendritic morphology was outlined by GFP-actin (visualized in green). Scale bar, 5 μm. FIG. 2C shows quantification of dendritic spine density. Sample size n represents the number of examined dendrites for each group. The results were collected from three independent experiments and analyzed using Kruskal-Wallis test with Dunn's multiple comparison test compared with the wild-type (WT) group. Data represents mean+/−SEM. Each dot represents the data of one dendrite.

FIGS. 3A to 3J show that M120I and R533* knockin mice exhibit reduced social interaction. FIGS. 3A to 3E show the behavioral analyses in M120I mice. FIGS. 3F to 3J show the behavioral analyses in R553 mice. FIG. 3A and FIG. 3F show the results of the open filed assay in M120Imice and R553 mice, respectively. FIG. 3B and FIG. 3G show the results of the elevated plus maze assay in M120Imice and R553 mice, respectively. FIG. 3C and FIG. 3H show the results of the reciprocal social interaction assay in M120Imice and R553 mice, respectively. FIG. 3D and FIG. 3I show the results of sociability assay in M120Imice and R553 mice, respectively. FIG. 3E and FIG. 3J show the results of novelty preference assay in M120Imice and R553 mice, respectively. The time spent in social interaction was quantified and analyzed using Mann-Whitney test. Sociability was assayed in Three-chamber test. Novelty preference was assayed in three-chamber test. Heat maps of movement paths of mice, actual interaction time, the difference in interaction time between the left and right chambers, and preference index are shown. A paired t-test or Wilcoxon matched-pairs signed rank test was used to compare total interaction times for the object (Ob) and stranger 1 (S1) or for S1 and stranger 2 (S2). To compare interaction times or preference indexes, an unpaired t-test or Mann Whitney test was used. Data represents mean+/−SEM. Each dot represents the data of one animal. *, $p<0.05$; , $p<0.01$; *, $p<0.001$; ns, not significant.

FIG. 4A shows representative images of C-FOS$^+$ cells at CA regions of hippocampi. Two hr after reciprocal social interaction, mice were subjected to C-FOS staining. FIG. 4B, FIG. 4C and FIG. 4D show quantification of C-FOS$^+$ cells across multiple brain areas of (FIG. 4B) Cttnbp2+/+, +/− and −/− mice, (FIG. 4C) M120I mice and wild-type littermates, and (FIG. 4D) R533* mice and wild-type littermates after social stimuli, respectively. Numbers of examined animals are indicated in columns. dCA1, dorsal CA1; dCA2, dorsal CA2; dCA3, dorsal CA3; dDG, dorsal dentate gyrus; RSP, retrosplenial cortex; SOP, somatosensory cortex; BLA, basolateral amygdala; MO, motor cortex; ACAd, anterior cingulate cortex; PL, prelimbic; ILA, infralimbic; PIR2, piriform cortex; CP, caudoputamen; ACB, nucleus accumbens; vCA1, ventral CA1; vCA3, ventral CA3. One-way ANOVA with Dunnett's multiple comparison test compared with wild-type; unpaired t-test. Data represent mean plus SEM. Each dot represents the result of one animal. The numbers indicate the sample size of each group. *, $p<0.05$; , $p<0.01$; *, $p<0.001$. Scale bar, 200 μm.

FIG. 5A illustrates dendritic spine characterization. One of the first branches (located within 30-60 m distant from the soma) of an apical dendrite of a CA neuron was subjected to quantification for the density, length and width of dendritic spines based on Thy1-eYFP signals. FIG. 5B shows the results for Cttnbp2+/+, +/− and −/− mice. FIG. 5C shows the results for M120I mutant and wild-type (+/+) mice. FIG. 5D shows the results for R533* mutant and wild-type mice. In (FIG. 5B, FIG. 5C and FIG. 5D), data were collected from (FIG. 5B) N=3 (+/+), 3 (+/−), 3 (−/−); (FIG. 5C) N=4 (+/+), 4 (M120I); or (FIG. 5D) N=3 (+/+), 3 (R533*) animals. Each dot represents one dendrite and 10 dendrites were randomly collected from each animal. Data represent mean+/−SEM. Each dot represents the result of one neuron. FIG. 5E shows representative TEM images of hippocampal synapses at the regions of dentate gyrus (DG), CA3 and CA1. FIG. 5F shows quantification of PSD length, thickness, the number of synaptic vesicles (#SV), and the ratio of #SV to the length of PSD. Data were collected from N=5 (+/+), 4 (+/−), or 5 (−/−) animals. Data represents mean+/−SEM. (FIG. 5B, FIG. 5F) One-way ANOVA with Dunnett's multiple comparison post test or Kruskal-Wallis test with Dunn's multiple comparison test. (FIG. 5C, FIG. 5D) Unpaired t-test or Mann-Whitney test. *, p<0.05; , p<0.01; *, p<0.001. Scale bar, (FIG. 5A) right, 20 μm; left, 5 μm; (FIG. 5B)-(FIG. 5D) 5 μm; (FIG. 5E) 2.5 μm.

FIGS. 6A to 6E show that Cttnbp2 deficiency alters expression of synaptic proteins. FIG. 6A shows volcano plot of differentially expressed proteins in Cttnbp2−/− forebrains. Synaptosomal fractions of Cttnbp2−/− and wild-type mice were purified and compared. Blue dots represent 61 downregulated proteins; red dots indicate 57 upregulated proteins. FIG. 6B shows that differentially expressed synaptic proteins in Cttnbp2−/− forebrains were analyzed using protein association network analysis (STRING, httus://strine-db.org/). FIG. 6C shows gene ontology (GO) of both down- and up-regulated synaptic proteins. Top ten GO for biological process, molecular function and pathways are listed. FIG. 6D shows twenty differentially expressed synaptic proteins are ASD-associated. These proteins are indicated on enlarged Volcano plots. FIG. 6E shows list of SFARI and/or SPARK genes regulated by CTTNBP2 and their known molecular functions. The numbers indicate their SFARIscores (htts://gene.sfari.org/database/human-gene/).

FIG. 7A and FIG. 7B show immunoblotting of differentially expressed proteins using (FIG. 7A) synaptosomal fractions and (FIG. 7B) total lysates purified from four wild-type and four Cttnbp2−/− forebrains. Quantification results are also shown in lower panels. FIG. 7C shows co-immunoprecipitation using CTTNBP2 antibody. Cttnbp2−/− lysates were used as a negative control to demonstrate specificity. FIG. 7D shows immunoblotting of glutamate receptors using the same synaptosomal fractions and total lysates as used in (FIG. 7A and FIG. 7B).

FIG. 7E shows the quantification results of (D). Each blot was stripped and reprobed with two to five antibodies, including HSP90 as loading control. To save space, only one representative blot of HSP90 is shown for each column. Data represent mean+/−SEM. Relative expression levels were normalized with HSP90. Unpaired t-test. *, p<0.05; , p<0.01; *, p<0.001.

FIG. 8A shows zinc supplementation for 7 days increases zinc concentration in Cttnbp2−/− mouse brains. Unpaired t-test was used. *, p<0.05. FIG. 8B shows immunoblotting of differentially expressed synaptic proteins and glutamate receptors after zinc supplementation for 7 days. Cttnbp2−/− mice with 40 ppm zinc in drinking water were compared to Cttnbp2−/− mice that drank regular water. The results of quantification are also shown. HSP90 was used as the loading control. Six mice were used for each group. Data represent mean+/−SEM. Unpaired t-test. FIG. 8C shows schematic diagram of zinc supplementation and three reciprocal social interaction tests (RSI) performed at weeks 9, 10 and 11 of mouse age. Zinc supplementation was carried out between the first and second RSI tests. FIG. 8D and FIG. 8E show ameliorated social behavior of zinc-supplemented mice in RSI tests. Lines link the results of the same individual mouse for the three tests. (FIG. 8D) Cttnbp2−/− mice. (FIG. 8E) CTTNBP2 R533* mice.

FIG. 9A shows schematic diagram of D-cycloserine (DCS) administration and the two RSI tests. Mice were subjected to open field at 8 weeks old to habituate them to handling. Following isolation and habituation to intraperitoneal injection, saline was injected into the mice 30 min prior to the first RSI at week 10. One day later, D-cycloserine solution (DCS) was injected into mice 30 min prior to the second RSI. FIG. 9B, FIG. 9C and FIG. 9D show reciprocal social interaction test of (FIG. 9B) Cttnbp2−/− mice, (FIG. 9C) M120I mutant mice, and (FIG. 9D) R533* mutant mice. Wild-type littermates were always included as controls for each mutant. Paired t-tests or Wilcoxon matched-pairs signed rank test were used for comparisons of the same genotypes in different tests. To compare wild-type and Cttnbp2−/− mice, unpaired t-tests or Mann Whitney test were used. *, p<0.05; , p<0.01; *, p<0.001.

DETAILED DESCRIPTION OF THE INVENTION

Figure 1A:
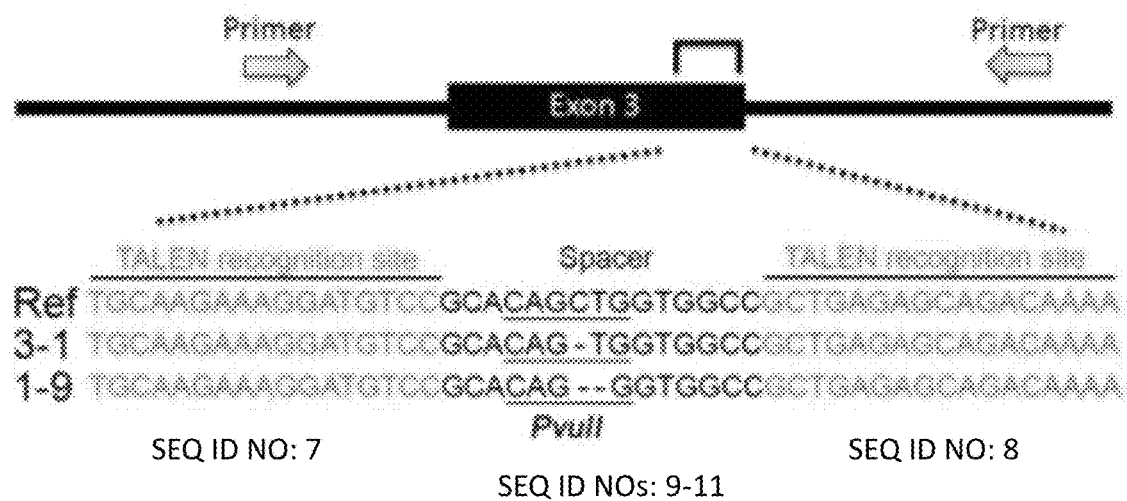
FIGS. 1A to 1I show that Cttnbp2 knockout mice exhibit social deficits.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

The term "about" as used herein means plus or minus 5% of the numerical value of the number with which it is being used.

As used herein, "corresponding to," refers to a residue at the enumerated position in a protein or peptide, or a residue that is analogous, homologous, or equivalent to an enumerated residue in a protein or peptide.

The term "autism spectrum disorder (ASD)" as known in this art refers to a group of developmental brain disorders, having a wide range of symptoms characterized by social deficits and communication difficulties, stereotyped or repetitive behaviors and interests, and in some cases, cognitive delays. It includes autism and Asperger syndrome. The expression of symptoms is variable, ranging from mild to severe and usually with other psychiatric and medical conditions. Typical symptom or disease characteristics associated with ASD include impaired social interaction, hyperactivity and anxiety. In particular, impaired social interaction incudes deficits in social novelty preference (social memory) and/or reciprocal social interaction.

Specifically, according to the Diagnostic and Statistical Manual of Mental Disorders, Fifth Edition (DSM-5), diagnostic criteria for ASD include the following:

A. Persistent deficits in social communication and social interaction across multiple contexts, as manifested by the following, currently or by history (examples are illustrative, not exhaustive):
  1. Deficits in social-emotional reciprocity, ranging, for example, from abnormal social approach and failure of normal back-and-forth conversation; to reduced sharing of interests, emotions, or affect; to failure to initiate or respond to social interactions;
  2. Deficits in nonverbal communicative behaviors used for social interaction, ranging, for example, from poorly integrated verbal and nonverbal communication; to abnormalities in eye contact and body language or deficits in understanding and use of gestures; to a total lack of facial expressions and nonverbal communication; and
  3. Deficits in developing, maintaining, and understanding relationships, ranging, for example, from difficulties adjusting behavior to suit various social contexts; to difficulties in sharing imaginative play or in making friends; to absence of interest in peers;

B. Restricted, repetitive patterns of behavior, interests, or activities, as manifested by at least two of the following, currently or by history (examples are illustrative, not exhaustive):
  1. Stereotyped or repetitive motor movements, use of objects, or speech (e.g., simple motor stereotypes, lining up toys or flipping objects, echolalia, idiosyncratic phrases);
  2. Insistence on sameness, inflexible adherence to routines, or ritualized patterns of verbal or nonverbal behavior (e.g., extreme distress at small changes, difficulties with transitions, rigid thinking patterns, greeting rituals, need to take same route or eat same food every day);
  3. Highly restricted, fixated interests that are abnormal in intensity or focus (e.g., strong attachment to or preoccupation with unusual objects, excessively circumscribed or perseverative interests); and
  4. Hyper- or hyporeactivity to sensory input or unusual interest in sensory aspects of the environment (e.g., apparent indifference to pain/temperature, adverse response to specific sounds or textures, excessive smelling or touching of objects, visual fascination with lights or movement); and C. Symptoms must be present in the early developmental period (but may not become fully manifest until social demands exceed limited capacities, or may be masked by learned strategies in later life); and D. Symptoms cause clinically significant impairment in social, occupational, or other important areas of current functioning.

ASD may be can be part of some known genetic syndromes. They are usually associated with malformations and/or dysmorphic features (called syndromic ASD) which are different from most ASD cases, called non-syndromic ASD (idiopathic or primary ASD). Such genetic or genomic disorders can be said to be ASD-associated disorders. Typical examples include fragile X syndrome, tuberous sclerosis, neurofibromatosis type 1 (NF1), Angelman, Cornelia de Lange and Down syndrome.

Cortactin-binding protein 2 (CTTNBP2) is known as a critical regulator of actin and microtubule cytoskeletons, thereby controlling neuronal morphology and activity. CTTNBP2 controls the mobility of cortactin at dendritic spines and regulates dendritic spine formation and maintenance in mature hippocampal neurons, and Cttnbp2 knockdown reduces the density and size of dendritic spines, as well as the frequency of miniature excitatory postsynaptic currents [9]. Several mutations of CTTNBP2 have been reported in ASD cases e.g. mutations at amino acid positions 42, 113, 121, 343, 354, 536 and/or 580 as set forth in the amino acid sequence set forth in SEQ ID NO: 1 (the above respective amino acid position in SEQ ID NO: 1 for human gene corresponds to the amino acid position 42, 112, 120, 342, 353, 533 and 570 in SEQ ID NO: 3 for mouse gene). In certain embodiments, the CTTNBP2 mutant may include one or more point mutation selected from the group consisting of R42W, A113T, M121I, G343R, P354A, R536* and D580Y.

NF1 gene encodes neurofibromin, a Ras-GTPase-activating protein (Ras-GAP) and is known to inhibit Ras signaling in astrocytes. Impairment in neurofibromin results in a dendritic spine defect and causes neurofibromatosis type 1 (NF1). NF1 is characterized by multiple cafe au lait spots, axillary and inguinal freckling, multiple discrete cutaneous neurofibromas. Children with NF1 often experience features associated with ASD e.g. deficits of cognition and of social and emotional development, and findings indicate that high prevalence of ASD in NF1.

TBR1 gene encodes a brain-specific T-box transcription factor, known as a causative gene in ASD. It is a critical factor for the telencephalon development in mammals. Tbr1 deficiency influences axonal projection of basolateral amygdala and impairs formation of anterior commissure in both human and mice [47-49]. It also modulates expression of its downstreaming genes (such as Grin2b) to result in excitation/inhibition imbalance [47]. Tbr1+/− mice exhibit several typical autism-like behaviors, including reduced social interaction, impaired vocal communication, cognitive inflexibility and abnormal olfactory aensation [47, 50]. D-cycloserine or clioquinol (a Zn chelator and ionophore) ameliorate the behavioral defects and improve autism-like behaviors of Tbr1+/− mice [49, 50, 51].

The term "treating" as used herein refers to the application or administration of a composition including one or more active agents to a subject afflicted with a disorder, a symptom or conditions of the disorder, or a progression or predisposition of the disorder, with the purpose to cure, heal, alleviate, relieve, alter, remedy, ameliorate, improve, or affect the disorder, the symptoms or conditions of the disorder, the disabilities induced by the disorder, or the progression or predisposition of the disorder.

The term "effective amount" used herein refers to the amount of an active ingredient to confer a desired biological effect in a treated subject. For example, an effective amount for treating a symptom or disease characteristics associated with autistic spectrum disorder (ASD) or ASD-associated disorder can prohibit, improve, alleviate or reduce one or more ASD symptoms or conditions as described herein, particularly impaired social interaction, hyperactivity and/or anxiolytic effect, more particularly social novelty preference (social memory) and/or reciprocal social interaction. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

The present invention provides a new approach for ASD or ASD-like symptom. According to the present invention, a zinc ion source and/or a serine component e.g. D-serine or its precursor/analogue is administered to a subject in need for treating a symptom or disease characteristics associated with ASD or ASD-associated disorder.

The term "zinc ion source" as used herein includes any zinc compound that provides zinc ions or releases zinc ions upon ingestion in the body. The zinc ion source can be selected to be in a form acceptable for inclusion in an animal food or for oral administration or for any other suitable administration. Zinc ion sources include but are not limited to zinc salts. Zinc salts useful herein include but are not limited to zinc acetate, zinc citrate, zinc carbonate, zinc gluconate, zinc ascorbate, zinc sulfate, and sodium zinc citrate.

The term "a serine component" as used herein includes D-serine or its precursor (e.g. L-serine)/analogue (e.g. D-cycloserine (DCS)). D-serine is produced through isomerization of L-serine (its enantiomer or precursor) by serine racemase (Srr), in neurons or astrocytes. D-cycloserine (DCS), (4R)-4-amino-1,2-oxazolidin-3-one, is an analog of D-serine and is a broad-spectrum antibiotic.

In particular, a zinc ion source as described herein can be administered to a subject in need in an amount sufficient to increase zinc ion level in the subject compared with a corresponding basal level for the subject, and/or a serine component is administered to a subject in need in an amount sufficient to increase serine component level in the subject compared with a corresponding basal level for the subject.

The term "a basal level" as used herein can mean a level determined prior to or at the beginning of the treatment or therapy, or a level in normal individuals or suitable controls.

The term "increase" or "enhance" as used herein can refer to an increase by about 2% or more, 5% or more, 10% or more, 15% or more in view of a basal level.

Specifically, an increased zinc ion level and/or an increased serine component is maintained for a period of time sufficient to improve ASD symptoms. In some embodiments, such increased level is maintained over relatively long periods of times (e.g., days, weeks, months, years, or even for a lifetime) as long as no severe side effects or complications occur. In some embodiments, such increased level is maintained for about 1-10 days or more, e.g. 1 day, 2 days, 3 days, 4 days, 5 days, 6 days, 7 days, 8 days, 9 days, 10 days or more. In some embodiments, such long periods of times does not include significant interruptions which make the increased level of zinc ion level and/or serine component unsustainable. In some embodiments, each period is given at a proper time interval e.g. about 24 hours between each period.

The present invention provide combination therapy.

In some embodiments, a zinc ion source and/or a serine component as described herein can be administered in combination with branched-chain amino acids (BCAAs).

Branched chain amino acids, as used herein, can have aliphatic side chains with a branch carbon atom that is bound to two or more other atoms. The other atoms may be carbon atoms. Examples of branched chain amino acids include leucine, isoleucine, and valine. In some embodiments, BCAAs includes leucine, isoleucine and valine in a weight ratio of about 2:1:1. Specifically, BCAAs are administered to a subject in need in an amount sufficient to increase BCAAs level in the subject compared with a corresponding basal level for the subject. In some embodiments, such increased level is maintained over relatively long periods of times (e.g., days, weeks, months, years, or even for a lifetime) as long as no severe side effects or complications occur. In some embodiments, such increased level is maintained for about 1-10 days or more, e.g. 1 day, 2 days, 3 days, 4 days, 5 days, 6 days, 7 days, 8 days, 9 days, 10 days or more. In some embodiments, such long periods of times does not include significant interruptions which make the increased level of zinc ion level and/or serine component unsustainable. In some embodiments, each period is given at a proper time interval e.g. about 24 hours between each period.

In some other embodiments, a zinc ion source is administered in combination with a serine component. In some embodiments, a zinc ion source and a serine component are further administered in combination with BCAAs.

Preferably, such combination is effective to provide an improved or synergistic effect in treating ASD symptom or disease characteristics. In certain embodiments, a zinc ion source and a serine component together with BCAAs as described herein provides a synergistic effect when combined, making these ingredients more effective than either one alone.

In addition, the method of the invention may comprise conducting a measuring step prior to the administration of a zinc ion source and/or a serine component, optionally BCAAs, in order to determine a corresponding basal level, such that the administration can be carried out with a proper amount sufficient to provide an increased level in the subject upon administration compared with the basal level. The method of the invention may comprise a later measuring step which is carried out after the administration in order to determine if an increased level of a zinc ion source and/or a serine component, optionally BCAAs, is achieved or needs to be adjusted.

In some embodiments, a zinc ion source as described herein is administered in an amount of about 0.10 mg to about 1.50 mg/kg body weight per day. In certain embodiments, a zinc ion source is administered in an amount of about 0.10 mg to about 1.20 mg/kg body weight per day. In certain embodiments, a zinc ion source is administered in an amount of about 0.20 mg to about 0.90 mg/kg body weight per day. In certain embodiments, a zinc ion source is administered in an amount of about 0.30 mg to about 0.70 mg/kg body weight per day.

In some embodiments, a serine component as described herein is administered in an amount of about 0.01 g to about 0.50 g/kg body weight per day. In certain embodiments, a serine component is administered in an amount of about 0.01 g to about 0.30 g/kg body weight per day. In certain embodiments, a serine component is administered in an amount of about 0.01 g to about 0.25 g/kg body weight per day. In certain embodiments, a serine component is administered in an amount of about 0.05 g to about 0.20 g/kg body weight per day.

In some embodiments, BCAAs as described herein are administered in an amount of about 0.01 g/kg to about 0.50 g/kg body weight per day. In certain embodiments, BCAAs are administered in an amount of about 0.01 g/kg to about 0.25 g/kg body weight per day. In certain embodiments, BCAAs are administered in an amount of about 0.01 g/kg to about 0.10 g/kg body weight per day. In certain embodiments, BCAAs are administered in an amount of about 0.03 g/kg to about 0.08 g/kg body weight per day.

In some embodiments, a zinc ion source and/or a serine component and optional BCAAs as described herein are administered daily for a 1-10 day period or more, e.g. 1 day, 2 days, 3 days, 4 days, 5 days, 6 days, 7 days, 8 days, 9 days, 10 days or more, optionally at a proper time interval e.g. about 24 hours between each period.

The active ingredients of the invention can be prepared into suitable pharmaceutical preparations (e.g., together in a composition) or separately to be used in a combination therapy (e.g. a kit or package).

According to the present invention, an effective amount of the active ingredient(s) may be formulated with a physiologically acceptable carrier into a composition of an appropriate form for the purpose of delivery and absorption. The composition of the present invention particularly comprises about 0.1% by weight to about 100% by weight of the active ingredient, wherein the percentage by weight is calculated based on the weight of the whole composition. In some embodiments, the composition of the present invention can be a pharmaceutical composition or medicament for treatment. In some embodiments, the composition of the present invention can be a food product or supplement.

As used herein, "physiologically acceptable" means that the carrier is compatible with the active ingredient in the composition, and preferably can stabilize said active ingredient and is safe to the receiving individual. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of the composition may be tablets, pills, powder, lozenges, packets, troches, elixers, suspensions, lotions, solutions, syrups, soft and hard gelatin capsules, suppositories, sterilized injection fluid, and packaged powder. In some certain embodiments, the form of the composition may be a pill, tablet, capsule, powder, lozenge, or gum, or liquid.

The composition of the present invention may be delivered via a suitable physiologically acceptable route, such as oral, parenteral (such as intramuscular, intravenous, subcutaneous, and intraperitoneal), transdermal, suppository, and intranasal methods.

The ingredients as described herein can be included in a kit where the ingredients are present separately to be used in a combination therapy.

Therefore, the present invention also provide a kit comprising (i) a zinc ion source, and/or (ii) a serine component including D-serine or its precursor/analogue, optionally (iii) BCAAs. The kit can be a package which houses a container or containers that comprises the ingredients as described herein. In particular, a kit can comprise instructions for simultaneous, separate or sequential use. A kit can contain a single dosage form or it can contain separate dosage forms, i. e. one for each therapeutic agent to be administered. The kit can additionally include other materials desirable from a commercial and user needs, including, without limitation, buffers, diluents, filters, needles, syringes, and package inserts with instructions for performing methods disclosed herein.

In some embodiments, a zinc ion source and a serine component together with BCAAs as described herein are formulated into a composition. In certain embodiments, a zinc ion source is present in the composition in an amount of about 10 to about 30 ppm (such as 15 to 25 ppm e.g. 20 ppm); a serine component is present in the composition in an amount of about 0.25% (w/w) to about 2% (w/w) (e.g. 0.5% (w/w) to 1.5% (w/w) e.g. 1% (w/w)); and BCAAs are present in the composition in an amount of about 0.1% (w/w) to about 1% (w/w) (such as 0.20% (w/w) to 0.5% (w/w) e.g. 0.225% (w/w) to 0.45% (w/w)) wherein the % (w/w) values are based on the total weight of the composition.

In general, the subject suitable to receive the method of the present invention includes, but is not limited to, a human, a mouse and other animal subject. As a preferred embodiment, the subject is a human. In certain embodiments, the subject is characterized by disabled function of one or more ASD relevant genes, such as NF1 gene, CTTNBP2 gene and TBR1 gene. Disabled function of a gene can include that the subject lacks one or both of the wild type alleles of the ASD relevant genes or mutation occur in one or both of the alleles such that the expression or the function of the corresponding proteins are impaired, for example.

In some embodiments, the subject has a point mutation in the CTTNBP2 gene that results in a change at an amino acid position corresponding to amino acid position 42, 113, 121, 343, 354, 536 and/or 580 of the amino acid sequence set forth in SEQ ID NO: 1.

In the present invention, it is first found that CTTNBP2 gene plays an important role in regulating the distribution of ASD associated proteins to ASD-like symptoms, and animals with abnormal CTTNBP2 gene can mimic the situations in ASD patients.

Therefore, the present invention provides an animal model for ASD which comprises a rodent without a functional CTNBP2 gene or with a CTNBP2 protein of impaired properties. The animal models of the invention can include mutations in one or both alleles of the CTTNBP2 gene in the genome of the transgenic animal, and the mutation(s) can result in full or partial inactivation of the gene.

The animal models of the invention can be generated using a genetically engineered approach known in the art. In some embodiment, animal models of the invention can be generated by a method comprising the steps of (i) introducing one or more mutations into an allele of one or more genes (e.g. CTNBP2 gene) associated with a disease or condition as described herein (e.g. ASD or ASD-like symptoms) in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female. The animals are non-human mammals such as rodents e.g. mice or rats, and primates such as chimpanzees, monkeys, and gorillas. In some embodiments, the donor cell includes one or more mutations in one allele of a gene, and the method is carried out to introduce one or more mutations into the other allele. In some embodiments, the method involves breeding an animal that is born from the surrogate female to obtain a mutant animal that exhibits symptoms ASD. The animal model of the present invention exhibit distinctive properties and expressions for ASD, including reduced social interaction, impaired vocal communication and cognitive inflexibility.

The present invention also involves a method for identification of active agents useful for the treatment of ASD or ASD-like symptoms, which comprises administering one or more agents under testing to an ASD animal model as described herein lacking a functional CTTNBP2 protein or its function is disturbed, and determining if a symptom or disease characteristics associated with ASD has become reduced in result of the administration of the agent.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Synaptic dysfunction and dysregulation are critical features of autism spectrum disorders. Among various autism-associated genes, cortactin binding protein 2 (CTTNBP2) is a cytoskeleton regulator predominantly expressed in neurons and highly enriched at synapses. Previous studies have indicated that CTTNBP2 regulates synaptic distribution of cortactin and controls dendritic spine formation in cultured neurons. Here, we generated Cttnbp2 knockout mice and two knockin mouse lines carrying autism-associated mutations to investigate the physiological relevance of CTTNBP2. All our mutant mice exhibited impaired dendritic spine formation, reduced neuronal activation and abnormal social interaction, suggesting a critical role of Cttnbp2 in controlling neuronal morphology and function. Combining proteomic and immunoblotting analyses, we further found that CTTNBP2 regulates the synaptic distribution of at least 118 proteins, including SHANKs, NRXN1, NMDAR and another 17 autism-causative or-associated proteins. Since zinc binding and regulation is a feature shared by some CTTNBP2-regulated proteins, we performed dietary zinc supplementation to investigate its ameliorating effect. We found that zinc supplementation rescued synaptic expression of NMDAR, SHANKs and other CTTNBP2-regulated proteins and improved social interaction of Cttnbp2 mutant mice to levels comparable to wild-type littermates. Apart from zinc supplementation, D-cycloserine, an NMDAR coagonist, also ameliorated social behaviors of our Cttnbp2 mutant mice. Our study suggests that CTTNBP2 functions as a master regulator to control synaptic expression of a set of zinc-regulated autism-associated genes. Cttnbp2 deficiency and mutations result in impaired NMDAR function and signaling, dendritic spine formation and social interaction, which could be ameliorated by zinc supplementation and D-cycloserine treatment.

1. Material and Methods
1.1 Animal Experiments

All animal experiments were performed with the approval of the Academia Sinica Institutional Animal Care and Utilization Committee (Protocol #12-10-414 and 11-12-294), and in strict accordance with its guidelines and those of the Council of Agriculture Guidebook for the Care and Use of Laboratory Animals, Taiwan. Principles of laboratory animal care (NIH publication No. 86-23, revised 1985) were followed. Animal handling was conducted according to the guidelines of the Council of Agriculture Guidebook for the Care and Use of Laboratory Animals. All animals were housed and bred in the animal facility of the Institution of Molecular Biology, Academia Sinica, under controlled humidity and temperature and a 12 hr light/dark cycle (light off at 20:00). Animals accessed water and food (#5K54, LabDiet) ad libitum. To mimic the situation in ASD patients, we used only heterozygous ASD knockin mutant mice, namely M120I/+ and 533*/+, in this report to assess the effect of ASD-associated mutations in mice. All genetically modified mice had been backcrossed to WT C57BL/6 mice for more than 6 generations to minimize the off target effect. Adult male mice (2-3 months old) were used for behavior analyses in order to avoid the variation caused by the estrus cycle in females. Littermates (2-6 mice) comprised different genotypes housed together without selection for behavioral assays. Before behavior experiments, the mice were acclimatized in the experiment room for at least one week, and relabeled for blind analysis.

1.2 Behavior Analyses
1.2.1 Open Field

The open field test was conducted as described [43, 44] to monitor locomotor activity and anxiety. In brief, the apparatus was a transparent acrylic box (40×40×30 cm). A single mouse was placed in the center of the box and allowed to freely explore the arena. The whole experiment was recorded for 30 min by videotaping from above the box. The central zone of the box was defined by a square (20×20 cm) equidistant from the walls. The size of the central zone is equal to the sum of the four corners. The Smart Video Tracking System (Panlab) was used to track the movement of the mice. Total moving distance indicates locomotor activity, and the ratio of time spent in the center to that in the corners indicates the degree of anxiety.

1.2.2 Elevated Plus Maze

A plus maze consists of two open arms and two closed arms (30×5 cm) extending from a small central platform (5×5 cm). The maze was elevated from the floor to a height of 45.5 cm. Animals were individually placed at the center of the platform and allowed to freely explore the maze for 10 min. The movement of the mice was recorded and analyzed using the Smart Video Tracking System (Panlab). The percentages of time spent in open arms and closed arms were assessed, with longer time spent in the closed arms indicating anxious behavior.

1.2.3 Reciprocal Social Interaction (RSI)

Before RSI, mice were individually isolated for at least a week. For the experiment, an unfamiliar adult mouse was put into the home cage of the test mouse for 10 min. The lid of the cage was removed during the entire session. Mouse behaviors were recorded by videotaping from above. The total time a test mouse spent interacting with and gently sniffing the unfamiliar mouse was manually recorded. Aggressive behavior was not assessed.

1.2.4 Three-Chambered Social Interaction

The apparatus and procedure for this experiment are described in previous reports [36, 43, 44]. Briefly, the apparatus of this test was a rectangular transparent plastic box (17.5×41.4×22 cm), with two dividing walls that partitioned the chamber into three equal parts. Each dividing wall had a sliding door that controlled mouse access to different chambers. Two cylindrical wired cages (10.5 cm in diameter and 11 cm in height) were placed in the left and right chambers. The entire experiment consisted of three sessions. For all three sessions, the test mouse was originally placed in the central chamber and the two sliding doors were then simultaneously opened to allow the mouse to freely explore the three chambers. During the first habituation session, both cylindrical wired cages were empty and the test mouse had 10 min to freely explore the entire apparatus. In the second session (to test sociability), a single inanimate object was placed in one cage and an unfamiliar mouse (stranger 1, S1) was put in the other cage. The test mouse was allowed to freely explore and interact with both the object and S1 for 10 min. In the last session (for social novelty preference), the object was replaced by another unfamiliar mouse (stranger 2, S2). The test mouse could freely explore and interact with S1 (familiar mouse) and S2 (novel stranger) for 10 min. The movement and sniffing behaviors of mice were recorded by videotaping. Social interaction was defined by sniffing toward the cages. The value of $(T_{S1}-T_{Ob})/(T_{S1}+T_{Ob})$ indicated the preference index of sociability. The index for novelty preference was defined as $(T_{S2}-T_{S1})/(T_{S2}+T_{S1})$. $T_{Ob}$ indicates the interaction time with the object, $T_{S1}$ represents the interaction time with S1, and $T_{S2}$ represents the interaction time with S2.

1.3 Preparation and Transfection of Cultured Primary Hippocampal Neurons

Primary hippocampal culture was performed as described [9, 12]. Briefly, embryonic day E18.5 hippocampi were carefully collected and digested with papain [0.6 mg/ml papain, 0.5 mM EDTA, 1.5 mM $CaCl_2$), 0.06% DNase I, 0.2 mg/ml cysteine] at 37° C. for 25 min. The papain buffer was removed and replaced with HBSS buffer. Cells were dissociated by gentle pipetting and collected by centrifugation at 900 rpm for 5 min. Cell pellets were re-suspended and cell number was determined. We seeded $2\times10^5$ cells/well of a 12-well plate on a polylysine-coated glass coverslip. Calcium phosphate precipitation was used to transfect the plasmid into cultured primary hippocampal neurons. Five μg plasmid DNA for each well in a 12-well culture plate was added into 0.25 M $CaCl_2$) solution for transfection [45].

1.4 Immunostaining

For DAB staining, 50-μm-thick brain sections were treated with freshly prepared 1% $H_2O_2$ in Tris-Cl buffer, pH 7.6, for 30 min. After washing, brain sections were permeabilized with 0.05% Tween-20 in PBS for 15 min and blocked with TNB buffer (0.5% blocking reagent—(TSA Fluorescein System Kit, No. 1715186, Perkin Elmer—) in PBS) for 1 hr. CTNBP2 antibody [9] was added into TNB buffer and incubated with brain sections overnight at 4° C. After washing with wash buffer (0.05% Tween-20 in PBS), brain sections were then incubated with biotinylated goat anti-rabbit IgG secondary antibody (1/200, vectastain, Vector Laboratories) in TNB buffer for 2 hr and developed using Vectastain Elite ABC Kit (Vector Laboratories) based on the manufacturer's instructions. For immunofluorescence staining, $H_2O_2$ treatment was skipped and the secondary antibodies conjugated with Alexa Fluor-488, -555, and/or -647 (Invitrogen) were incubated with brain sections for 2 hr.

1.5 Microscopy and Quantification

Figure 5A:
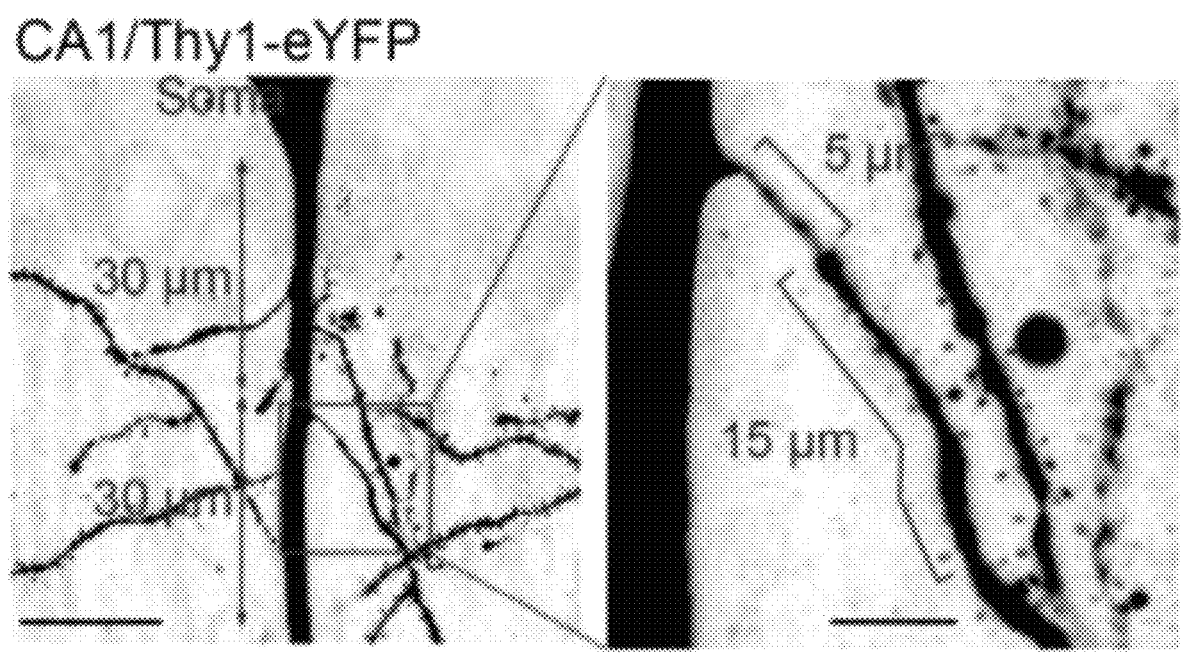
FIGS. 5A to 5F show that Cttnbp2 deficiency alters dendritic spines and postsynaptic density in brains.

True color images were acquired using an upright microscope (Microscope Axio Imager.M2, Carl Zeiss) equipped with a OX/NA 1.4 oil (Plan-Apochromat; Carl Zeiss) objective lens, an EMCCD camera Rolera EM-C2 (QImaging, Surrey, BC), and Zen 2011 program (Carl Zeiss) acquisition software. Shading correction and white balance was performed to correct the signal. For DAB staining and cresyl violet staining, the images were tiled up to get the entire view of the sections. Fluorescence images were acquired using a confocal microscope (LSM700; Carl Zeiss, Oberkochen, Germany) equipped with a 63X/NA 1.4 oil (Plan-Apochromat; Carl Zeiss) objective lens and Zen 2009 (Carl Zeiss) acquisition software. To capture images of spine morphology within the branches of CA1 apical dendrites, we employed the "Region" function in Zen 2009 (Carl Zeiss). All images were maximum-projected by multiple z-stacks with 0.2 μm intervals. To quantify the density of C-FOS$^+$ cells, images were imported to ImageJ (NIH) and converted into 8-bit images. Background was gated by threshold subtraction. Particles with signal intensities more than 1.5-fold that of background were defined as positive particles. The number of particles was then quantified using the "analyze particle" function. The density of C-FOS$^+$ cells was then determined by the ratio of particle number to area. To outline the CA2 region of the hippocampus, adjacent slices were subjected to staining using the CA2 marker RGS14. To quantify the dendritic spine density and morphology, Cttnbp2 mutant mice were crossed with Thy1-YFP transgenic mice (#003782, Thy1-YFP-H, The Jackson Laboratory). The first branch of the apical dendrite of CA pyramidal neurons was selected for analysis (FIG. 5A). For each examined neuron, a 15-μm-long dendritic fragment 5 μm distant from the branch point was used to determine the density and length of spines and the width of spine heads. These quantifications were also performed using ImageJ.

1.6 TEM Analysis

Mice were perfused with PBS followed by mixed aldehyde fixatives (2% glutaraldehyde and 2% paraformaldehyde in PBS), and then immediately sectioned into 150-μm-thick coronal slices using a vibratome (VT1200S, Leica). Hippocampal CA1, CA3 and DG regions could then be identified and isolated for further analysis. The slices were post-fixed in aldehyde fixatives by microwaving at a power of 150 watts followed by osmium fixative (1% w/v of osmium tetroxide in 0.1 M cacodylate buffer) at a power of 100 watts. Samples then were stained en bloc with uranyl acetate 10% (w/v) at room temperature, dehydrated in graded alcohols and propylene oxide (PPO), embedded in EMBed 812 resin, and cured for 48 h at 60° C. The resulting resin block was cut into ultrathin sections (75 mu) using a diamond knife. Grids were stained with heavy metals, such as uranyl acetate and lead citrate. The grids, with the specimen side oriented downwards, remained in 4% uranyl acetate for 5 min and were then rinsed using drops of pure water. After rinsing, the grids were stained with Reynold's lead citrate for 10 min, rinsed again in pure water, and stored in a grid box. The stained sections on grids were then examined under an electron microscope (Talos L120C TEM, Thermo-Fisher Scientific). Images were randomly acquired using Digital cameras (4K×4K Ceta CMOS camera, Thermo-Fisher Scientific). Quantification of PSD and presynaptic vesicles were carried out using ImageJ.

1.7 LC-MS-MS Analysis of Synaptosomal Fractions Prepared from Mouse Forebrains

One hemisphere of the forebrains from adult mice (~8-weeks-old) were isolated and homogenized using a tissue dounce homogenizer with a loose pestle in 1 ml sucrose buffer [50 mM Tris-Cl pH 7.4, 320 mM sucrose, 2 mM DTT, 2 μg/ml leupeptin, 2 μg/ml pepstatin-A, 2 μg/ml aproteinin, 2 mM PMSF, 2 μg/ml MG132]. An aliquot of 50 μl of total homogenate was kept. The remainder of the total homogenate was centrifuged twice at 800×g for 10 min at 4° C. The supernatant was centrifuged at 9200×g for 15 min to collect the pellet as a crude synaptosomal fraction. The protein concentrations of total homogenates and synaptosomal fractions were determined by Bradford assay (Bio-Rad Protein Assay Dye Reagent Concentrate, Cat #5000006). Synaptosomal protein samples were then analyzed with LC-MS-MS and immunoblotting.

1.8 Analyses of Functional Protein Networks and Gene Ontology

After label-free quantification of the results of LC-MS-MS, fold-changes and p-values from the pairwise wild-type control vs. knockout comparisons were used for further analysis. Proteins were considered to be differentially abundant if they presented an adjusted p-value <0.05 and the peptide signal was reliable. For the functional network and gene ontology analysis shown in FIGS. 6B-6C, all upregulated and downregulated proteins in the knockout group were pooled. The STRING database (version 11.0, htts://string-db.orQ/) was employed for functional protein network analysis. The lines between nodes that indicate the interaction are based on experimental or STRING database evidence. Dashed lines represent inter-cluster edges and solid lines indicate intra-cluster interactions. The thickness of the lines indicates the strength of the supporting data. Networks were clustered using "MCL clustering" [46], and unlinked nodes are not shown. For gene ontology analysis, we used the "Molecular Signatures Database (MSigDB)" function in Gene Set Enrichment Analysis (GSEA, Broad Institute, http://software.broadinstitute.orgsea/index.sp). Pathway analysis included the Reactome and KEGG databases. Gene ontologies with q-values <0.05 and relevant to the nervous system are shown.

1.9 Immunoprecipitation 1.9.1 from COS1 Cells

To prepare the antibody-protein A complex, we incubated 30 µl of myc antibody (9E11, Cell signaling) with 30 µl of Protein A beads (Ser. No. 17/046,901, GE Healthcare) overnight and washed with PBS to remove unbound antibody. To prepare protein extract for immunoprecipitation, COS1 cell lysates were extracted with RIPA buffer [1% TX100, 0.1% SDS, 1% sodium deoxycholate, 50 mM Tris-Cl pH 7.4, 150 mM NaCl, 2 mM EDTA and protease inhibitors] and the debris was removed by centrifugation (16,000×g for 20 min at 4° C. using table top microcentrifuge, Heraeus Biofuge Fresco). Three hundred µg of lysate was incubated with myc tag antibody-coated Protein A beads for 4 hrs at 4° C. and washed once with each following buffers: (1) RIPA buffer, (2) 10 mM Tris-Cl, 1% Triton X 100, pH7.4, (3) 10 mM Tris-Cl, 0.1% Triton X 100, 0.5 M LiCl, pH7.4, (4) 10 mM Tris-Cl, pH7.4. After removing the final wash buffer, 30 µl of 2× sample buffer was added and boiled for 10 min.

1.9.2 from Mouse Brains

To prepare the antibody-protein A complex, we incubated 5 µg of CTTNBP2 antibody (clone A7) [9] with 20 µl of Protein A beads (Ser. No. 17/046,901, GE Healthcare) overnight and washed with PBS to remove unbound antibody. To prepare protein extract for immunoprecipitation, adult mouse brain (~8 weeks old) samples were homogenized in RIPA buffer and the debris was removed by centrifugation (16,000×g for 20 min at 4° C. using table top microcentrifuge, Heraeus Biofuge Fresco). One mg of lysate was incubated with CTNBP2 antibody-coated Protein A beads for 4 hrs at 4° C. and washed once with RIPA buffer, five times with 1% TX100 in PBS, and then three times with PBS. After removing the wash buffer, 50 µl of 2× sample buffer was added and boiled for 10 min.

1.10 Immunoblotting

To validate CTTNBP2 expression in knockout mice, adult mouse brain (~8 weeks old) samples were homogenized in RIPA buffer. After 30 min, debris was removed by centrifugation (13000 rpm in a microcentrifuge for 20 min). The supernatants were collected and protein amounts were determined by Bio-Rad Protein Assay Dye Reagent Concentrate. Protein samples were denatured by 2× sample buffer and boiled for 10 min. Five µg of protein samples were separated by SDS-PAGE and then transferred to PVDF membrane. Membranes were blocked using blocking buffer [5% skim milk and 0.1% Tween-20 in PBS] for 30 min and hybridized with primary antibodies. In principle, primary antibody was added into blocking buffer and hybridized with the membrane overnight at 4° C. or for 3 hr at room temperature. Horseradish peroxidase-conjugated goat anti-mouse, rabbit, or guinea pig secondary antibodies were used to detect primary antibody and were visualized using a Western Lightening Plus ECL system (PerkinElmer).

1.11 Zinc, Serine and BCAAs

A zinc ion source, a serine component and BCAAs were purchased from Sigma-Aldrich Company Ltd under the catalogues numbers, including Zinc sulfate heptahydrate ($ZnSO_4 \cdot 7H_2O$, Z0251), L-Serine (S4311), L-Leucine (L8912), L-Isoleucine (I7403) and L-Valine (V0513). A supplement or supplement mixture was prepared by mixing a zinc ion source, a serine component and/or BCAAs at various concentrations in drinking water for behavior analyses.

1.12 Zinc Supplementation of Drinking Water

Figure 8A:
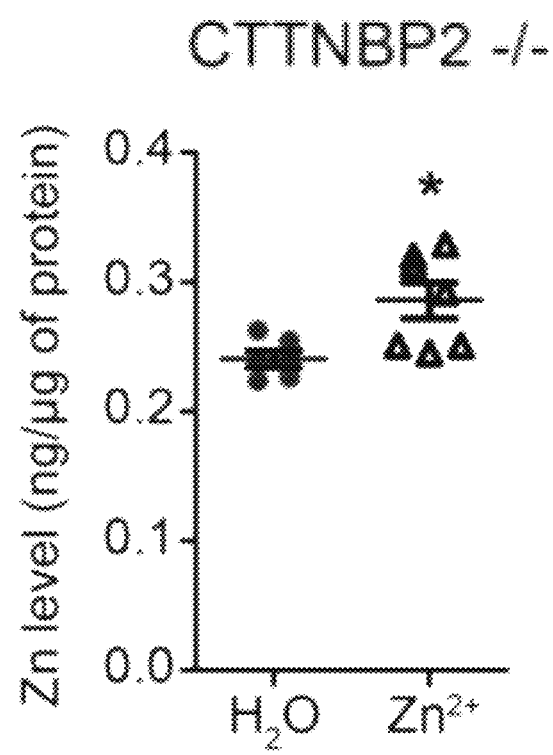
FIGS. 8A to 8E shows zinc ameliorates the deficits of Cttnbp2 mutant mice.
Figure 8B:
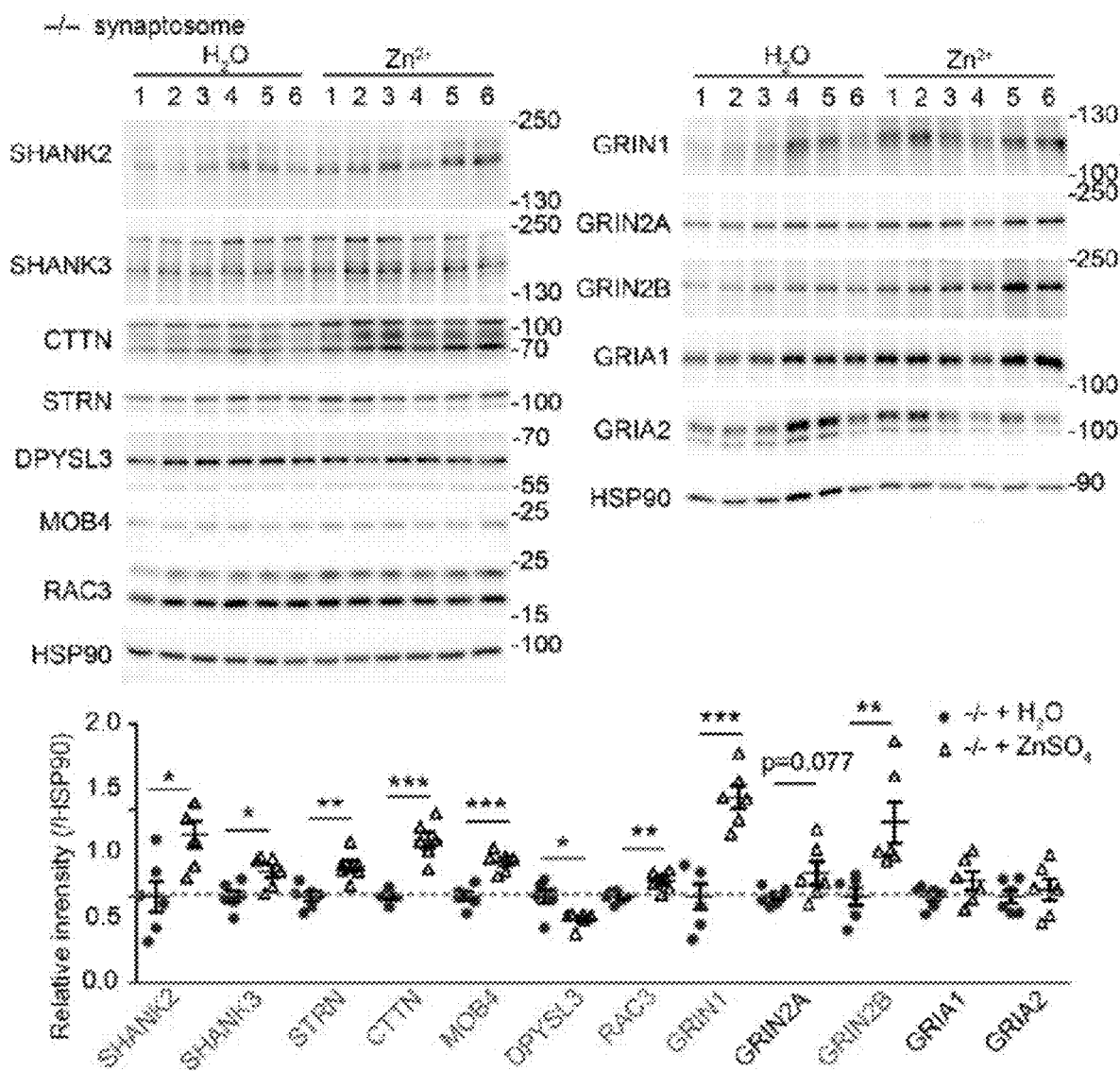
Figure 8C:
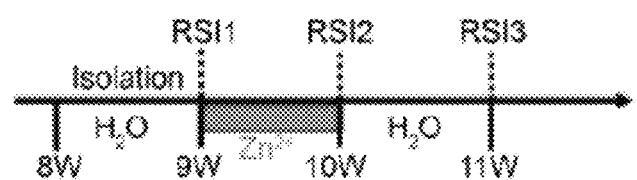

The concentration of zinc in the mouse chow (5K54, LabDiet) provided in our animal facility is 84 ppm. To increase the zinc intake to ~150 ppm [30], mice were provided with $ZnSO_4$ (Z0251, Sigma-Aldrich) in drinking water at a concentration of 40 ppm, which is based on daily consumption of ~5 ml water and 2.5 g chow by each mouse. To study the expression of synaptic proteins after zinc supplementation, adult mice (~8 weeks old) were fed with zinc-supplemented water or normal drinking water as control for 7 days and then sacrificed for synaptosomal analysis as described above. To validate the zinc levels in brain, zinc quantification kit (ab102597, Abcam) was used according to manufacturer's instruction. The zinc concentrations were normalized by protein amounts. To study the effect of zinc supplementation on social behavior of Cttnbp2 deletion and mutant mice, three consecutive trials of reciprocal social interaction were performed at intervals of 7 days (FIG. 8C). The first trial was performed before zinc supplementation. After the first trial, mice were provided with zinc-supplemented water (40 ppm) for 7 days and then subjected to the second trial. After the second trial, zinc-supplemented water was replaced with normal drinking water for 7 days and mice then underwent the third trial. Reciprocal social interaction trials were performed as described above.

1.13 Assessing the Ameliorating Effect of D-Cycloserine

To analyze the effect of D-cycloserine (DCS, ab120121, Abcam) on social behaviors of Cttnbp2 mutant mice, adult mice (~8 weeks old) were first habituated to handling by subjecting them to an open field with or without inanimate objects. Mice were then isolated until ~10 weeks old for reciprocal social interaction trials. During isolation, mice were habituated to intraperitoneal injection, which effectively reduces their anxiety response to intraperitoneal injection during the experimental period. On day 1 of the experiment, saline control (0.9% of NaCl) was intraperitoneally injected into the test animal 30 min before a reciprocal social interaction trial, conducted as described above. On day 2 of the experiment, D-cycloserine solution (2 mg/kg in 0.9% of NaCl) was intraperitoneally injected into mice 30 min before a reciprocal social interaction trial.

1.14 Statistical Analysis

All image measurements, including morphometry analysis and immunoblotting analysis, were carried out using ImageJ. To quantify the relative expression level of each protein, we acquired the blotting intensity of each band and normalized against the intensity of HSP90 from the same membrane. To acquire movement traces and activity heatmaps, video files were analyzed using the Smart Video Tracking System (Panlab). All image analyses and behavior experiments were conducted blind. Statistical analysis and graphical outputs were performed in PRISM 5.03 or 7 (Graphpad software). All the data were analyzed by Normality test (D'Agostino and Shapiro-Wilk) unless the sample sizes are not suitable. To compare two genetically distinct groups (i.e., +/+ versus −/−, +/+ versus M120I or +/+ versus R533*), a two-tailed unpaired t-test was performed for normally distributed data and two-tailed Mann-Whitney test was performed for nonparametric distributed data. To compare social preference (Ob to S1 or S2 to S1) and treatment effects ($H_2O$ versus $Zn^{2+}$ or saline versus D-cycloserine solution) on the same animals, two-tailed paired t-tests were performed for normally distributed data and two-tailed Wilcoxon matched-pairs signed rank test was performed for nonparametric distributed data. To compare multiple genetically distinct groups, one-way ANOVA with Dunnett's or Bonferroni multiple comparison post hoc test was performed for normally distributed data and Kruskal-Wallis test with Dunn's multiple comparison test was performed for nonparametric distributed data. For all comparisons, $P<0.05$ was considered significant. Outliers in the dataset were excluded according to the box-plot method (https://courses.lumenlearning.com/atd-odessa-statistics/chapter/box-plots/). In brief, values exceeding 1.5-fold the interquartile range above the upper quartile or below the lower quartile were regarded as outliers.

2. Results 2.1 Cnbp2 Deletion Impairs Social Interaction in Mice

Figure 1B:
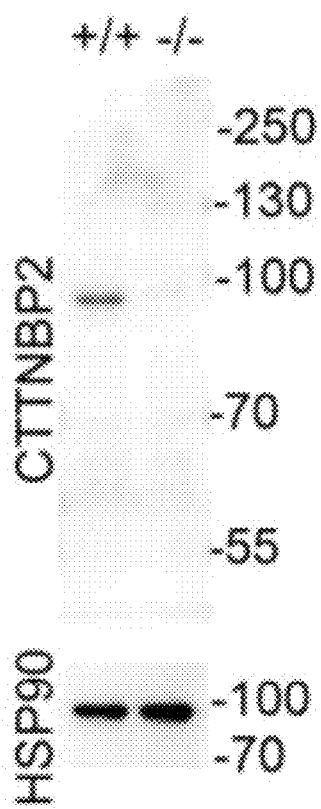
Figure 1C:
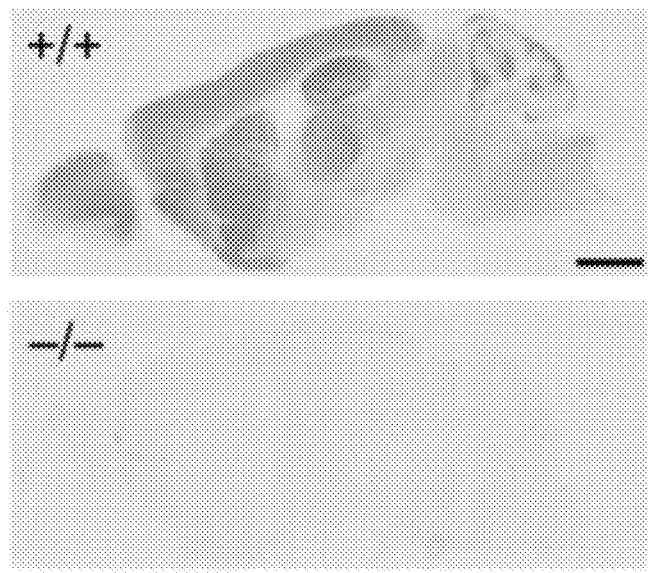
Figure 1D:
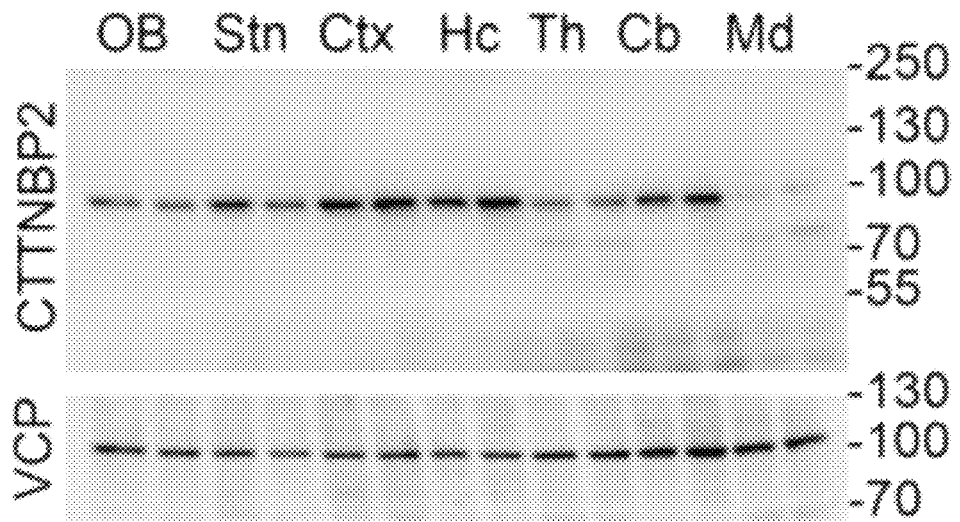

We generated both Cttnbp2 knockout mice and knockin mice carrying ASD-associated mutations. The transcription activator-like (TAL) effector nucleases (TALEN) technique was used to generate Cttnbp2 knockout mice. Two mouse lines carrying frameshift deletions in exon 3 of the Cttnbp2 gene were identified (FIG. 1A). Since line 1-9 bred much faster than line 3-1, we used the former line for our study. In addition to sequencing and genomic PCR, we also performed immunoblotting with CTTNBP2 antibody to confirm the absence of CTTNBP2 in Cttnbp2−/− mouse brains (FIG. 1B). Cttnbp2 deficiency did not alter the global appearance of mice or their brains. Immunoblotting and immunohistochemical analysis indicated that CTTNBP2 proteins were widely distributed in the brains of wild-type mice, with much higher levels in the forebrain (including in the cerebral cortex, hippocampus and striatun) and a moderate level in the thalamus (FIG. 1C, FIG. 1D). CTTNBP2 immunoreactivity was specific because no noticeable signal was detected in Cttnbp2−/− brains (FIG. 1B, FIG. 1C).

Figure 1E:
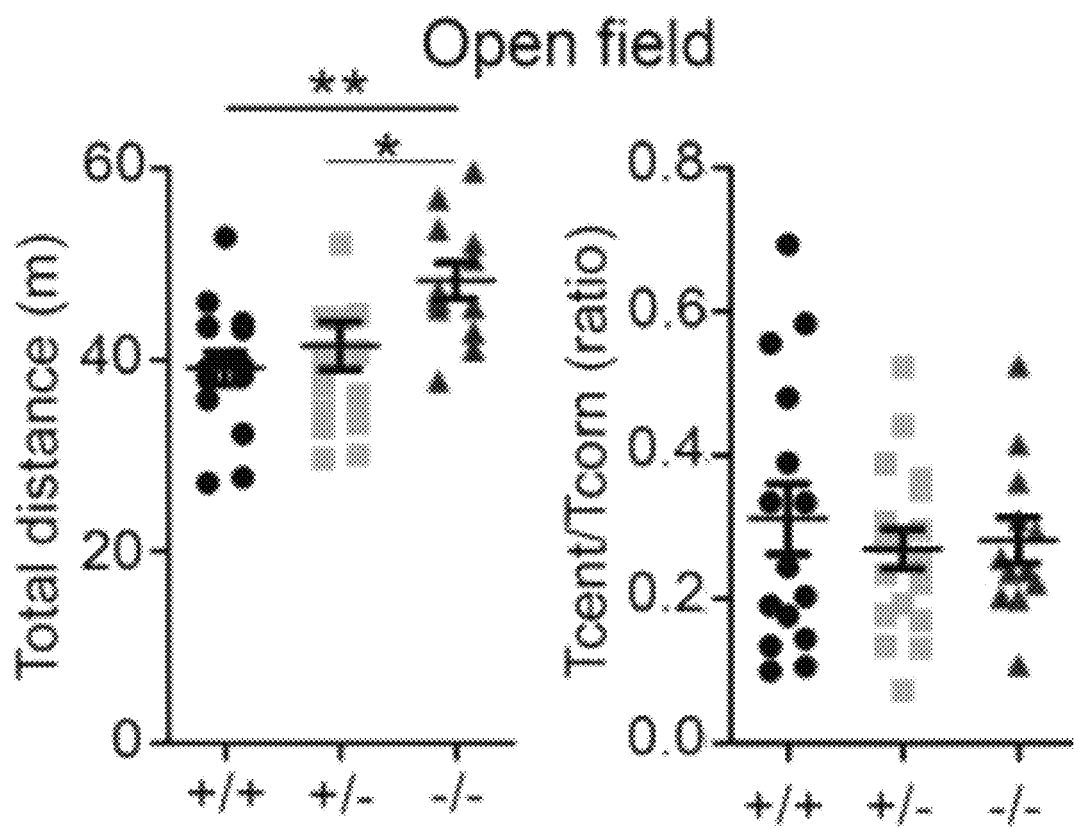
Figure 1F:
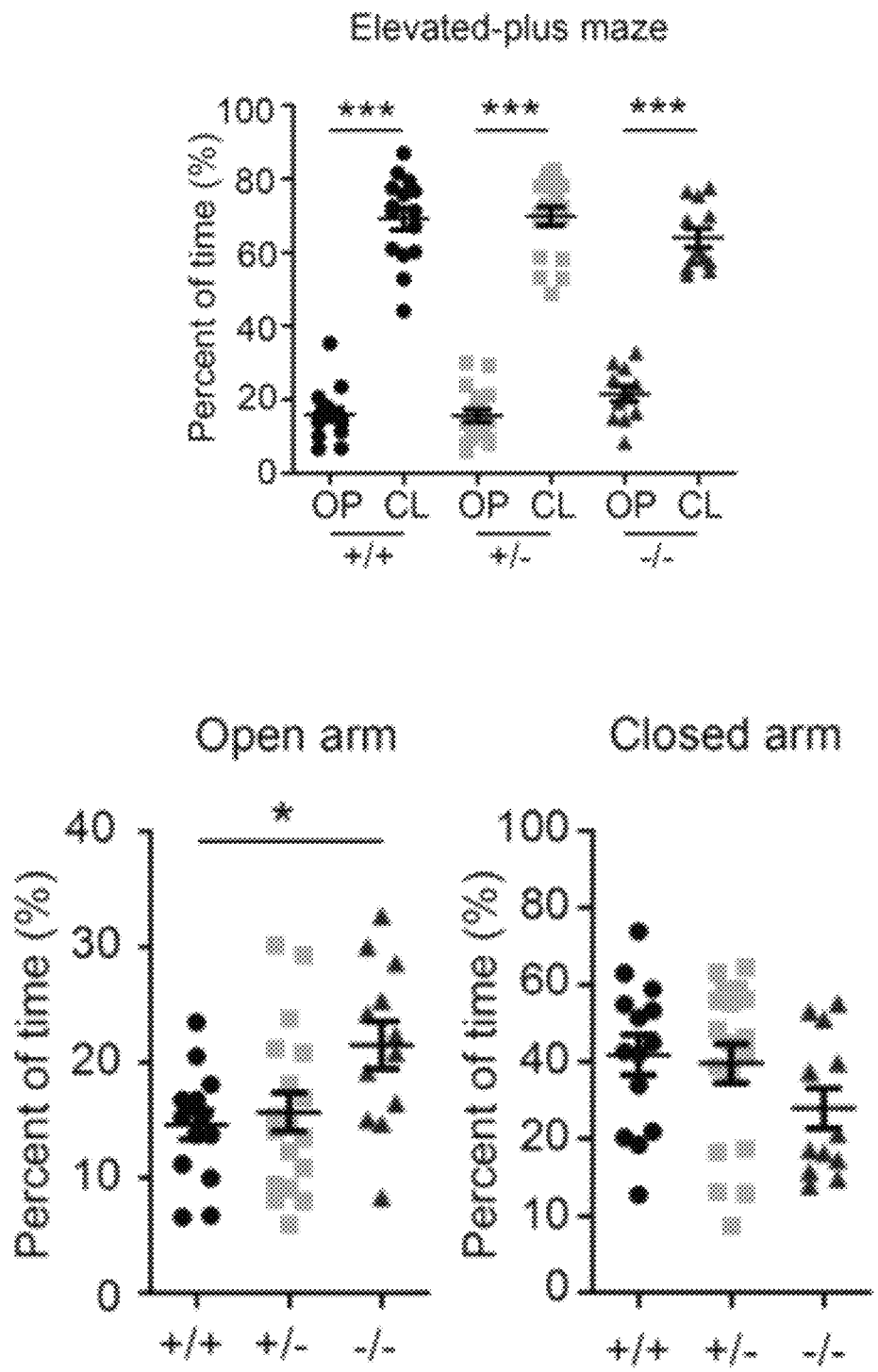

We then used a series of behavioral paradigms to characterize Cttnbp2-deficient mice. An open field task was first used to monitor locomotor activity and anxiety of mice in a new environment. We found that Cttnbp2+/− mice and wild-type littermates (+/+) presented similar total moving distances. However, moving distances of Cttnbp2−/− mice were longer than those of wild-type mice, suggesting Cttnbp2−/− mice exhibited higher locomotor activity (FIG. 1E, left). All Cttnbp2+/+, +/− and −/− mice spent similar amounts of time in the corner and center areas of the open field, suggesting that Cttnbp2 deficiency may not result in anxiety in our assay conditions (FIG. 1E, right). We also subjected mice to an elevated plus maze test, which is a typical assay for measuring anxiety in rodents. Both Cttnbp2+/− and Cttnbp2−/− mice preferred the closed arms over the open arms of the maze (FIG. 1F, top). However, the amount of time spent in open arms, but not in closed arms, differed for Cttnbp2−/− mice (FIG. 1F, bottom). Taken together, the results of our open field and elevated plus maze assays suggest that Cttnbp2 deletion results in slight hyperactivity and anxiolytic effect.

Figure 1G:
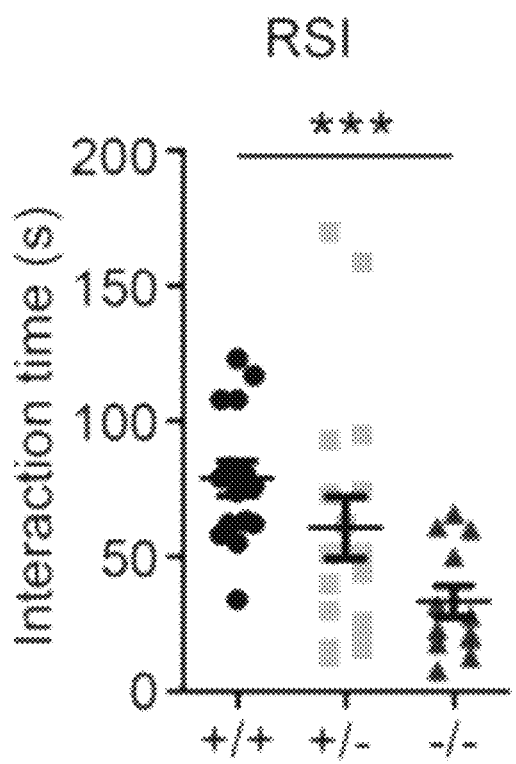
Figure 1H:
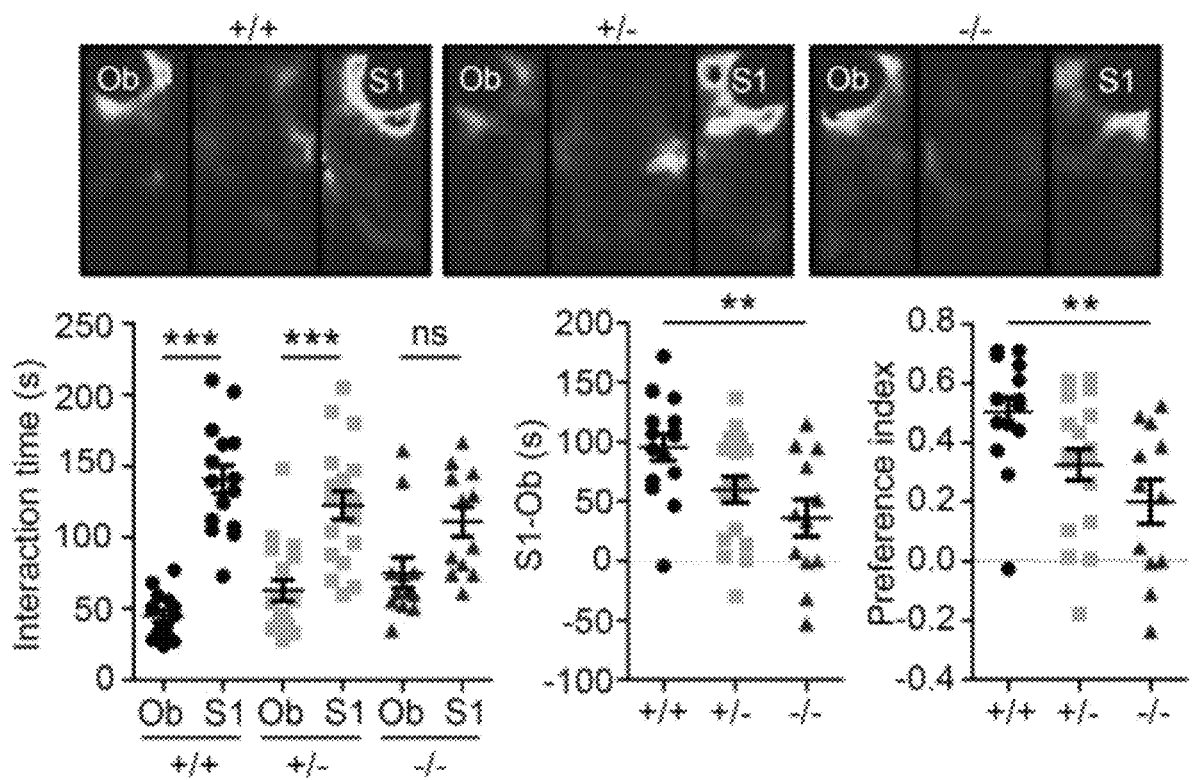
Figure 1I:
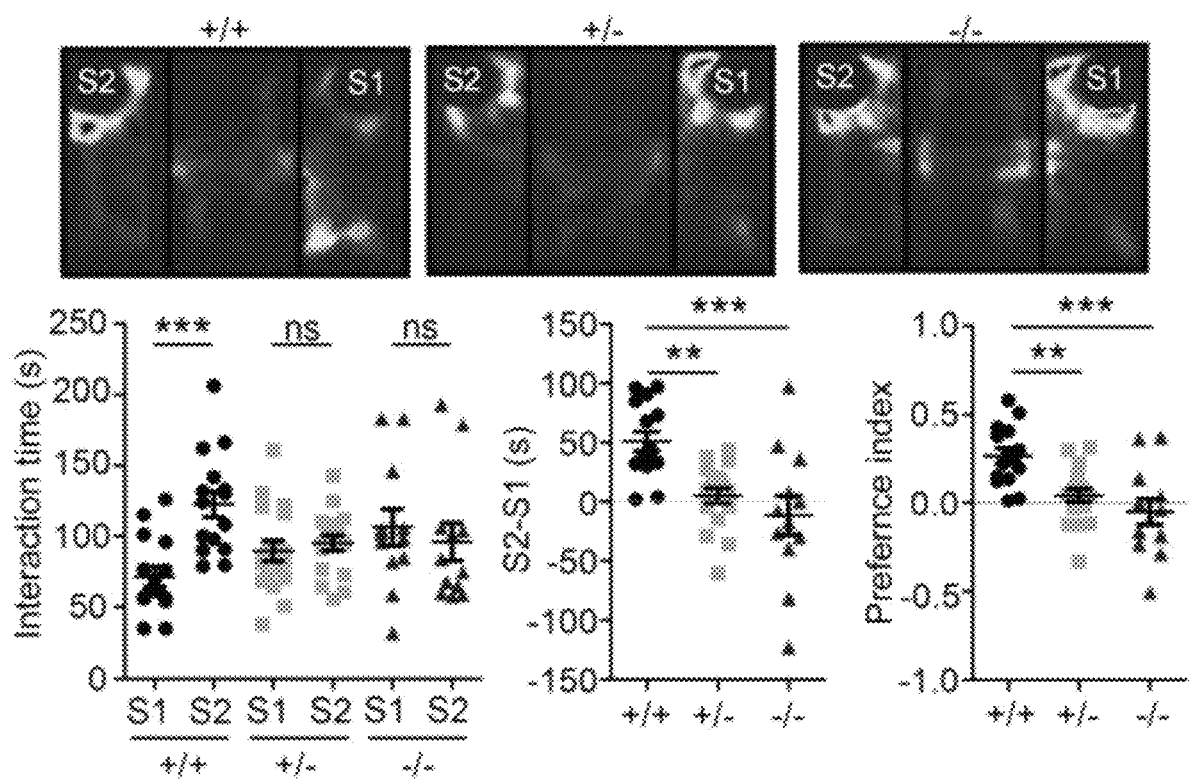

We then conducted two paradigms to analyze social interaction behavior of Cttnbp2-deficient mice, i.e. reciprocal social interaction (RSI) and three-chamber test. For RSI, we found that though both Cttnbp2+/− and Cttnbp2−/− mice tended to have shorter interactions with strangers, only the results for Cttnbp2−/− mice were significantly different from those of wild-type littermates (FIG. 1G), suggesting Cttnbp2−/− mice exhibit reduced social interaction. For the three-chamber test, after habituating mice to the chamber, we recorded the time it took for them to approach a newly introduced mouse (stranger 1) and an object placed in the cages to measure sociability. We then replaced the object with a mouse (stranger 2). Preferential interaction with stranger 2 indicates the novelty preference of social behaviors of test mice. Although Cttnbp2+/+, +/− and −/− mice all spent more time interacting with stranger 1 than with the object (FIG. 1H, bottom left panel), the difference between the time it took to approach stranger 1 and the time it took to approach the object was significantly lower in Cttnbp2−/− mice compared to wild-type, but this was not the case for Cttnbp2+/− mice (FIG. 1H). Similar results were observed when we analyzed the preference index (FIG. 1H). These data suggest that Cttnbp2−/− mice, but not Cttnbp2+/− mice, exhibit reduced sociability, consistent with our RSI results. When simultaneously presented with stranger 1 and stranger 2 mice, WT mice spent more time interacting with stranger 2. In contrast, both Cttnbp2+/− and −/− mice spent similar amounts of time approaching stranger 1 and stranger 2 (FIG. 1I). The differences in interaction time and the preference indices further indicate that Cttnbp2+/− and −/− mice are defective in novelty preference (FIG. 1I). Taken together, the results of our RSI and three-chamber tests suggest that Cttnbp2 deficiency negatively impacts the social behaviors of mice and that the Cttnbp2−/− phenotype is more severe than that of Cttnbp2+/− mice, which is likely related to gene dosage.

In conclusion, our behavioral analyses suggest that Cttnbp2−/− mice exhibit social deficits, slight hyperactivity and anxiolysis, whereas Cttnbp2+/− mice have a milder phenotype in which only novelty preference (namely social memory) is defective.

2.2. ASD-Associated Mutations of Cnbp2 Reduce Dendritic Spine Number in Cultures The above-described results suggest that Cttnbp2+/− and −/− mice have social deficits, a key symptom exhibited by ASD patients. To further investigate the relevance of Cttnbp2 for ASD, we analyzed mutations of that gene identified in ASD patients and investigated if they disrupted the function of CTTNBP2 in controlling dendritic spine formation and mouse behaviors. We introduced seven ASD-associated mutations of the short form of human CTTNBP2 [4, 5] at the corresponding residues of mouse CTTNBP2

Figure 2A:
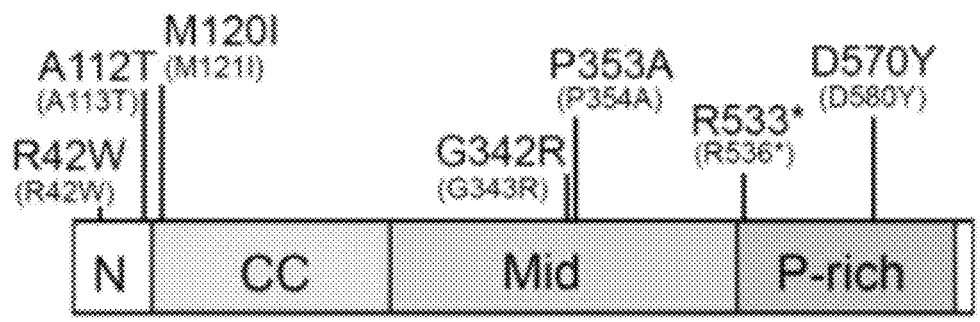
FIGS. 2A to 2C show that Cttnbp2 ASD-associated mutations impair dendritic spine formation and the interaction with cortactin.
Figure 2B:
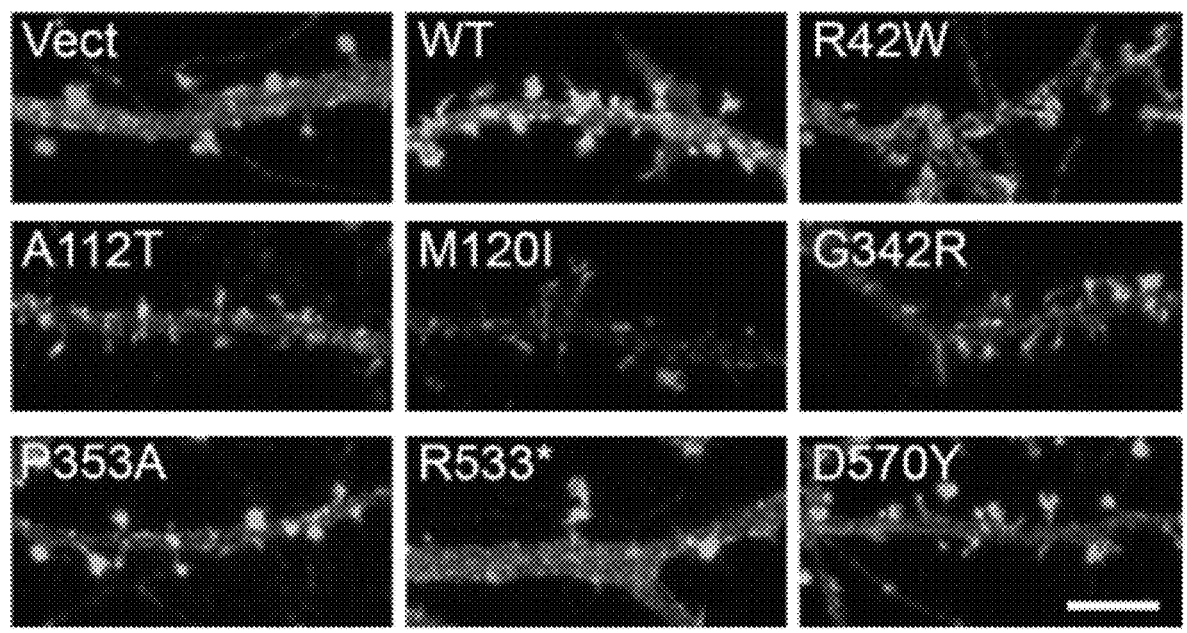
Figure 2C:
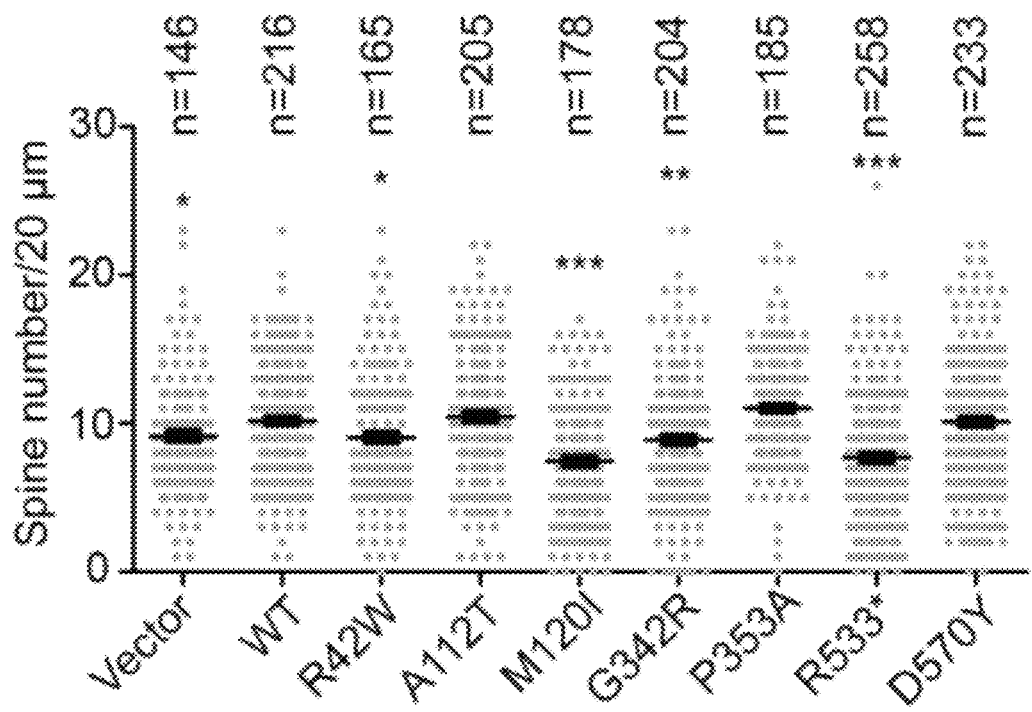

(FIG. 2A). These mutations are widely distributed across the entire short form of CTTNBP2 (FIG. 2A). The ASD-associated Cttnbp2 mutant constructs were transfected into cultured hippocampal neurons for further analyses (FIG. 2B). In mature cultured neurons, overexpressed wild-type CTTNBP2 formed puncta at dendritic spines, as well as bundles along axons and a few dendrites. The R42W, A112T, G342R and P353A mutants presented a similar distribution pattern to wild-type CTTNBP2. The M120I mutant still generated puncta, but they tended to be present in soma and along dendritic shafts. The R533* mutation impaired the punctate pattern and resulted in an even distribution of mutant protein in neurons. The D570Y mutant tended to form bundles along dendritic and axonal shafts. We then measured the dendritic spine density of neurons expressing these Cttnbp2 mutants. Our results show that compared with WT construct, expression of R42W, M120I, G342R and R533* mutants reduced dendritic spine densities in hippocampal cultures (FIG. 2B, FIG. 2C).

2.3 Impaired Social Interactions of Cnbp2 M120I and R533* Mutant Mice

Figure 3A:
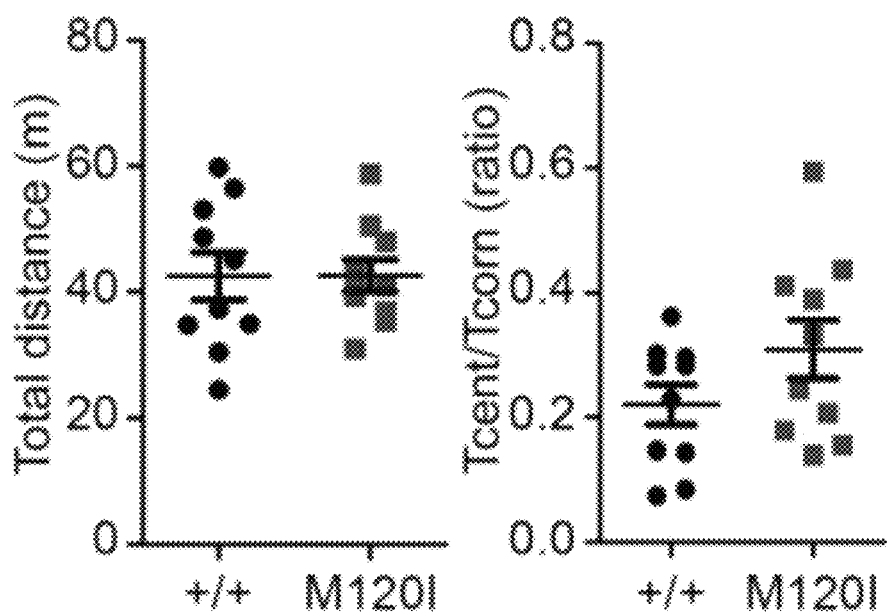
Figure 3B:
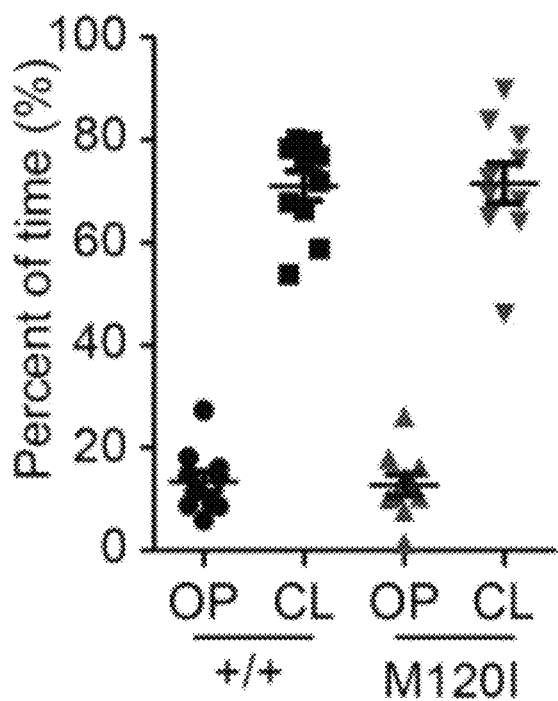
Figure 3C:
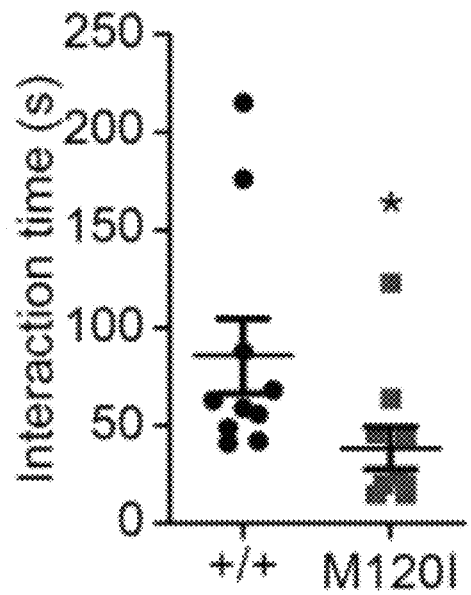
Figure 3D:
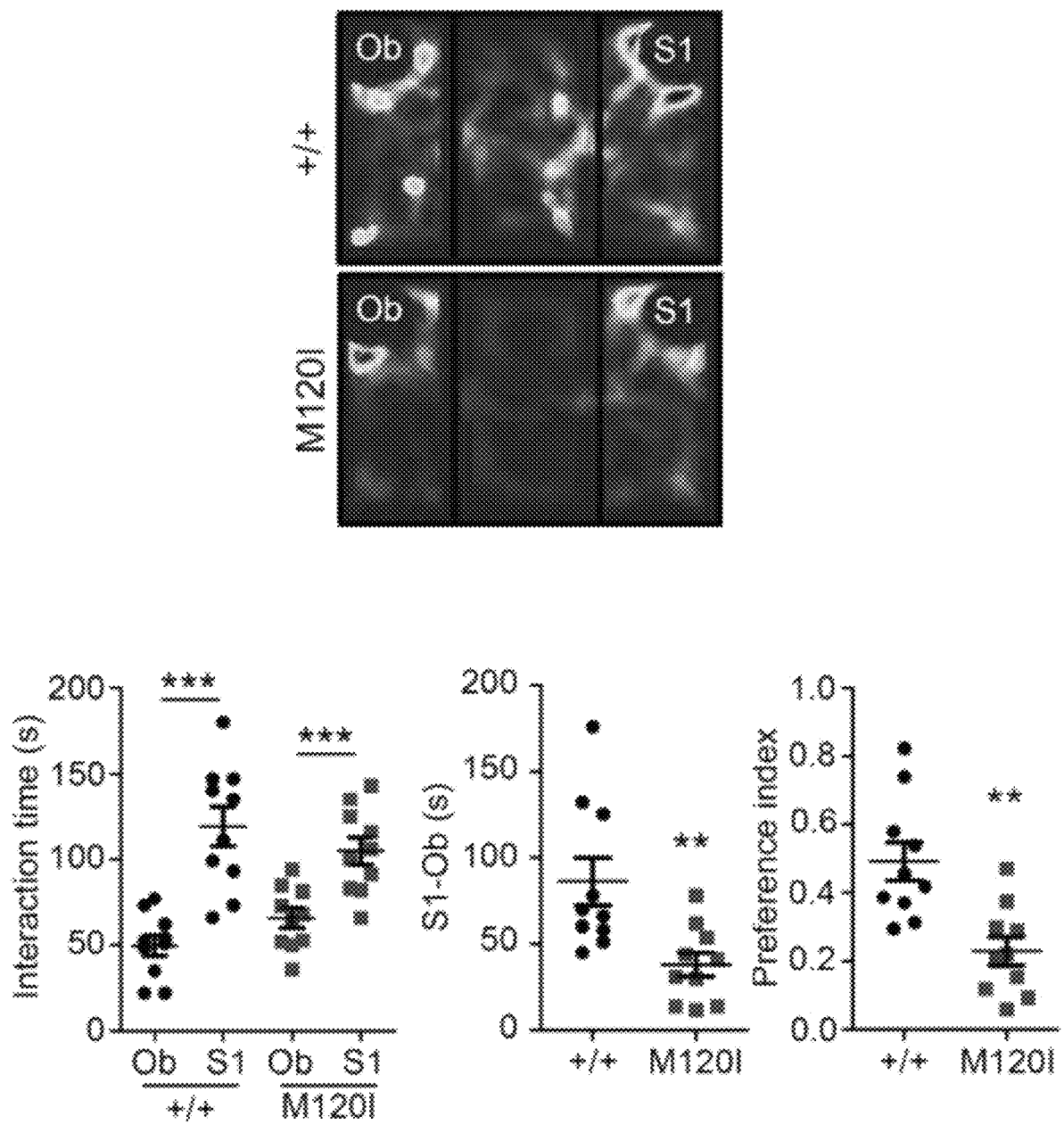
Figure 3E:
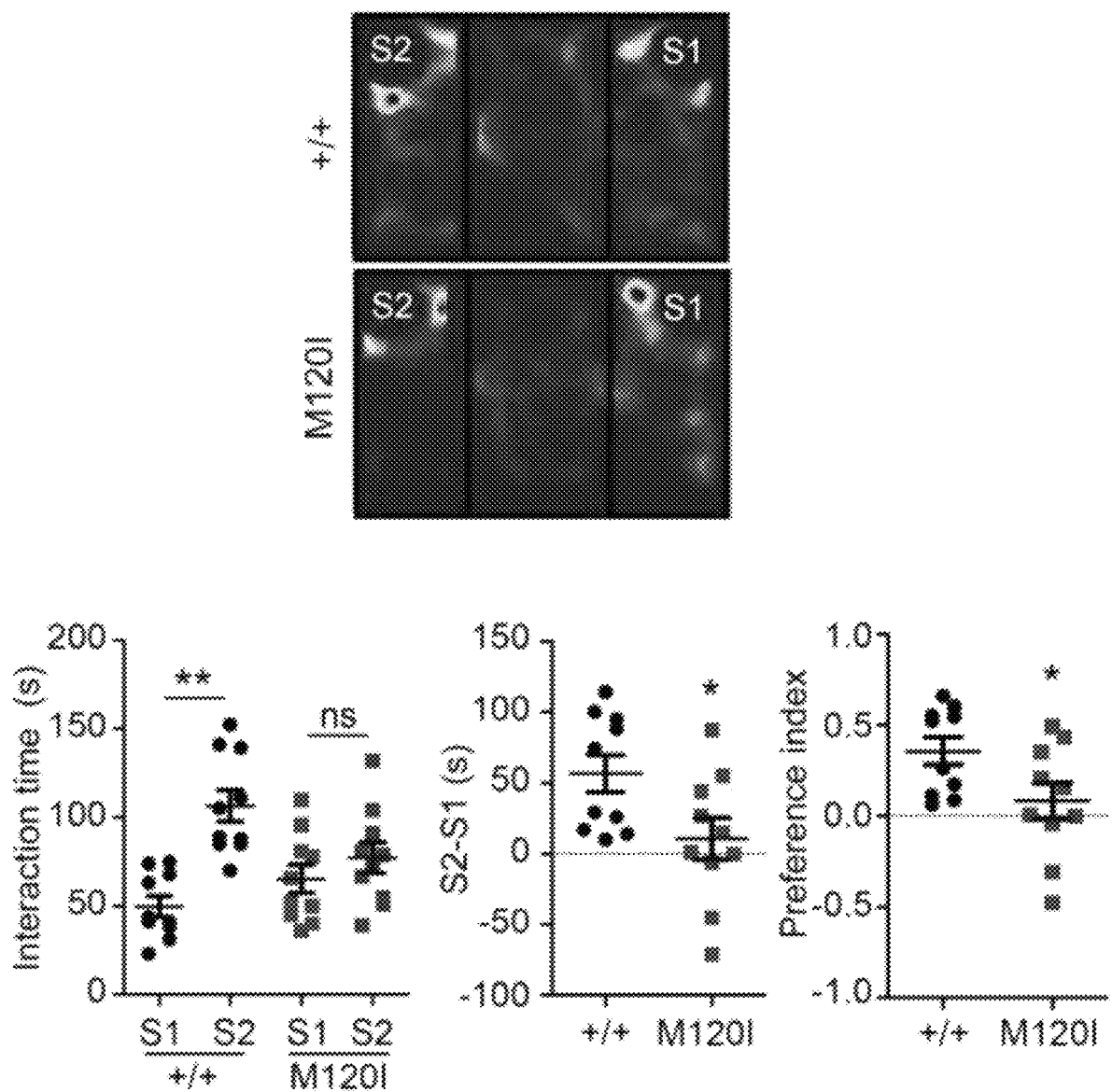
Figure 3I:
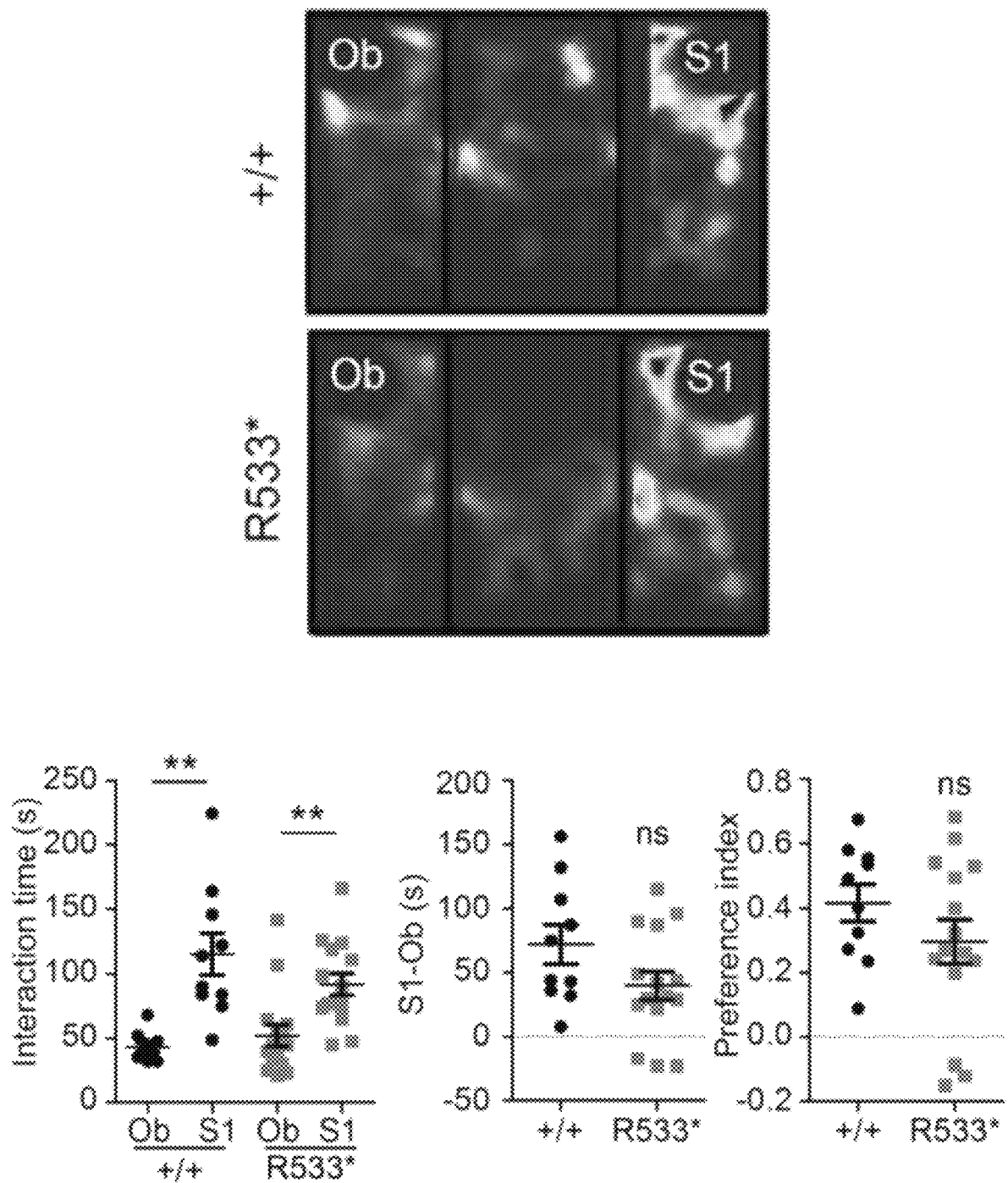
Figure 3J:
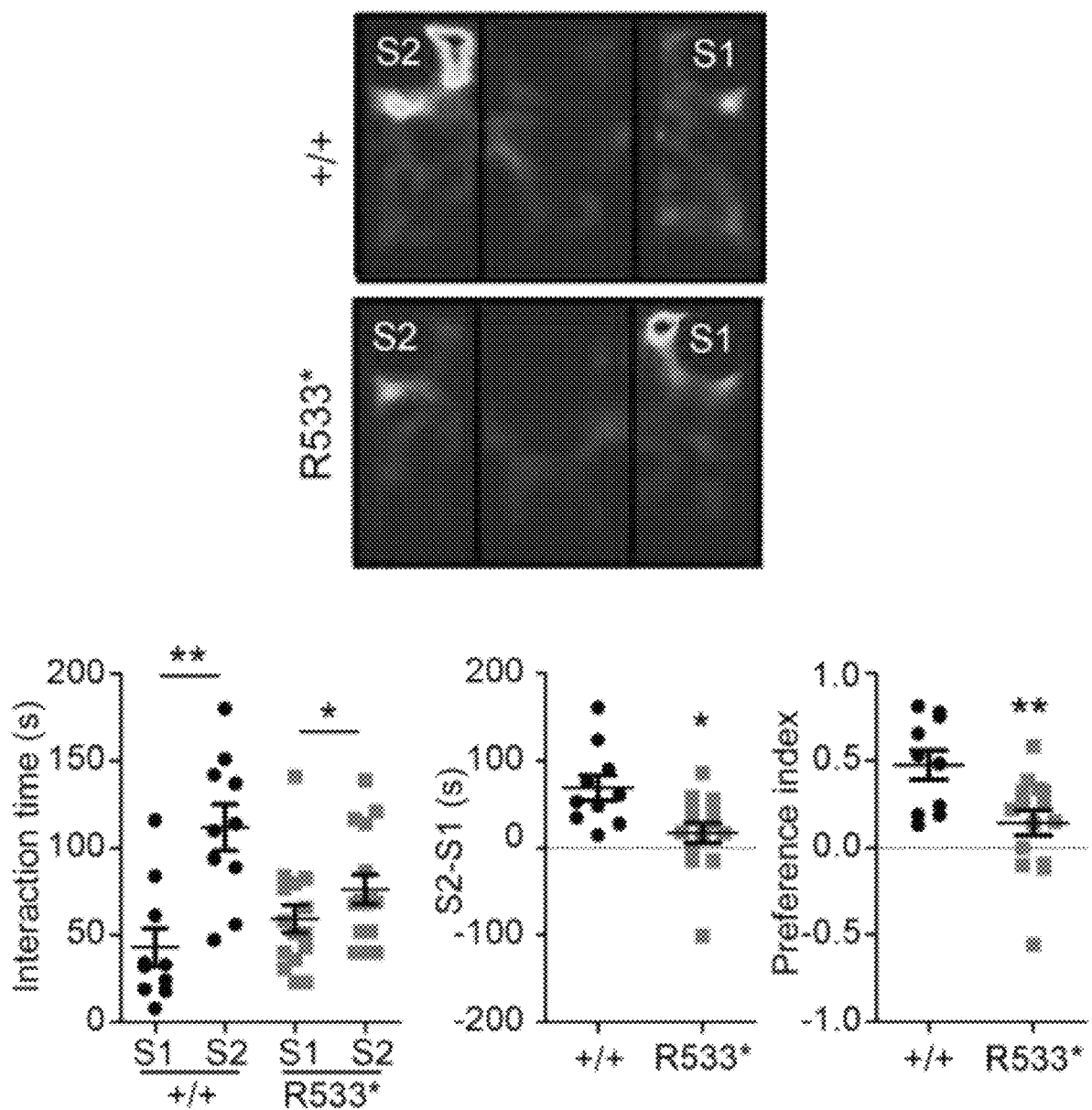
Figure 4A:
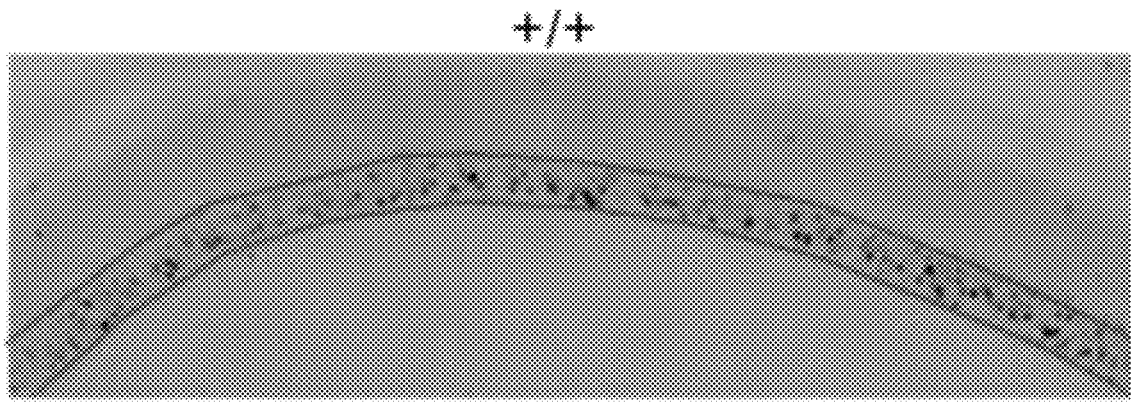
FIGS. 4A to 4D show Cttnbp2 deficiency results in reduced neuronal activation upon social stimulation.
Figure 4A:
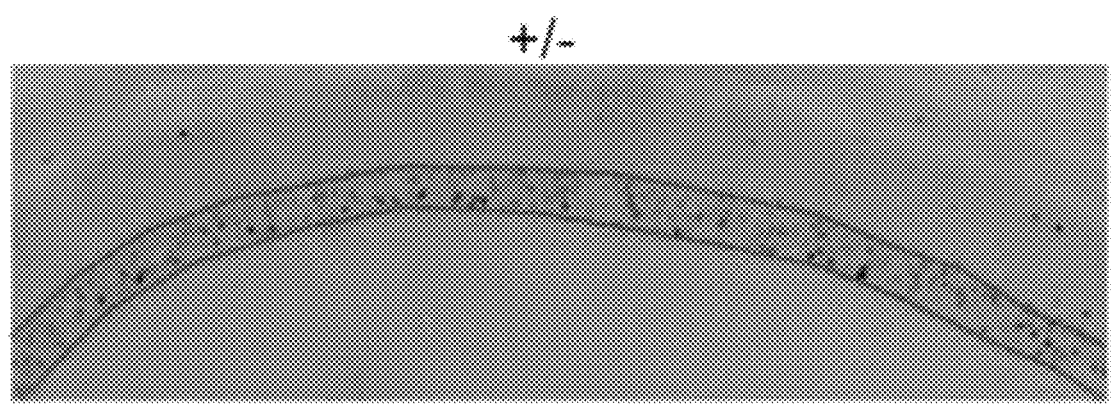
Figure 4A:
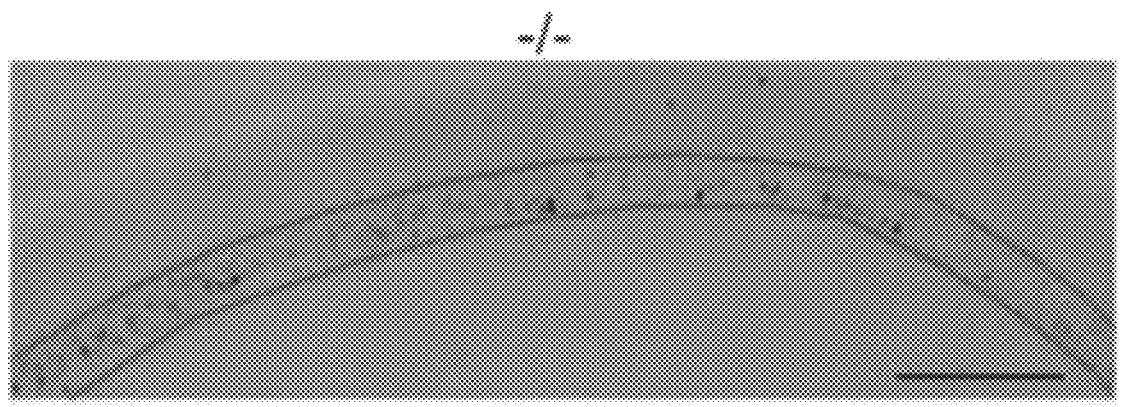
Figure 4B:
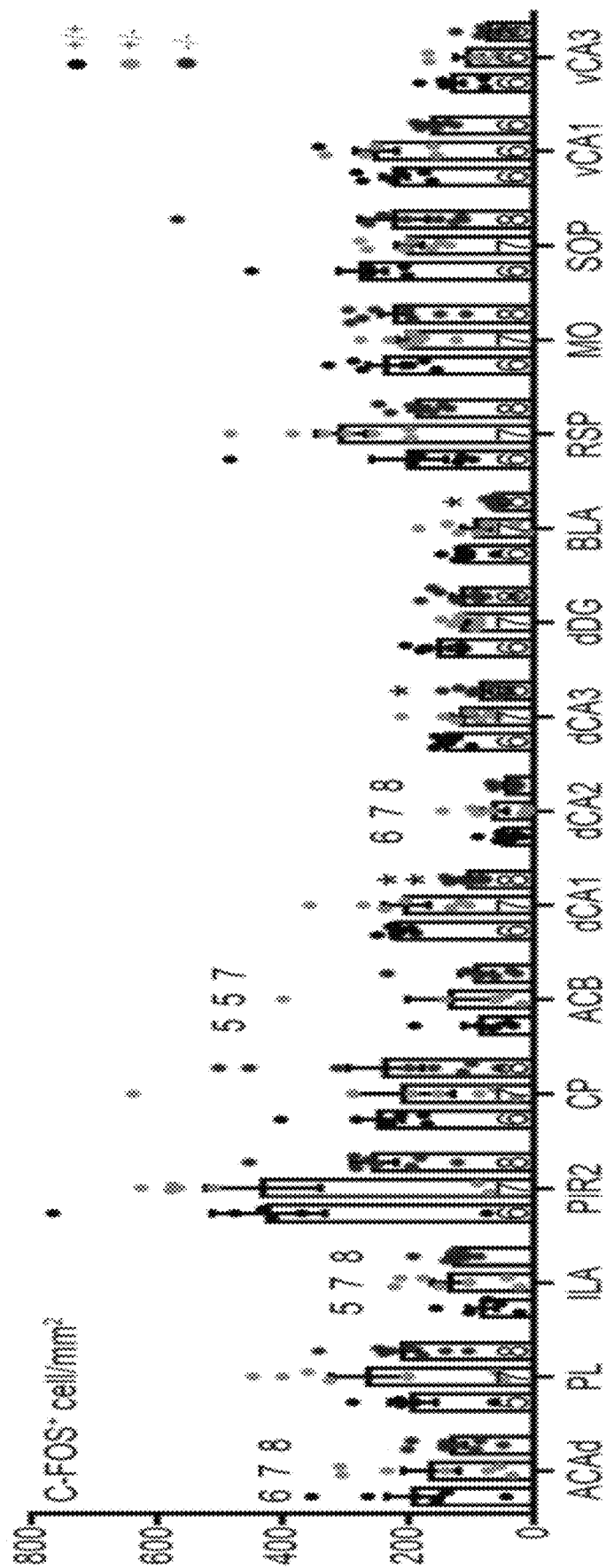
Figure 4C:
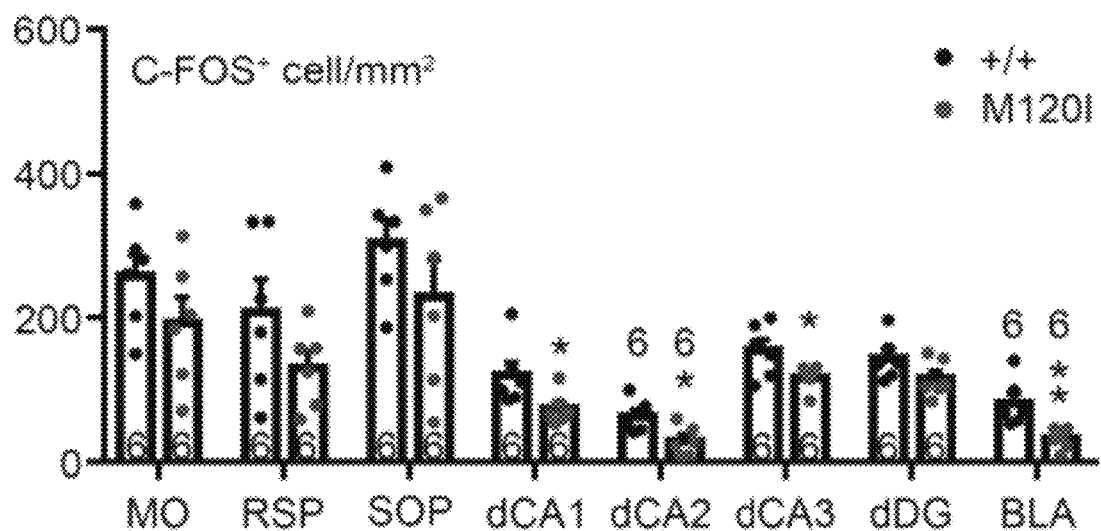
Figure 4D:
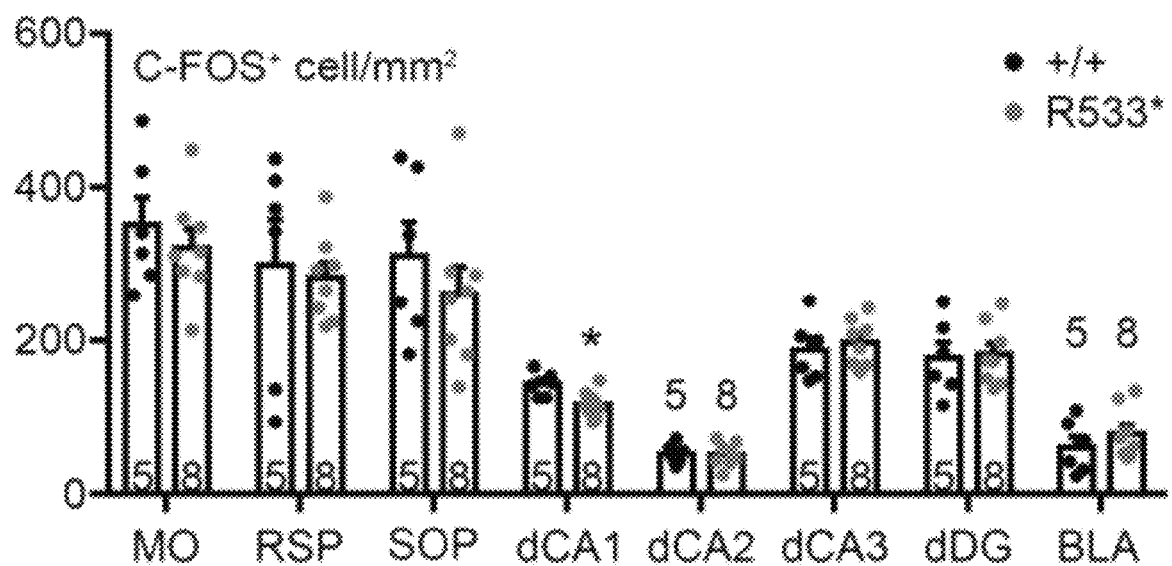

We applied the CRISPR/Cas9 technique to generate M120I and R533* knockin mutant mice. Since only one of the CTINBP2 alleles carries either of these mutations in ASD patients [4], we used heterozygous knockin mice to mimic patient conditions. As for gene knockout, these ASD-associated mutations did not alter the morphological or anatomical features of mouse brains or the general appearance of mutant mice. We applied behavioral assays to analyze these two mutant mouse lines. In contrast to Cttnbp2-/- mice, neither M120I nor R533* mutant mice exhibited noticeable defects in open field and elevated plus maze assays (FIGS. 3A-3B, FIGS. 3F-3G), suggesting that these two ASD-associated mutations do not influence locomotor activity or anxiety in mice. We also assessed these mutant mice by RSI and three-chamber tests. Both M120I and R533* mutant mice spent less time approaching the unfamiliar mouse in RSI compared with wild-type littermates (FIG. 3C, FIG. 3H). In three-chamber test, M120I mutant mice showed impaired sociability and novelty preference (FIG. 3D, FIG. 3E). However, for R533* mutant mice, only novelty preference was noticeably affected in the three-chamber test (FIG. 3I, FIG. 3J). Thus, CTTNBP2 ASD-associated mutations influence social behaviors in mice, with M120 mutant mice being similar to Cttnbp2-/- mice, whereas 533* mutant mice resemble Cttnbp2+/- mice.

Figure 5B:
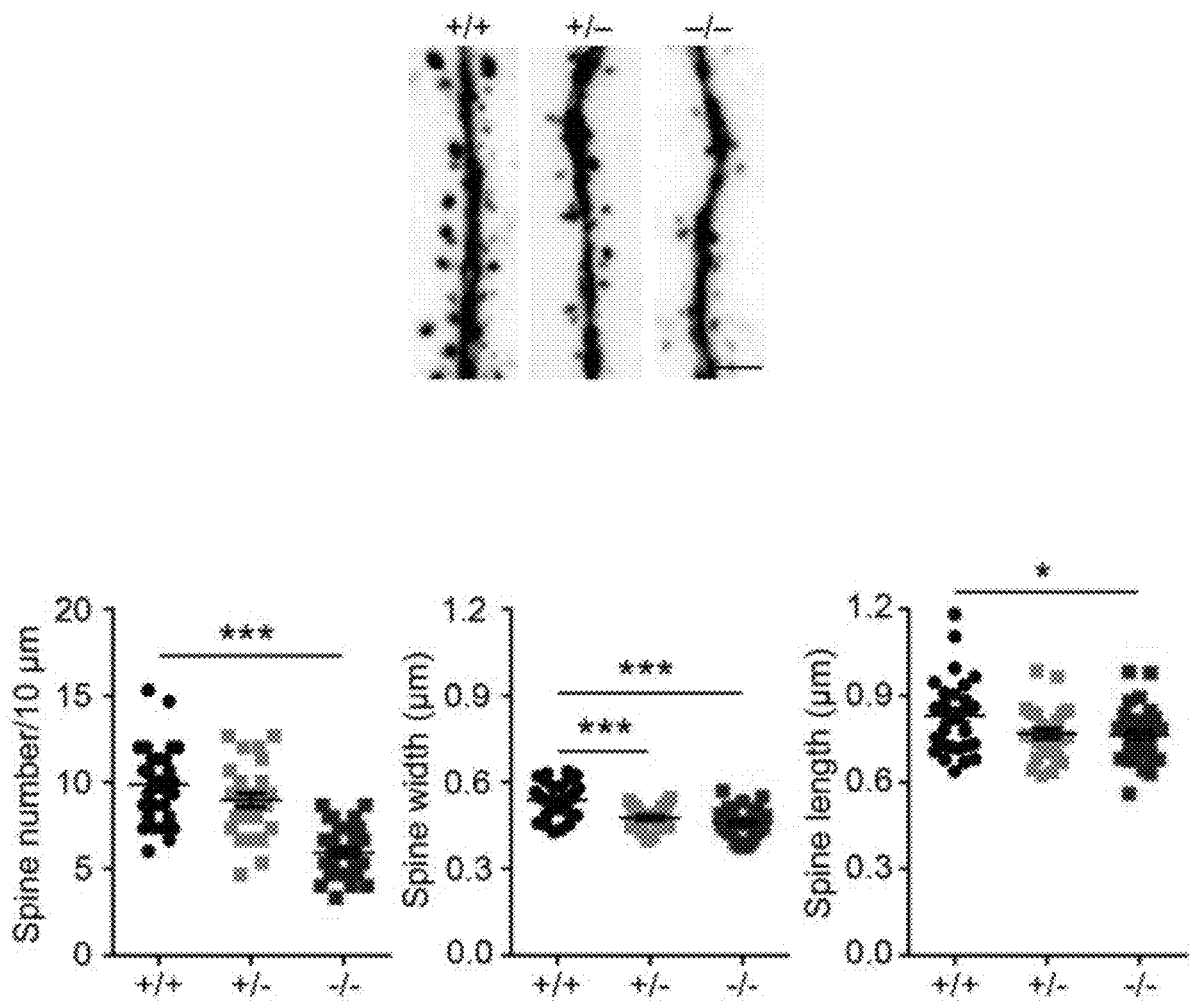
Figure 5C:
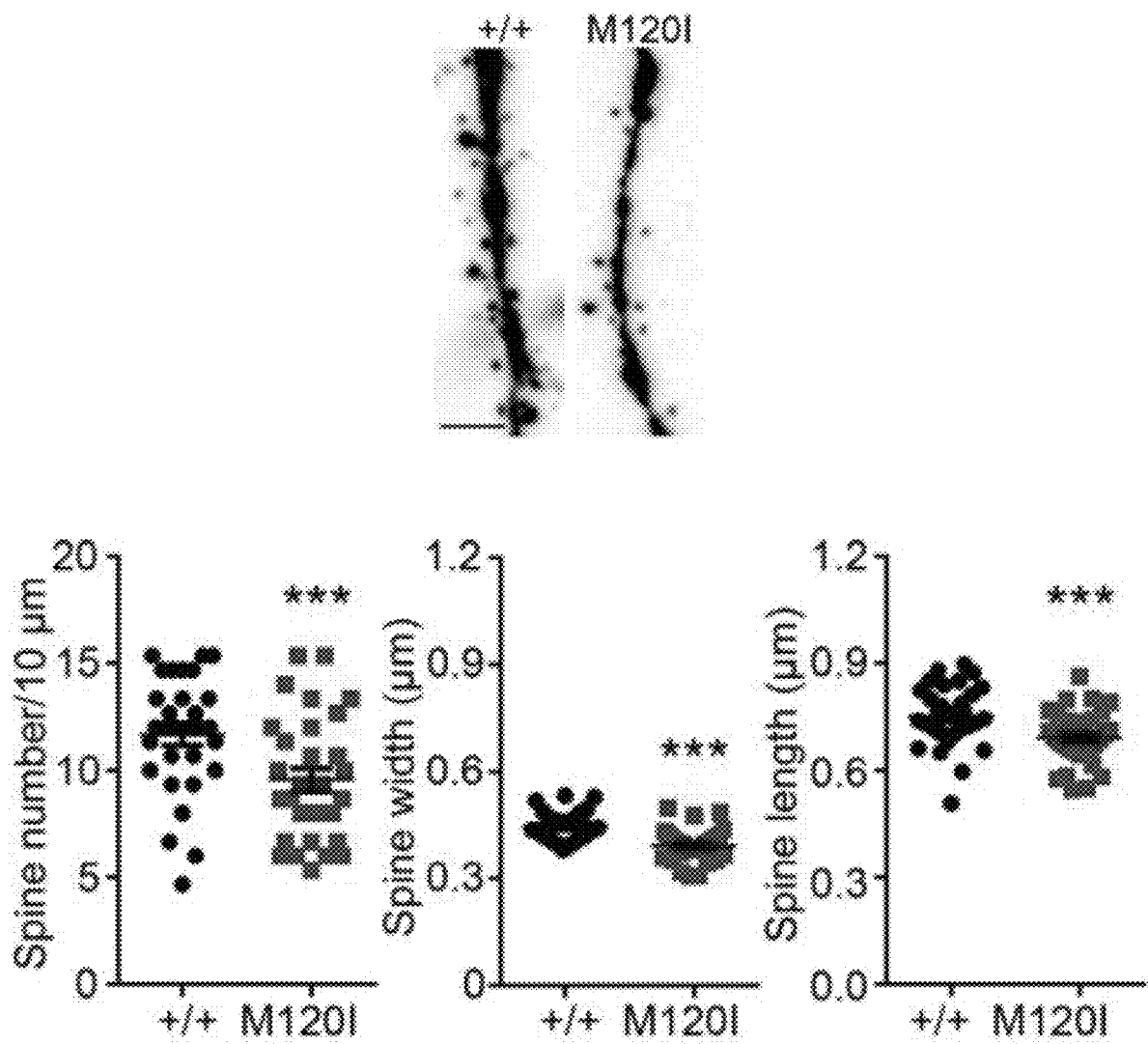
Figure 5D:
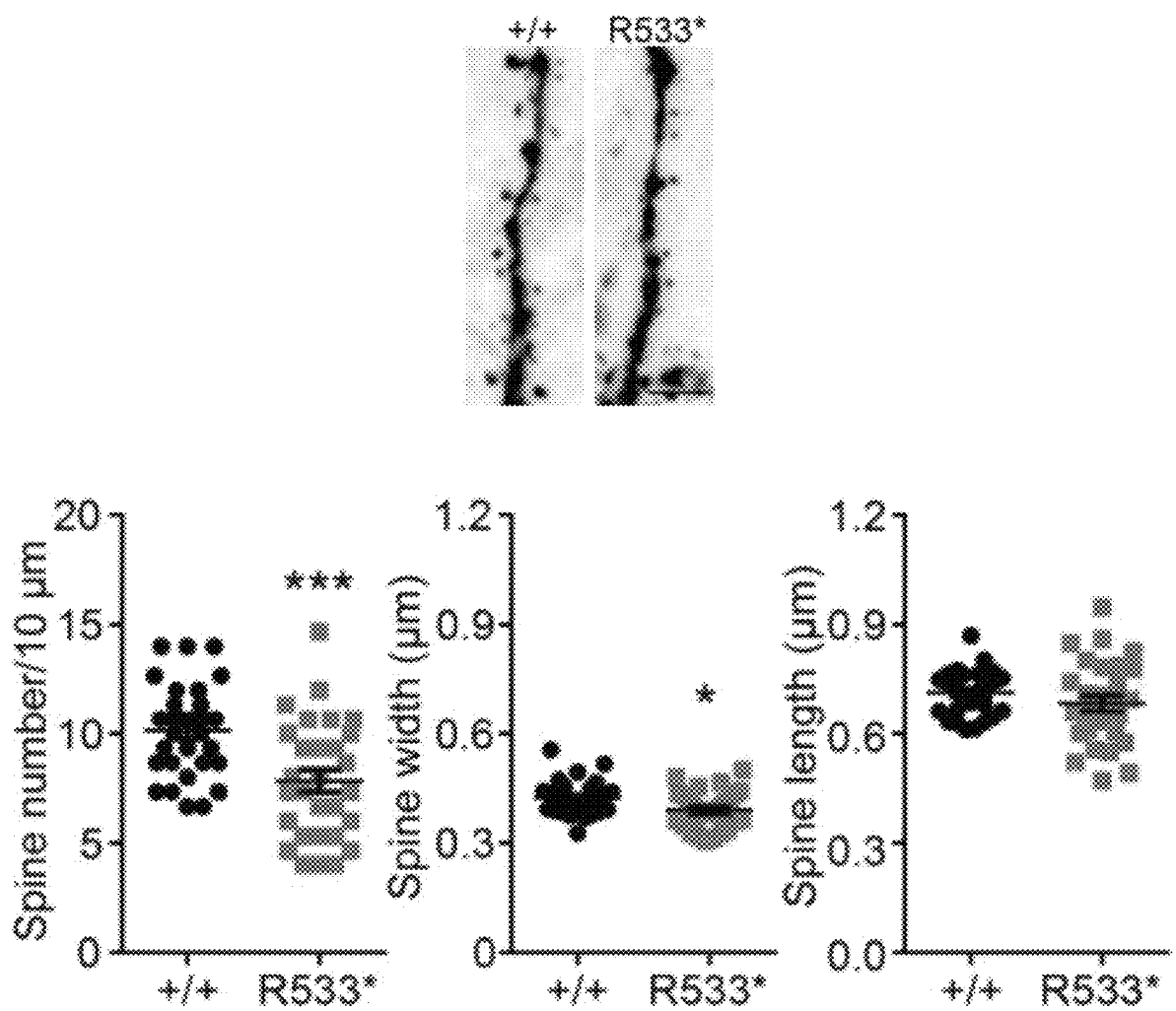

2.4 Cnbp2 Deficiency and ASD-Associated Mutations Result in Synaptic Defects In Vivo We then investigated whether dendritic spines of CA1 neurons are also sensitive to Cttnbp2 deficiency or mutation. To outline the neuronal morphology in vivo, we crossed our Cttnbp2-deficient mice with Thy1-eYFP transgenic mice (FIG. 5A). We found that both Cttnbp2-/- and M120I mutant CA neurons had fewer, smaller and shorter dendritic spines (FIG. 5B, FIG. 5C). For Cttnbp2+/-CA neurons, only the width of dendritic spine heads were shorter than that for wild-type CA neurons (FIG. 5B). For R533* mutant neurons, both dendritic spine density and width were reduced (FIG. 5D). Thus, consistent with the results of C-FOS expression (FIG. 4), the density and/or size of dendritic spines of hippocampal CA1 neurons are susceptible to Cttnbp2 deficiency or mutations.

Figure 5E:
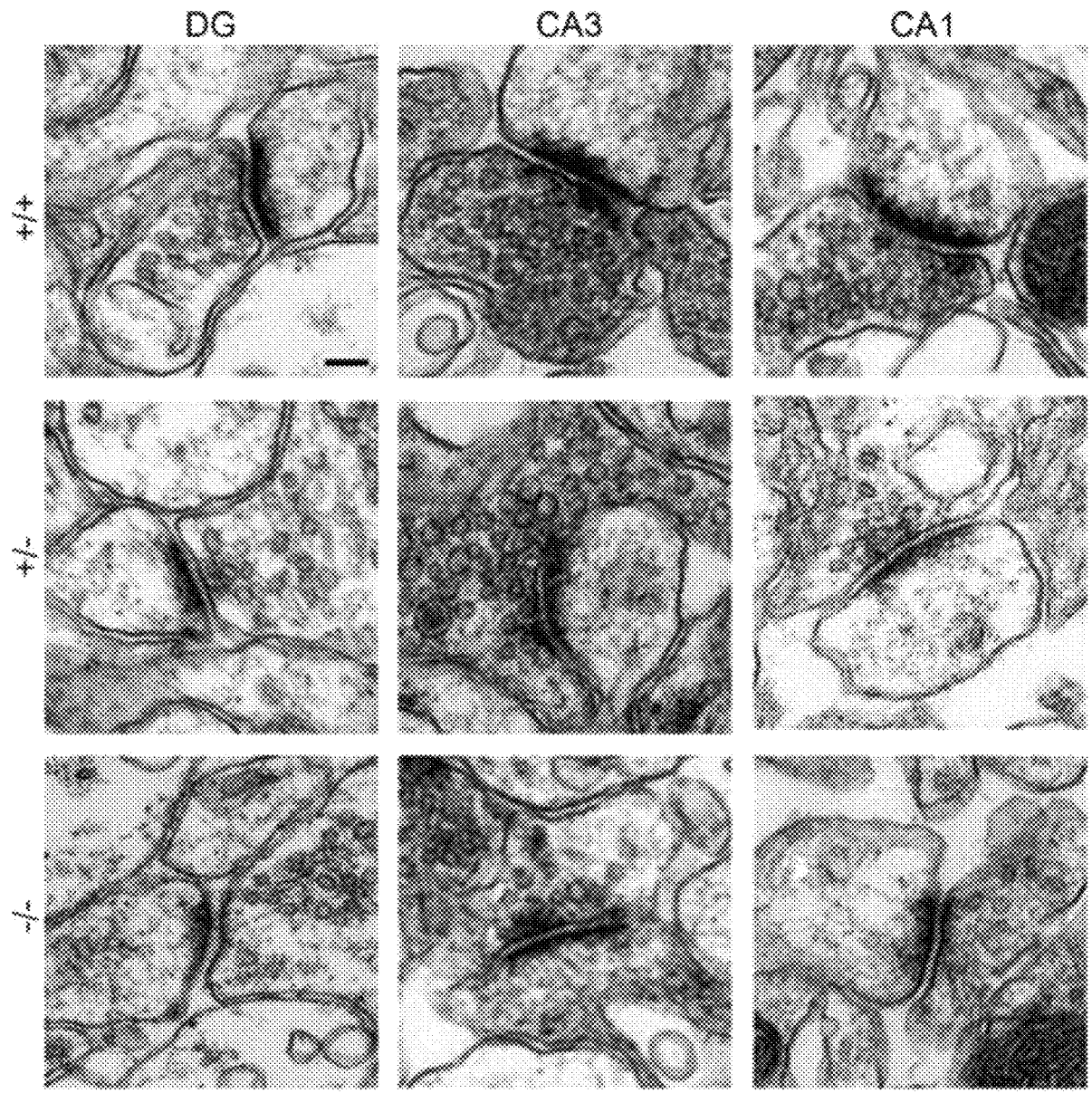
Figure 5F:
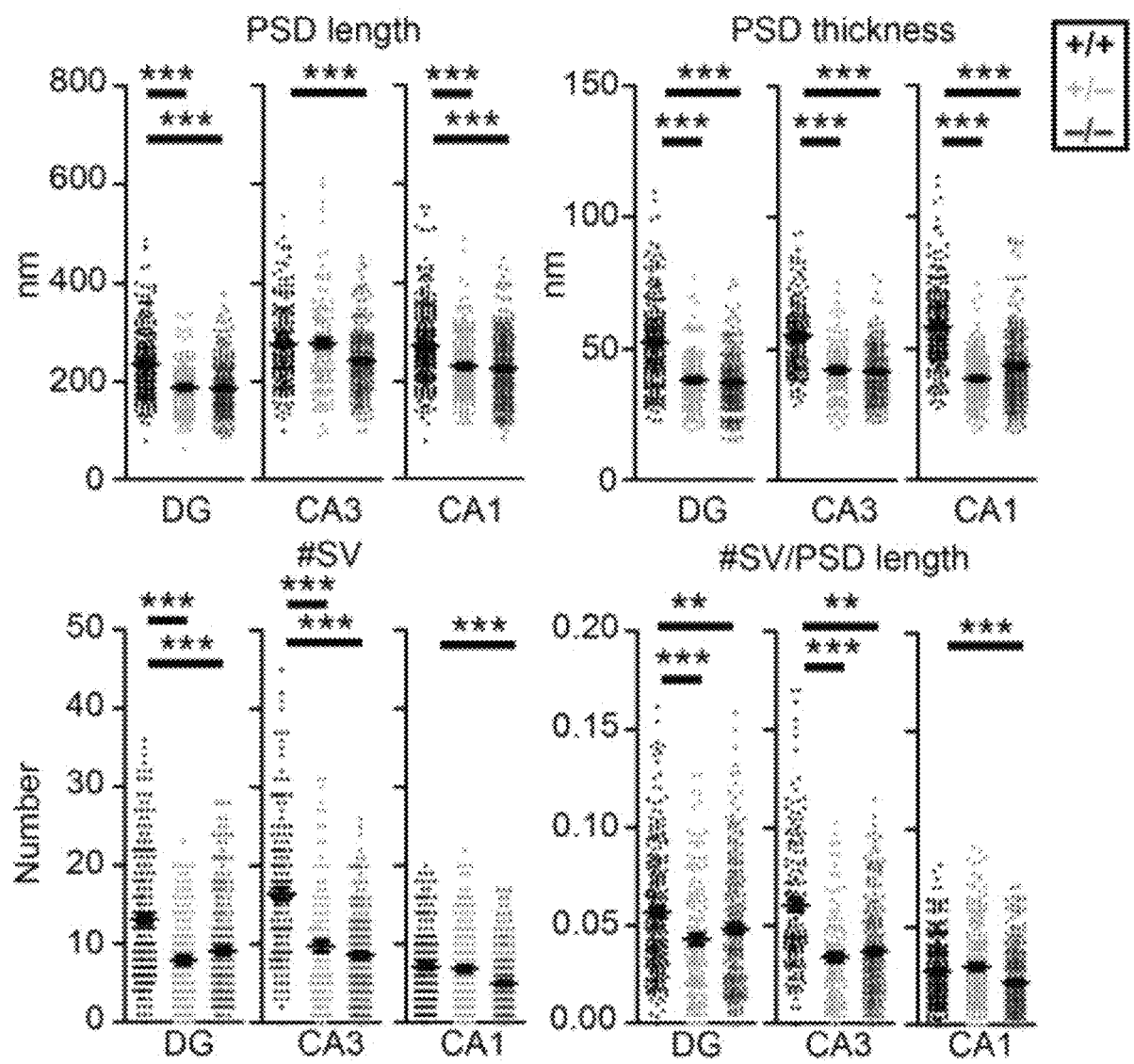

To further characterize the synaptic phenotype in Cttnbp2-deficient mice, we performed transmission electron microscopy (TEM) to analyze the ultrastructure of excitatory synapses of the dorsal hippocampus. We measured the length and thickness of postsynaptic density (PSD) and the number of presynaptic vesicles. Cttnbp2-/- neurons had shorter and thinner PSD and fewer synaptic vesicles compared with wild-type littermates at the dorsal dentate gyrus, CA1 and CA3 (FIG. 5E, FIG. 5F). Since both PSD length and vesicle number were reduced, we also calculated the ratio of vesicle number to PSD length and found that this ratio was lower in Cttnbp2-/- neurons (FIG. 5E, FIG. 5F). The phenotype of Cttnbp2+/- mice was again milder than that for homozygote mice (FIG. 5E, FIG. 5F). There was no difference with wild-type littermates for some parameters, such as the PSD length at CA3 and the vesicle number and ratio of vesicle number to PSD length at CA (FIG. 5E, FIG. 5F). These results suggest that the size of the PSD and the number of presynaptic vesicles are also affected by Cttnbp2 deficiency in a dosage-dependent manner.

Thus, consistent with the deficits of C-FOS expression in the hippocampus, our ultrastructure analyses also indicate that dendritic spines and PSD in the hippocampus are sensitive to Cttnbp2 deficiency.

2.5 Cnbp2 Deficiency Influences the Molecular Composition of Synapses

Figure 6A:
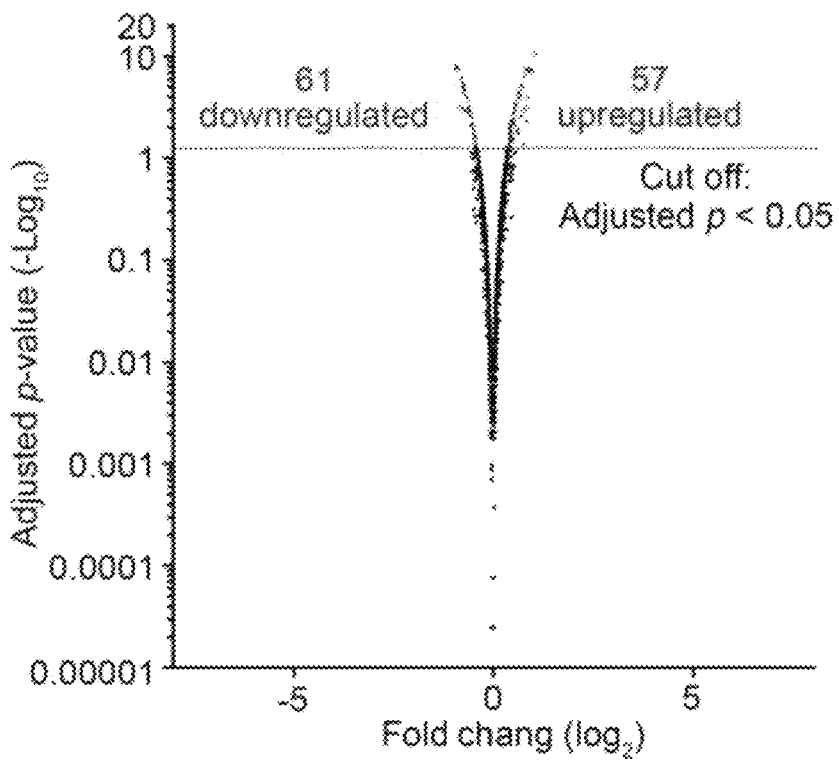
Figure 6B:
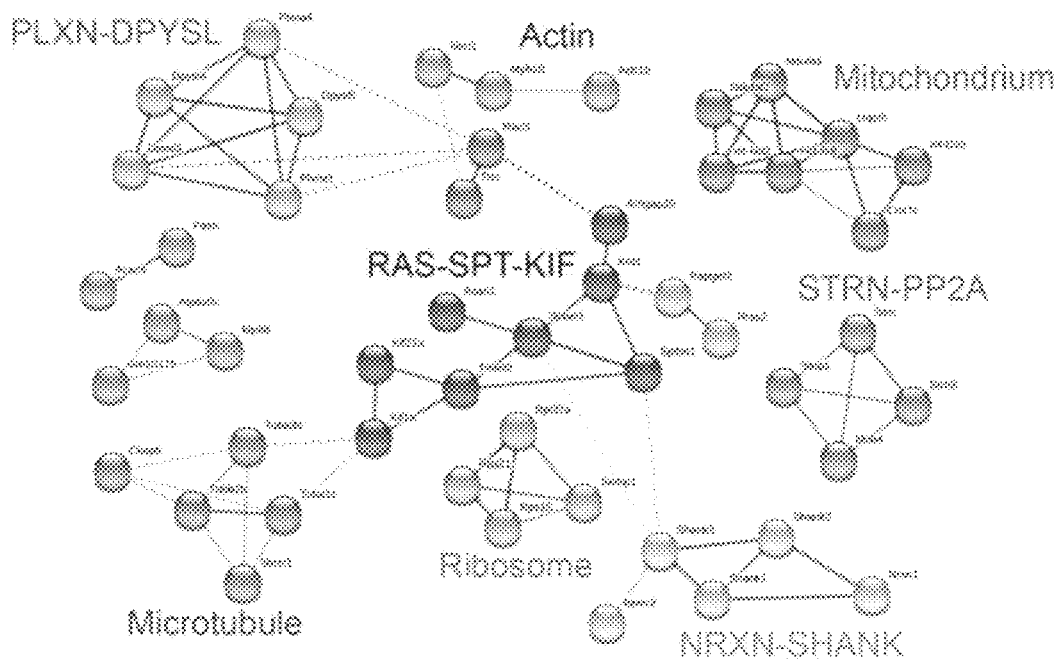

To further dissect the molecular deficits caused by Cttnbp2 deficiency, we purified the synaptosomal fractions from Cttnbp2-/- mice and wild-type littermates and analyzed the molecular composition of synaptosomes using a liquid chromatography-mass spectrometry (LC-MS-MS) technique. Using this approach, we identified more than 3000 protein species. Among them, 57 were upregulated and 61 were downregulated in Cttnbp2-/- mice using an adjusted p-value threshold of <0.05 (FIG. 6A). Protein network analysis indicated that these differentially expressed proteins were enriched in several protein networks, including striatin (STRN)/PP2A complex, SHANK family, plexin (PLXN)-CRMP pathway, microtubule and actin cytoskeletons and their associated proteins (including spectrins, SPTN) (FIG. 6B). Notably, some of these altered proteins were previously shown to directly or indirectly interact with CTTNBP2, such as SHANK3, STRN, MOB4, actin and microtubule [9-12]. Identification of these CTTNBP2-associated proteins supports the reliability of our proteomic study.

Figure 6C:
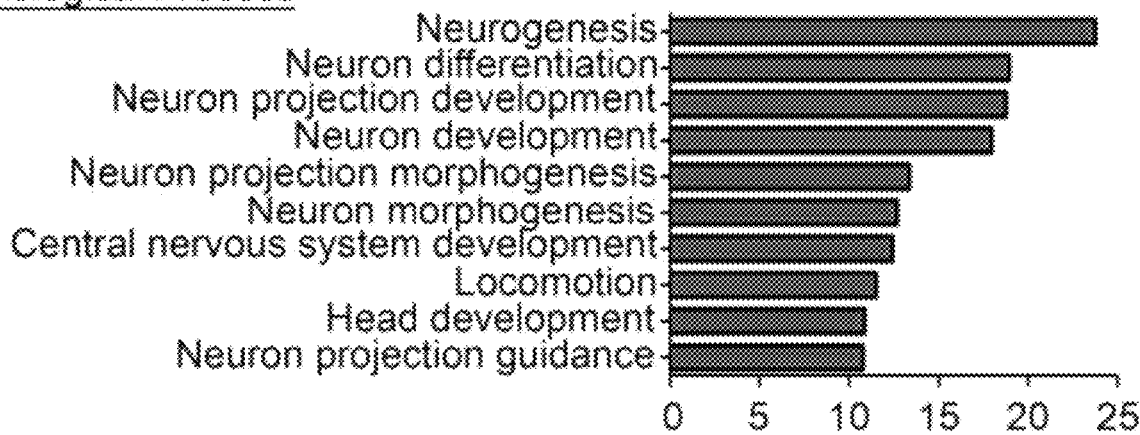
Figure 6C:
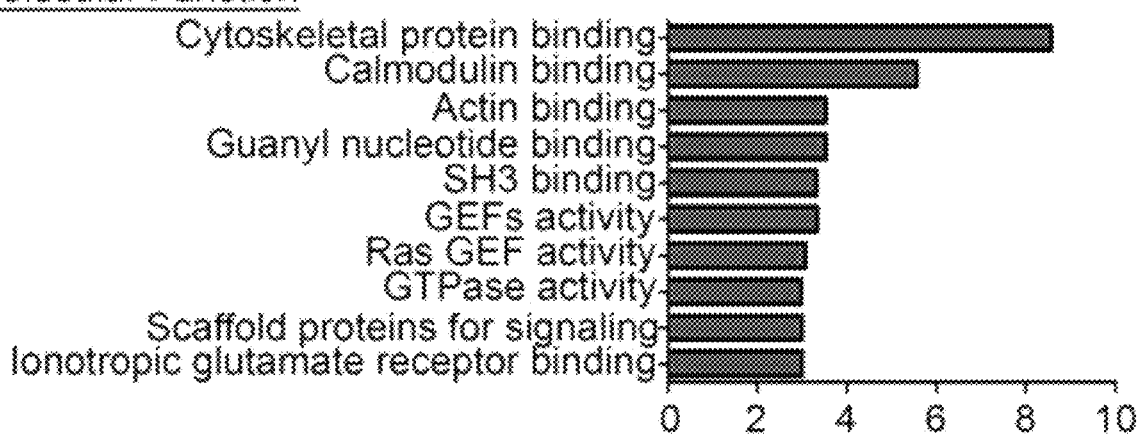
Figure 6C:
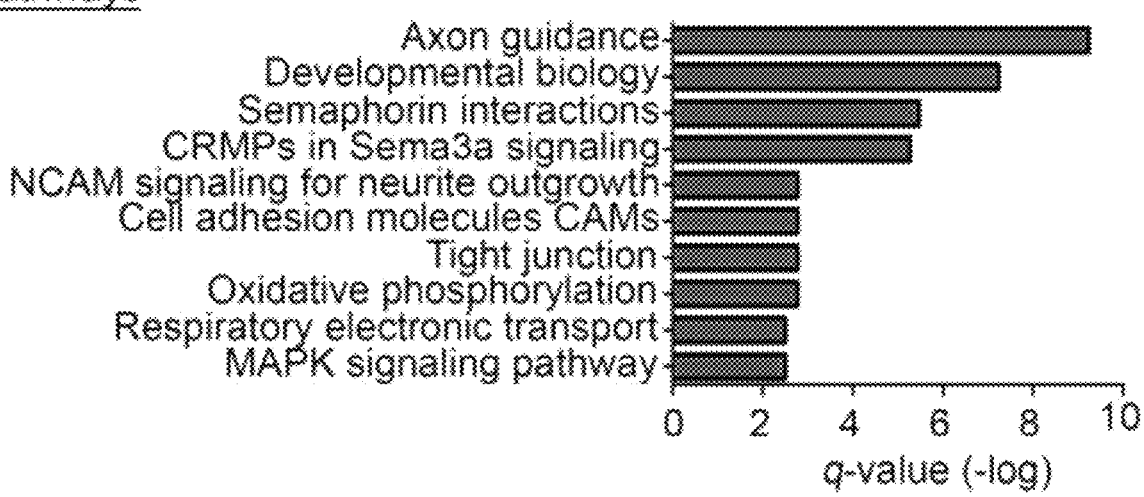

Gene ontology analysis further suggested that CTTNBP2-regulated proteins were associated with neural development and morphogenesis, functioning as cytoskeleton regulators and scaffold proteins for glutamate receptors and being involved in the pathways of axonal projection/guidance and cell-cell interaction (FIG. 6C). Moreover, 39 of these CTTNBP2-regulated proteins are associated with or are causative genes of disease, among which 28 are relevant to neurological disorders. Significantly, 21 of these proteins have been listed in the collections of SFARI and/or SPARK genes of ASD (FIG. 6D, FIG. 6E, htts://gene.sfari.omr/database/human-gene/and htts://simonsfoundation.s3.amazonaws.com/share/SFARI/SPARK Gene List). These analyses indicate that CTTNBP2 regulates synaptic expression of proteins encoded by disease-associated genes, especially ASD-associated genes.

Figure 7A:
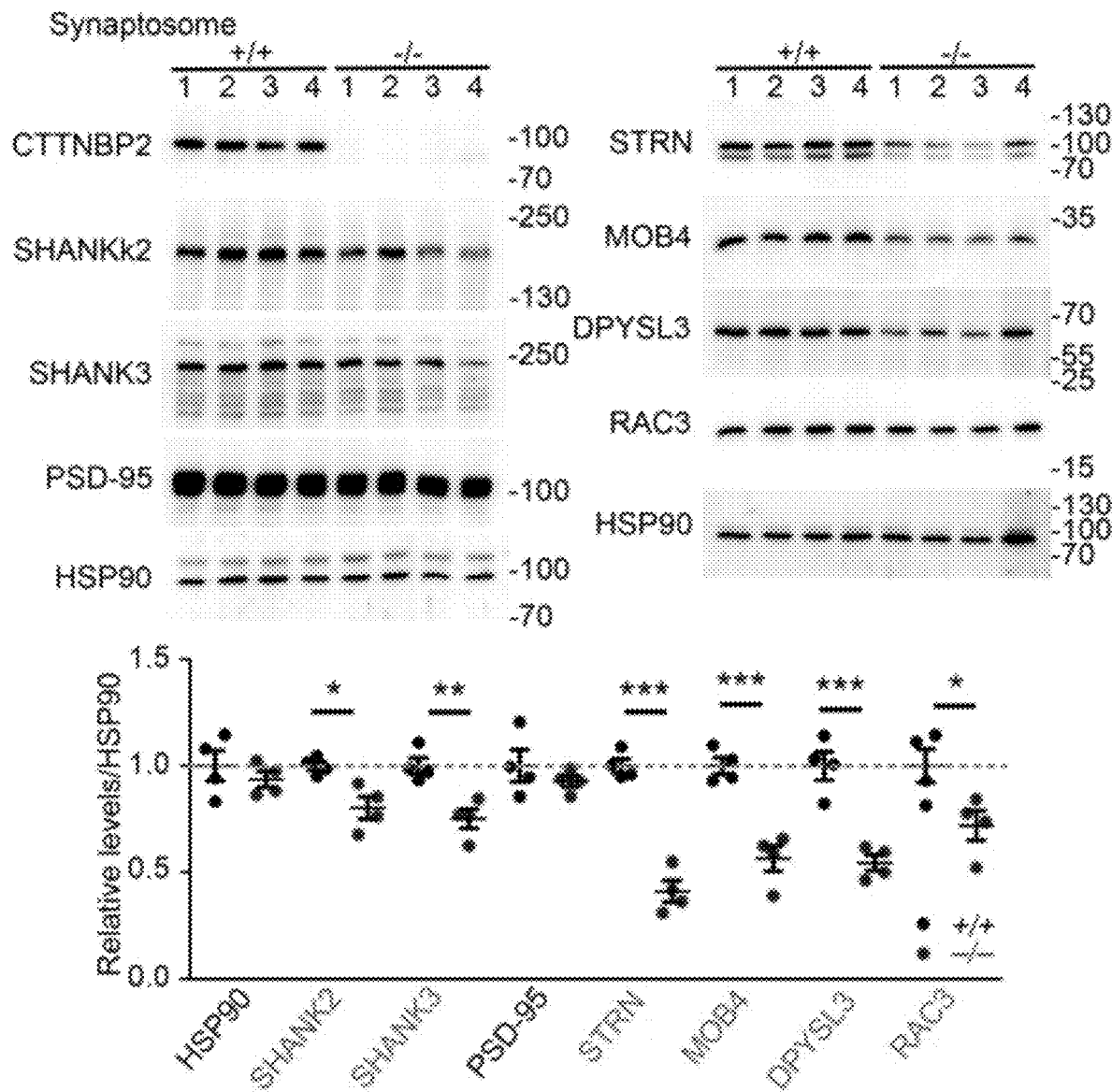
FIGS. 7A to 7E show differential expression of synaptic proteins in Cttnbp2−/− mice.
Figure 7B:
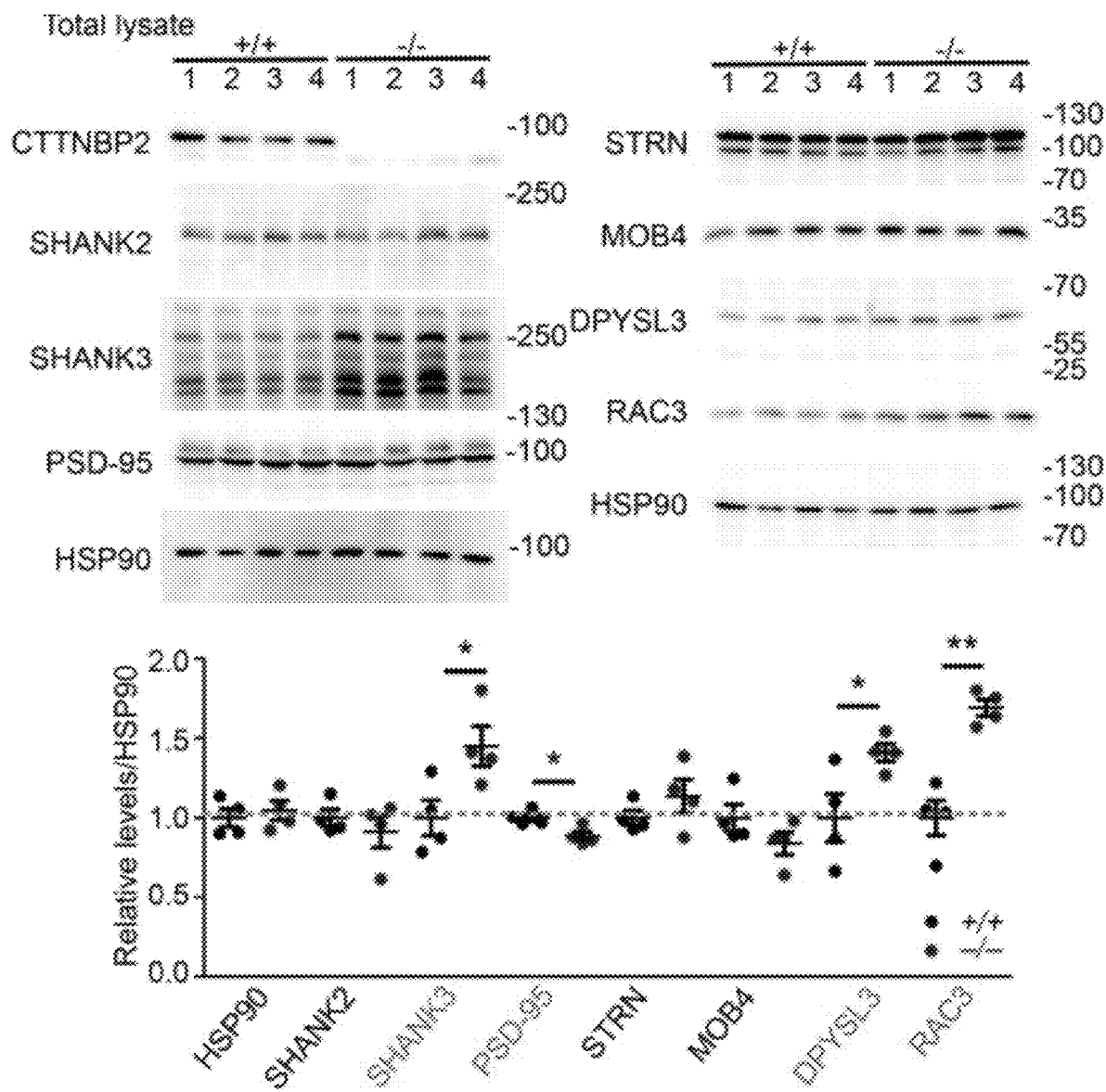

To validate our proteomic data, we performed immunoblotting using synaptosomal fractions. Based on the availability of specific antibodies, we endeavored to select one or two proteins from each of the protein networks shown in FIG. 5B. All six examined proteins—SHANK2, SHANK3, STRN, MOB4, DPYSL3 and RAC3—showed reduced expression in synaptosomal fraction purified from Cttnbp2-/- brains (FIG. 7A). These results confirm that Cttnbp2 deletion reduced the synaptic distributions of these six proteins, with this outcome being specific to Cttnbp2 deletion because protein levels of PSD-95 were not altered (FIG. 7A). We then investigated whether total levels of these proteins are affected by Cttnbp2 deletion. Immunoblotting showed that in contrast to their reduced levels in synaptosomal fractions, levels of SHANK3, DPYSL3 and RAC3 were actually increased in total homogenates of Cttnbp2−/− brains (FIG. 7B), likely a compensatory effect for reductions in synaptosomal fractions. Moreover, the total protein levels of PSD-95 were slightly reduced in Cttnbp2−/− brains and the protein levels of SHANK2, STRN and MOB4 were not affected in the total homogenates, further supporting the specific changes of total protein levels of SHANK3, DPYSL3 and RAC3. In addition, it would seem the mechanisms of synaptic targeting and/or regulated expression of these synaptic proteins are different.

Figure 7C:
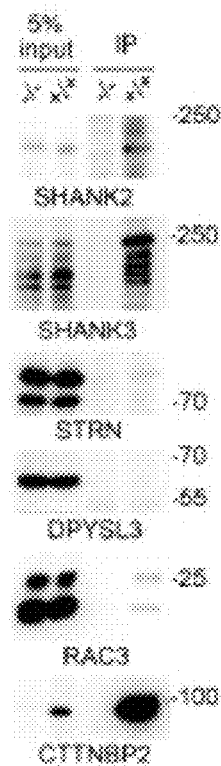

We then investigated whether CTTNBP2 associates with these synaptic proteins. It has previously been shown that CTTNBP2 forms a complex with STRN and SHANK3 [10, 11]. Our co-immunoprecipitation using CTTNBP2 antibody also supports an association of CTTNBP2 with SHANK3 and STRN in synaptosomal fractions purified from mouse brains (FIG. 7C). Moreover, SHANK2 and RAC3, but not DPYSL3, were also co-immunoprecipitated by CTTNBP2 antibody (FIG. 7C). The co-immunoprecipitation results were specific for CTTNBP2 because the signals were not present in lysates purified from Cttnbp2−/− brains (FIG. 7C). These results suggest that CTTNBP2 controls the synaptic distribution of the aforementioned proteins via at least two mechanisms, one of which is likely mediated by protein-protein interaction and the other remains unknown but is likely caused by indirect signaling or other factors.

Figure 7D:
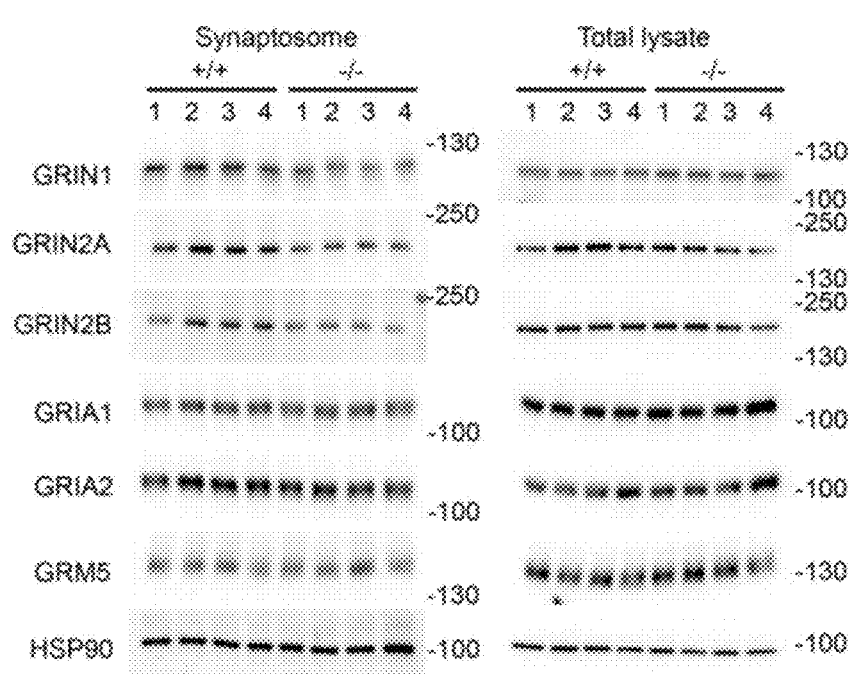
Figure 7E:
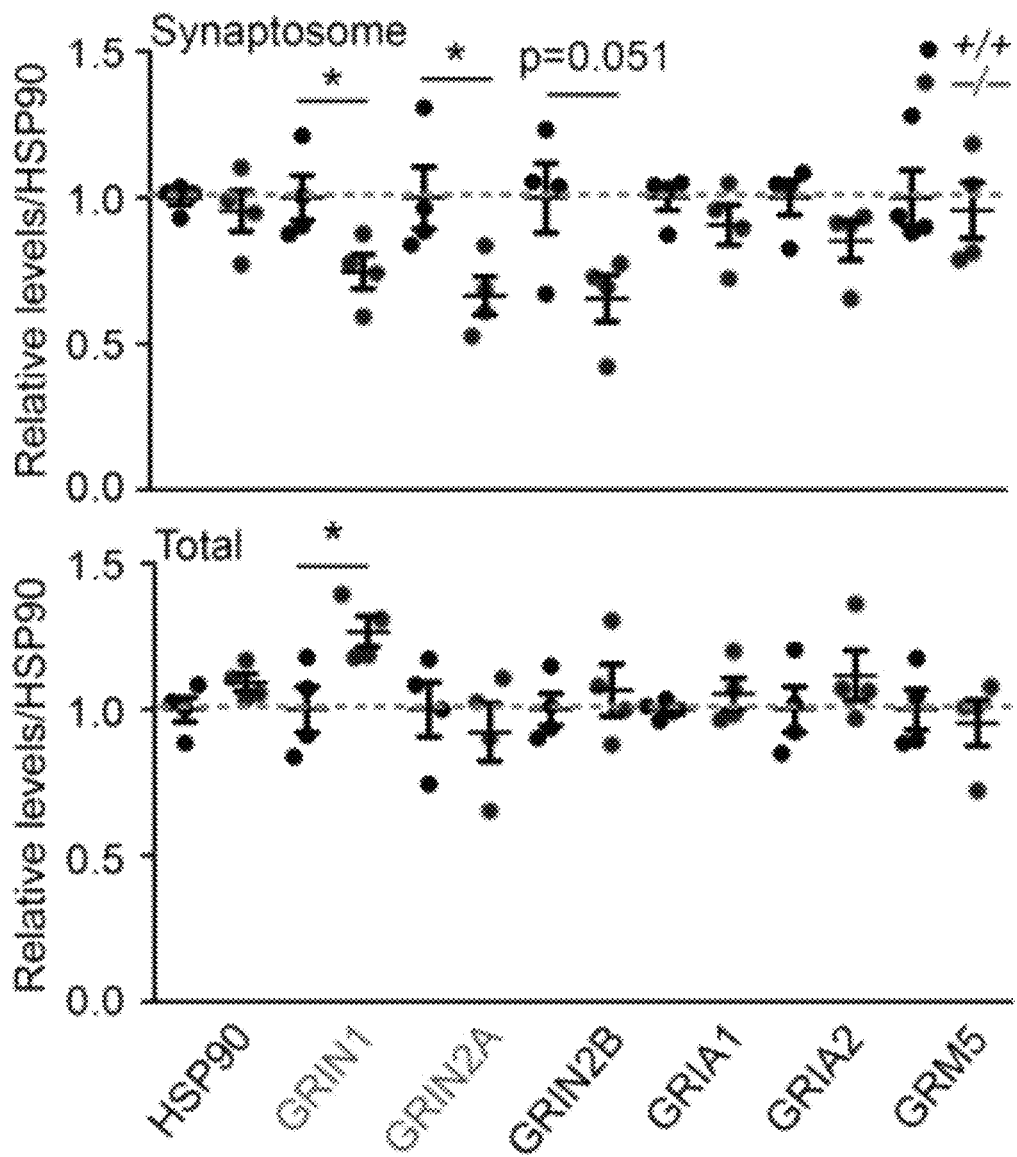

SHANK2 and SHANK3 are critical scaffold proteins for glutamate receptors at excitatory synapses [14-16]. STRN and MOB4 form a complex to regulate the subcellular distribution of PP2A, a critical phosphatase at excitatory synapses [17, 18]. Reduced levels of SHANK2, SHANK3, STRN and MOB4 proteins in synaptic fractions suggests glutamatergic synapses are likely dysregulated or dysfunctional in Cttnbp2−/− mice. To test that possibility, we first investigated the expression levels of glutamate receptors by means of immunoblotting. Among six different glutamate receptors we assessed (including GRIN1, GRIN2A, GRIN2B, GRIA1, GRIA2 and GRM5), we found that the protein levels of GRIN1 and GRIN2A (critical NMDAR subunits) were reduced in the synaptosomal fractions of Cttnbp2−/− brains (FIG. 7D, 7E), even GRIN1 was slightly upregulated in total lysate (FIG. 7D, FIG. 7E). Thus, NMDAR is particularly sensitive to Cttnbp2 knockout.

Based on our proteomic, immunoblotting and immunoprecipitation analyses, we suggest that synaptic proteins, including NMDAR and its downstream scaffolds (i.e. SHANK2 and SHANK3) and signaling proteins (STRN and MOB4), are dysregulated by Cttnbp2 knockout.

2.6 Zinc Supplementation Ameliorates Synaptic Protein Expression and Social Deficits of Cnbp2−/− Mice To validate the role of the NMDAR pathway in Cttnbp2 deficiency, we considered two sets of rescue experiments, the first of which involved zinc supplementation. Zinc deficiency is known to be a critical environmental factor linked to ASD [19-23]. Zinc regulates NMDAR conductivity either by directly binding to GRIN1 and GRIN2A [24] or by enhancing SRC kinase activity to phosphorylate NMDAR [25]. In addition to its effects on NMDAR, zinc also binds SHANK2 and SHANK3, and it regulates their synaptic distribution and functions in neurons [26-30]. MOB4 is also a zinc-binding protein, but the exact function of zinc-binding for MOB4 remains elusive [31, 32]. Our results indicate that CTTNBP2 likely forms complex(es) with and regulates the synaptic expression of SHANK2, SHANK3, STRN, MOB4 and RAC3 and thereby modulates synaptic expression and signaling of NMDAR. Thus, we investigated if zinc supplementation ameliorates the defects caused by Cttnbp2 knockout. To do so, we first confirmed that dietary zinc supplementation for 7 days is sufficient to increase the concentration of zinc in brains (FIG. 8A). Immunoblotting was then performed to examine the protein levels in synaptosomal fractions following zinc treatment. We found that zinc supplementation in drinking water for 7 days increased the expression levels of CTNBP2-associated proteins (SHANK2, SHANK3, STRN, MOB4, RAC3 and cortactin), as well as NMDAR (GRIN1 and GRIN2B, but not GRIN2A), in synaptosomal fractions of Cttnbp2−/− mouse brains (FIG. 8B). However, synaptic levels of DPYSL3 were reduced in mice that drank zinc-supplemented water (FIG. 8B). Levels of GRIA1 and GRIA2 were not noticeably altered by zinc supplementation (FIG. 8B). These analyses suggest that zinc supplementation specifically enhances synaptic expression of a subset of proteins in Cttnbp2−/− mouse brains.

Figure 8D:
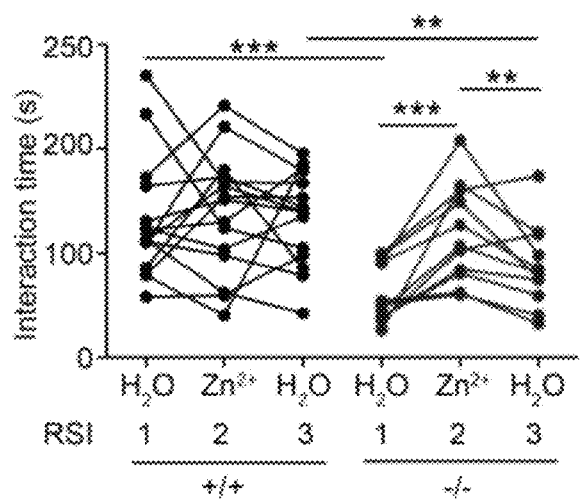
Figure 8E:
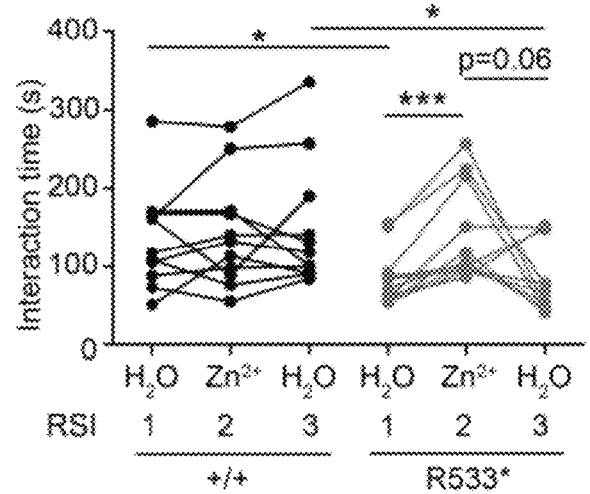

We then investigated the effect of zinc supplementation on social defects of Cttnbp2−/− mice. Mice were subjected to three consecutive RSI tests at 1-week intervals, starting at week 9 (FIG. 8C). Before conducting the second RSI, zinc was added to drinking water for 7 days (adopting the same treatment regime for our immunoblotting experiments). After the second test, zinc supplementation was discontinued so daily zinc intake returned to normal for 7 days. A third RSI was then performed at week 11. Thus, the first RSI test indicates social behavior in the absence of zinc supplementation, the second RSI test represents the effect of zinc supplementation, and the third RSI test assesses whether the effect of zinc supplementation is long-lasting. Similar to the results shown in FIG. 1G, Cttnbp2−/− mice showed reduced social interaction compared with wild-type littermates in the first RSI test (FIG. 8D). After zinc supplementation for 7 days, both Cttnbp2−/− and R533* mice spent significantly longer interacting with the unfamiliar mouse in the second RSI test (FIGS. 8D-8E), indicating that zinc supplementation indeed ameliorates social behaviors of Cttnbp2−/− and R533* mice. Upon discontinuing zinc supplementation in drinking water, we observed that social interaction of Cttnbp2−/− mice was reduced in the third RSI test (FIG. 8D). For R533* mice, their social interactions in the third RSI tended to be lowered, but it was not statistically different from those of the second RSI (FIG. 8E). Zinc supplementation did not noticeably influence the social behaviors of wild-type mice (FIG. 8D), nor did it alter volumes of water drunk daily or body weight during the experimental period. These results suggest that zinc supplementation ameliorates social interaction deficits of Cttnbp2−/− mice, but the effect is not long-lasting.

Figure 9A:
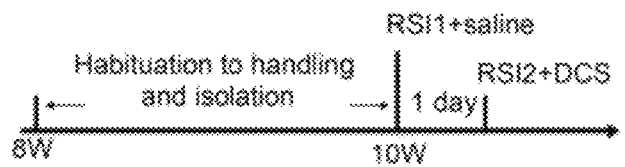
FIGS. 9A to 9D shows D-cycloserine improves the social behaviors of Cttnbp2 knockout and mutant mice.
Figures 9B, 9C:
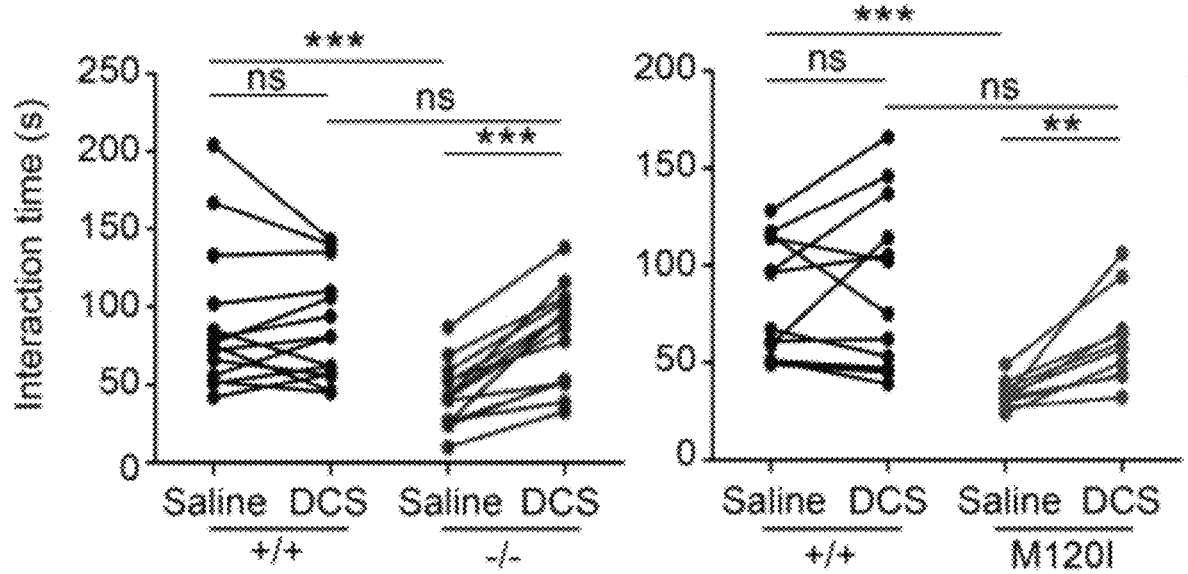
Figure 9D:
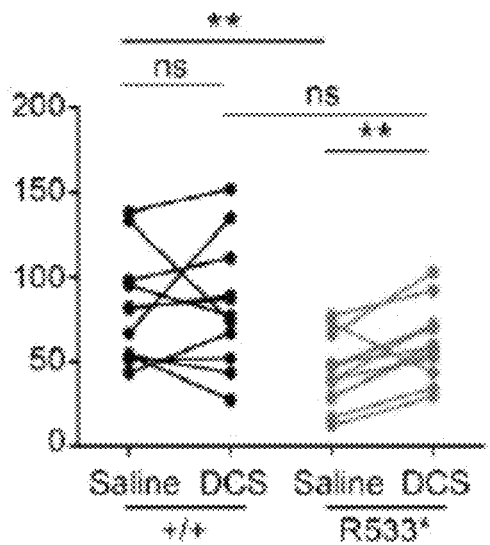

2.7 D-Cycloserine Treatment Improves Social Interaction of Cttnbp2-Deficient Mice The second experiment we conducted to validate the role of NMDAR was D-cycloserine rescue. D-cycloserine, a coagonist of NMDAR, increases NMDAR conductivity [33, 34]. Previous studies indicated that D-cycloserine administration improves social behaviors of Shank2−/− and Tbr1+/− mice, both characterized by reduced NMDAR activity [35-38]. If reduced NMDAR levels and/or impaired NMDAR signaling are indeed critical for Cttnbp2 deficiency, we anticipated that increasing NMDAR activity via D-cycloserine treatment would have a beneficial effect on the social behaviors of Cttnbp2-deficient mice. To test that possibility, we performed two consecutive RSI tests on the same mice. Before conducting the first RSI test, we injected mice with saline. One day later, we injected D-cycloserine 30 min before conducting the second RSI test (FIG. 9A). Compared with saline control, D-cycloserine treatment increased social interaction behavior of Cttnbp2−/− mice to levels comparable to those of wild-type littermates (FIG. 9B). We also investigated the effect of D-cycloserine administration on M120I and R533* mutant mice. As for Cttnbp2−/− mice, D-cycloserine treatment also improved social interaction behaviors of M120I and R533* mutant mice (FIGS. 9C-9D). These results suggest that NMDAR function and activity is crucial for the social behaviors controlled by CTTNBP2.

2.8 Administration of a Combination of BCAAs, Zinc and Serine in Drinking Water

Animals

Nf1$^{+/-}$ mice were purchased from Jackson Laboratory (Stock No: 002646). Tbr1$^{+/-}$ mice were generated using traditional gene recombination [52]. Cttnbp2$^{-/-}$ mice, Cttnbp2 R533* mutant mice and Cttnbp2 M120I mice were generated using TALEN and CRISPR/Cas9 approaches. All mouse lines were maintained by backcrossing to C57BL/6JNarl. Mice were housed in the animal facility of the Institute of Molecular Biology, Academia Sinica, under controlled temperature and humidity and a 12 h light/12 h dark cycle with free access to water and chow (LabDiet #5K54). Animal experiments were performed when mice were around 2-3 months old. Data collection and analysis were conducted randomly and blind without knowing the genotype and treatment. All animal experiments were performed with the approval of the Academia Sinica Institutional Animal Care and Utilization Committee (protocol No 14-11-1059). Only male mice were used for behavioral analyses. All of the behavioral tasks were performed with two-month-old male mice habituated in the behavior room for at least one week prior to undertaking tasks. One of the core symptoms of ASD is social deficits. To investigate the relevance of these three genes with ASD in mouse models, reciprocal social interaction test and three-chamber test were used to analyze mutant mice. The results showed that all mutant mice exhibited social deficits, supporting the feasibility of using these mouse models for ASD study.

Figure 10:
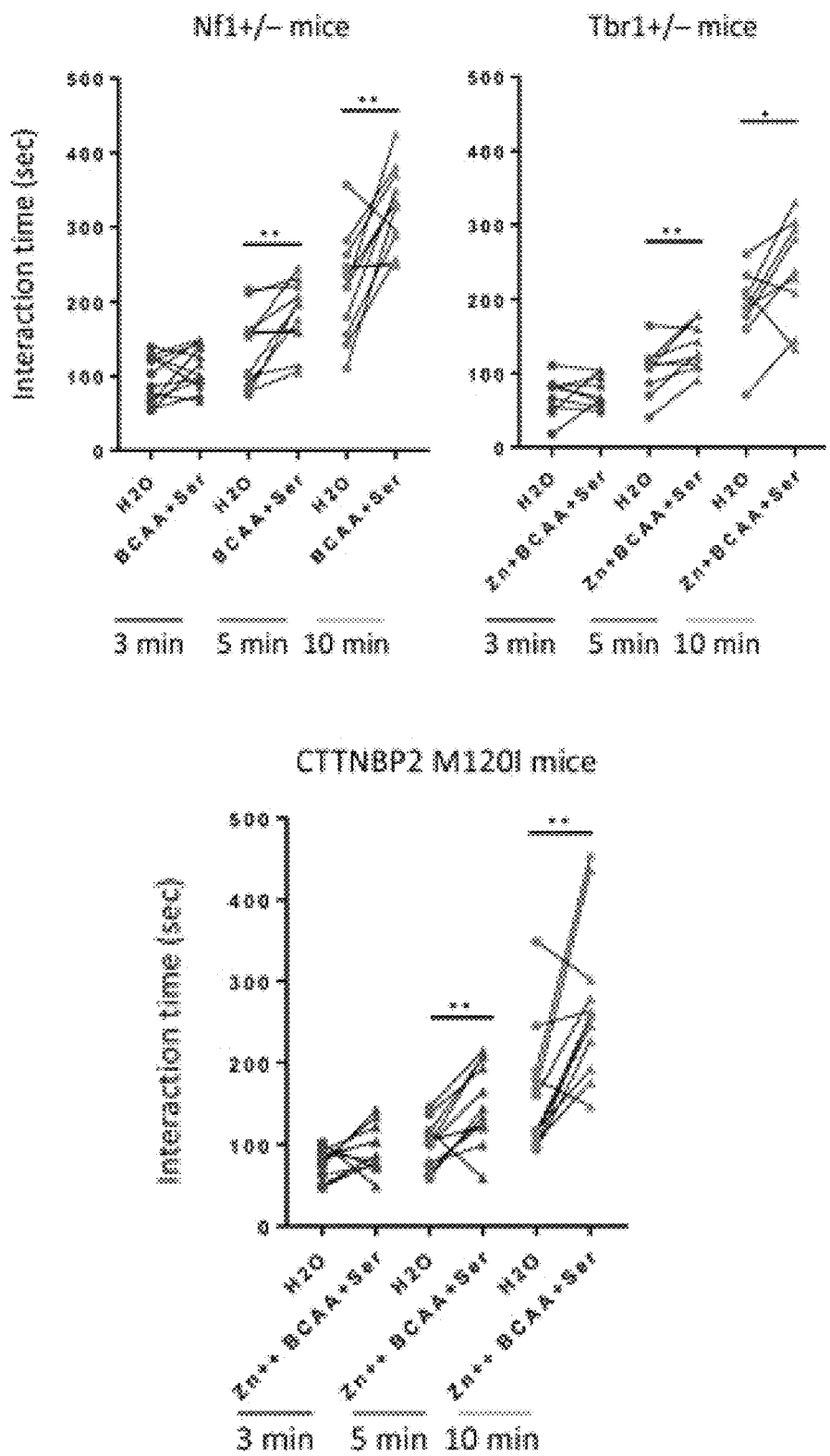
FIG. 10 shows that the supplement mixture benefits multiple different ASD mouse models. Nf1+/−, Tbr1+/− and CTTNBP2 M120I mice were used to investigate the effect of supplement mixture containing branched-chain amino acids (BCAA, 0.45%), serine (1%) and zinc (20 ppm) on reciprocal social interaction. BCAA contains leucine, isoleucine and valine (2:1:1, i.e. Leu, 0.225%; Ile, 0.112%; Val, 0.112%). The interaction time of test mice with stranger was measured during the first three and five and entire ten min. Social interaction of these three ASD mouse models was increased after 7-day mixture supplementation compared with regular drinking water. The data of the same mouse are linked with black lines. * P<0.05;  P<0.01; * P<0.001; paired t test.

We investigated whether a supplement mixture that contains zinc, branched-chain amino acid (BCAA) and serine benefit social behaviors of ASD mouse models. We tested three different ASD mouse models, i.e. Nf1+/−, Tbr1+/−, and Cttnbp2 M120I mice. Before taking supplement, mice were subjected to the first reciprocal social interaction test. After taking supplement for 7 days, mice were analyzed again using reciprocal social interaction to evaluate the effect of nutritional supplementation. We found that when BCAA (0.45%), serine (1%) and zinc (20 ppm) were provided in drinking water for 7 days, Nf1+/−, Tbr1+/− and CTNBP2 M120 mice all spent longer time to approach and interact with stranger (FIG. 10).

Figure 11:
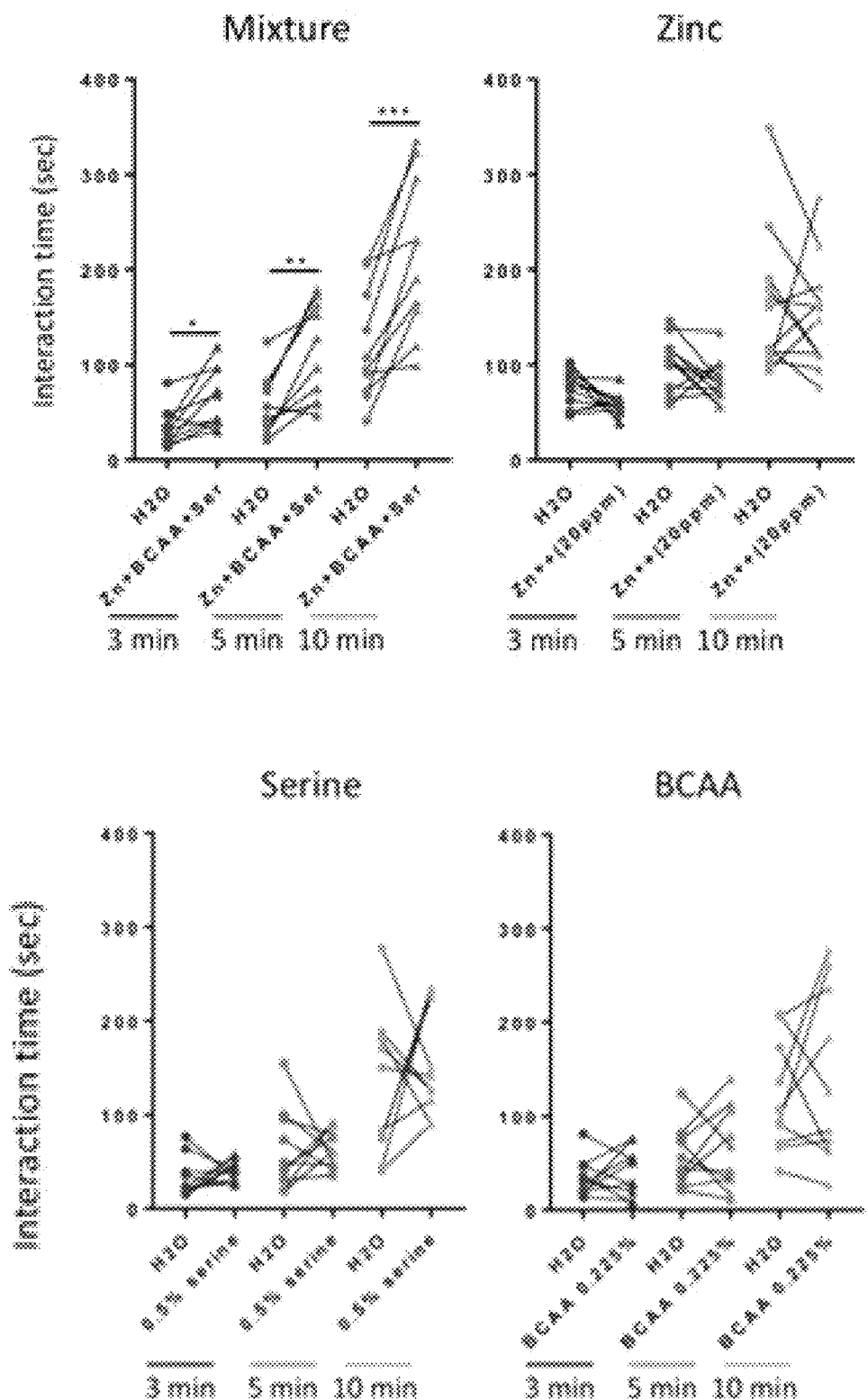
FIG. 11 shows that the mixture that contain lower doses of zinc, serine and branched chain amino acid (BCAA) still enhances social interaction of CTTNBP2 ASD-linked mutant mice. The concentration of supplement mixture was further reduced, i.e. serine (0.5%) and BCAA (0.225%). Zinc was maintained at the concentration of 20 ppm. Compared with behaviors examined before supplementation, lower dose supplement mixture still exhibited a beneficial effect on social interaction. The interaction time within the first three and five and total ten min of each mouse were measured. BCAA contains leucine, isoleucine and valine (2:1:1, i.e. Leu, 0.113%; Ile, 0.056%; Val, 0.056%). When zinc (20 ppm), BCAA (0.225%) and serine (0.5%) was individually provided to CTTNBP2 M120I mice. Our data showed that single supplement did not noticeably alter social behaviors of CTTNBP2. The data of the same mouse are linked with black lines. * P<0.05;  P<0.01; * P<0.001.

We further tested whether reduction of the concentration of supplements can still improve the social interaction of ASD mutant mice. We reduced the concentration of BCAA and serine to the half amounts and performed RSI to analyze the effects. We found that CTTNBP2 M120I mice with the lower concentration of supplement mixture still increased the social interaction time (FIG. 11). However, when zinc, BCAA and serine were individually provided to CTNBP2 M120I mice, the treatment did not improve social interaction of mutant mice, suggesting the additive or synergistic effect of zinc, BCAA and serine supplementation on improving social interaction (FIG. 11).

In fully supplemented drinking water, the lowest daily intake amounts for each supplement for mice are following:

| Mice | Human (adult, equivalent amounts = mice amount x3/37) |
|---|---|
| Leucine: 0.225 g/kg BW | Leucine: 0.018 g/kg BW |
| Isoleucine: 0.1125 g/kg BW | Isoleucine: 0.009 g/kg BW |
| Valine: 0.1125 g/kg BW | Valine: 0.009 g/kg BW |
| Serine: 1 g/kg BW | Serine: 0.081 g/kg BW |
| Zinc intake: 4 mg/kg BW | Zinc intake: 0.3243 mg/kg BW |

3. Discussion

In this report, we characterize the function of CTTNBP2 in vivo using mouse genetic models. Behavioral assays of our mutant mice show that CTTNBP2 is required for social behaviors, supporting the relevance of CTTNBP2 to ASD. Our analyses further indicate that knockout and ASD-associated mutations alter the density and size of dendritic spines, the size of PSD, and the number of synaptic vesicles in the brain, implying that Cttnbp2 deficiency causes synaptic dysfunction. Proteomic and immunoblotting analyses further revealed altered levels of a subset of synaptic proteins in Cttnbp2−/− mouse brains, including NMDARs and their downstream scaffold and signaling proteins. Zinc supplementation and D-cycloserine to respectively restore synaptic expression of CTTNBP2-regulated proteins and increase NDMAR activity improved social interaction behaviors of Cttnbp2-deficient mice. Our study reveals the relevance of CTTNBP2 to social behaviors and the molecular defects caused by Cttnbp2 deficiency, and also presents potential therapeutics for the social deficits exhibited by Cttnbp2 mutation.

Our previous study showed that only the short form of CTTNBP2 is detectable in neurons, based on RT-PCR and immunoblotting data [9]. In that study, we used an antibody recognizing the P-rich domain of CTTNBP2 [9]. In this report, we generated a new antibody recognizing the N-terminal region of CTTNBP2. The antigens used to generate these two antibodies are shared among all three forms of CTTNBP2 but, as reported previously [9], we only detected a single protein species at ~90 KDa (the short form of CTTNBP2) in the current study (FIG. 1B, FIG. 1D, FIG. 7A, FIG. 7B). These data strengthen the notion that the short form is the predominant protein product of Cttnbp2 in neurons.

Of the seven ASD-associated mutations located within the short form of CTTNBP2 that we assessed, we found that the M120I and R533* mutations impaired dendritic spine formation, both in vitro and in vivo, and reduced social interaction. Thus, our mouse model study suggests that the M120I and R533* mutations are disease causative. Interestingly, based on behavioral features and neuronal morphology, the four genetic mouse models used in this report can be classified into two groups: 1) Cttnbp2−/− and M120I; and 2) Cttnbp2+/− and R533*. The phenotypes of Cttnbp2−/− and M120I mutant mice are much more obvious than those of Cttnbp2+/− and R533* mutant mice. Since R533* mutation results in a truncated protein, which was unable to interact with cortactin, the allele might mimic a null allele to give rise to phenotypes similar to those of Cttnbp2+/− mice. The M120I residue is located in the NCC domain. Our co-immunoprecipitation analyses suggest a reduced interaction between M120I mutant and the P-rich domain and the involvement of the N-terminal region in regulating the interaction with cortactin via the C-terminal motif. Moreover, the NCC motif is a homo- and hetero-oligomerization domain. It is possible that M120I mutation also alters the oligomerization of CTTNBP2 and has the dominant-negative effect of reducing the activity of wild-type proteins encoded by the other normal allele. To investigate these possibilities, further studies of the molecular defects caused by the M120I and R533* mutations must be performed. Since CTTNBP2 also regulates dendritic arborization [12], it will be interesting to investigate in future if these mutations influence dendritic arborization and modulate neuronal function.

In addition to contextual and spatial memory, the hippocampus is also involved in social interaction and social memory [39]. It is well known that the ventral hippocampus, including ventral CA1 neurons, is required for social interaction [40, 41]. Recently, the involvement of dorsal CA1 in social memory has also been evidenced [39]. Interestingly, our C-FOS staining indicated that the hippocampus, particularly the dorsal CA1 region, is involved in CTNBP2-mediated social interaction. Our morphological analyses also suggest that dendritic spines and the PSD of dorsal CA neurons are affected by Cttnbp2 deficiency. Thus, synaptic defects of dorsal CA1 neurons likely contribute to the phenotypes of reduced neuronal activation and impaired social behaviors of Cttnbp2-deficient mice we report here. Since CTTNBP2 is widely expressed in different brain regions, especially the forebrain, other regions are also likely to be involved in reciprocal social interaction, even though the dorsal CA1 region is the most susceptible to Cttnbp2 deficiency. It would be also interesting to explore in the future if Cttnbp2 regulates behaviors other than social ones.

Our proteomic analyses indicate that Cttnbp2 knockout alters synaptic expression of a subset of proteins. Among 118 differentially expressed proteins, 21 of them are associated with ASD. CTTNBP2 likely controls synaptic expression of these proteins to regulate ASD phenotypes. Based on our analyses, different mechanisms are involved in regulating synaptic expression of these differentially expressed proteins. The first mechanism is likely via protein-protein interactions with CTTNBP2. As our co-immunoprecipitation experiments showed that SHANK2, SHANK3, STRN and RAC3 were all precipitated with CTTNBP2 antibodies, removal of CTTNBP2 may impair synaptic targeting of these proteins and also their related proteins, such as NMDARs. When we provided zinc supplementation to increase synaptic expression of SHANKs, we found that synaptic expression of all SHANKs, NMDAR and other CTTNBP2-associated proteins was increased. This outcome also suggests that these proteins may form a large complex or are regulated by a similar zinc-sensitive pathway. We noticed that total protein levels of some downregulated proteins at synaptosomal fraction were increased in Cttnbp2−/− mouse brains, which may be a consequence of a compensatory effect, reinforcing the defects of synaptic targeting caused by Cttnbp2 knockout. The second mechanism is an unknown regulatory pathway independent of CTTNBP2 association, exemplified by DPYSL3. Although synaptic levels of DPYSL3 were also reduced upon Cttnbp2 knockout, DPYSL3 was not associated with CTTNBP2 in our co-immunoprecipitation experiment and zinc supplementation did not increase (but actually decreased) DPYSL3 levels in synaptosomal fractions. Thus, the effect of Cttnbp2 knockout on DPYSL3 is distinct from its impact on SHANKs, STN and RAC3. Moreover, around half of the differentially expressed proteins, including some ribosomal and mitochondrial proteins, were upregulated, but it is unclear why. These proteins may be involved in metabolic processes that compensate for the deficits of neuronal activity.

Both environmental and genetic factors are involved in ASD [23, 42]. In this report, we show that Cttnbp2 deficiency reduces synaptic expression of SHANKs, NMDAR and downstream signaling molecules, including RAS and STRN (PP2A regulatory subunit). Zinc supplementation that increases synaptic expression and activity of SHANKs and NMDAR [25-30]effectively improved the social defects exhibited by our Cttnbp2-deficient mice. This scenario represents an example of how nutrition crosstalks with genetic variation. Our mice are fed with regular chaw from LabDiet (5K54), which is a complete life-cycle diet and also used by Jackson Laboratory. The concentration of zinc in Labdiet 5K54 is 84 ppm, which is already higher than the requirement of 30 ppm for pregnant mice (https://www.ncbi.nlm-.nih.gov/books/NBK231918/). However, since we show that synaptic targeting deficits of SHANKs and NMDAR were improved by adding extra zinc to drinking water, our findings imply that the genetic deficits that cause ASD may be ameliorated by nutritional supplementation. In our experiments, we provided an additional 40 ppm of zinc in drinking water. Consequently, daily zinc uptake reached a level similar to that of mice fed with chaw containing zinc at −150 ppm, which is still a reasonable concentration for mice [30]. This level of zinc supplementation improved the social behaviors of Cttnbp2-deficient mice, reinforcing the critical role of the NMDAR-SHANK pathway in neuronal defects caused by Cttnbp2 deficiency. Note that SLC30A9, an abundant zinc transporter (ZnT9) in brain, was upregulated in Cttnbp2−/− mice, likely to compensate the defects related to zinc homeostasis. Upregulation of Slc30a9 expression also provides a possibility to effectively transport zinc to the brains. It explains how zinc supplement can be effectively transported to Cttnbp2−/− brain to ameliorate defects there. Independently of zinc supplementation, D-cycloserine also ameliorates the behavioral defects of Cttnbp2-deficient mice, further supporting the notion that the NMDAR pathway is a crucial downstream effector of CTTNBP2 in controlling mouse social behaviors.

Based on our zinc supplementation experiments, we also suggest that caution has to be exercised in the nutritional constitution of mouse chaw. We have observed that regular mouse chaw from a diversity of suppliers exhibits broad zinc concentrations, such as 30 ppm (Research Diet), 36.8 ppm (F1515, Bio Serv), 60 ppm (Meat Free Rat and Mouse Diet, Specialty Feeds), 70 ppm (2018SX, Envigo), 84 ppm (5k54 and 5K52, LabDiet), and 130 ppm (5010, LabDiet). Since the social behaviors of Cttnbp2-deficient mice are sensitive to zinc supplementation, it is very possible that our mutant mice may exhibit subtly different phenotypes when fed with different diets. Nutrition is obviously a very important environmental factor influencing the behaviors of mice grown in different facilities.

Sequence Information

```
Amino acid sequence of human CTTNBP2 long form (the point
mutation is indicated in bold text with square frame)
                                                (SEQ ID NO: 1)
MATDGASCEPDLSRAPEDAAGAAAEAAKKEFDVDTLSKSEL[R]MLLSVMEGELEARDL

VIEALRARRKEVFIQERYGRFNLNDPFLALQRDYEAGAGDKEKKPVCTNPLSILE[A]V
```

-continued

MAHCKKMQERMSAQLAAAESRQKKLEMEKLQLQALEQEHKKLAARLEEERGKNKQVV
LMLVKECKQLSGKVIEEAQKLEDVMAKLEEEKKKTNELEEELSAEKRRSTEMEAQME
KQLSEFDTEREQLRAKLNREEAHTTDLKEEIDKMRKMIEQLKRGSDSKPSLSLPRKT
KDRRLVSISVGTEGTVTRSVACQTDLVTENADHMKKLPLTMPVKPSTGSPLVSANAK
GSVCTSATMARPGIDRQASYGDLIGASVPAFPPPSANKIEENGPSTGSTPDPTSSTP
PLPSNAAPPTAQTPGIAPQNSQAPPMHSLHSPCANTSLHPGLNPRIQAARFRFQGNA
NDPDQNGNTTQSPPSRDVSPTSRDNLVAKQLARNTVTQALSRFTSPQAGAPSRPGVP
PTGDVGTHPPVGRTSLKTHGVARVDRGNPPPIPPKKPGLSQTPSPPHPQLKVIIDSS
RASNTGAKVDNKTVASTPSSLPQGNRVINEENLPKSSSPQLPPKPSIDLTVAPAGCA
VSALATSQVGAWPAATPGLNQPACSDSSLVIPTTIAFCSSINPVSASSCRPGASDSL
LVTASGWSPSLTPLLMSGGPAPLAGRPTLLQQAAAQGNVILLSMLLNEEGLDINYSC
EDGHSALYSAAKNGHTDCVRLLLSAEAQVNAADKNGFTPLCAAAAQGHFECVELLIS
YDANINHAADGGQTPLYLACKNGNKECIKLLLEAGTNRSVKTTDGWTPVHAAVDTGN
VDSLKLLMYHRIPAHGNSFNEEESESSVFDLDGGEESPEGISKPVVPADLINHANRE
GWTAAHIAASKGFKNCLEILCRHGGLEPERRDKCNRTVHDVATDDCKHLLENLNALK
IPLRISVGEIEPSNYGSDDLECENTICALNIRKQTSWDDFSKAVSQALTNHFQAISS
DGWWSLEDVICNNTTDSNIGLSARSIRSITLGNVPWSVGQSFAQSPWDFMRKNKAEH
ITVLLSGPQEGCLSSVTYASMIPLQMMQNYLRLVEQYHNVIFHGPEGSLQDYIVHQL
ALCLKHRQMAAGFSCEIVRAEVDAGFSKEQLLDLFISSACLIPVKQSPSKKKIIIIL
ENLEKSSLSELLRDFLAPLENRSTESPCTFQKGNGLSECYYFHENCFLMGTIAKACL
QGSDLLVQQHFRWVQLRWDGEPMQGLLQRFLRRKVVNKFKGQAPSPCDPVCKIVDWA
LSVWRQLNSCLARLGTPEALLGPKYFLSCPVVPGHAQVTVKWMSKLWNGVIAPRVQE
AILSRASVKRQPGFGQTTAKRHPSQGQQAVVKAALSILLNKAVLHGCPLPRAELDQH
TADFKGGSFPLSIVSSYNTCNKKKGESGAWRKVNTSPRRKSGRFSLPTWNKPDLSTE
GMKNKTISQLNCNRNASLSKQKSLENDLSLTLNLDQRLSLGSDDEADLVKELQSMCS
SKSESDISKIADSRDDLRMFDSSGNNPVLSATINNLRMPVSQKEVSPLSSHQTTECS
NSKSKTELGVSRVKSFLPVPRSKVTQCSQNTKRSSSSSNTRQIEINNNSKEVNWNLH
KNEHLEKPNK

Amino acid sequence of human NF1
(SEQ ID NO: 2)
MAAHRPVEWVQAVVSRFDEQLPIKTGQQNTHTKVSTEHNKECLINISKYKFSLVISG
LTTILKNVNNMRIFGEAAEKNLYLSQLIILDTLEKCLAGQPKDTMRLDETMLVKQLL
PEICHFLHTCREGNQHAAELRNSASGVLFSLSCNNFNAVFSRISTRLQELTVCSEDN
VDVHDIELLQYINVDCAKLKRLLKETAFKFKALKKVAQLAVINSLEKAFWNWVENYP
DEFTKLYQIPQTDMAECAEKLFDLVDGFAESTKRKAAVWPLQIILLILCPEIIQDIS
KDVVDENNMNKKLFLDSLRKALAGHGGSRQLTESAAIACVKLCKASTYINWEDNSVI
FLLVQSMVVDLKNLLFNPSKPFSRGSQPADVDLMIDCLVSCFRISPHNNQHFKICLA
QNSPSTFHYVLVNSLHRIITNSALDWWPKIDAVYCHSVELRNMFGETLHKAVQGCGA
HPAIRMAPSLIFKEKVISLKFKEKPIDLETRSYKYLLLSMVKLIHADPKLLLCNPRK
QGPETQGSTAELITGLVQLVPQSHMPEIAQEAMEALLVLHQLDSIDLWNPDAPVETF -continued

WEISSQMLFYICKKLTSHQMLSSTEILKWLREILICRNKFLLKNKQADRSSCHFLLF

YGVGCDIPSSGNTSQMSMDHEELLRTPGASLRKGKGNSSMDSAAGCSGTPPICRQAQ

TKLEVALYMFLWNPDTEAVLVAMSCFRHLCEEADIRCGVDEVSVHNLLPNYNTFMEF

ASVSNMMSTGRAALQKRVMALLRRIEHPTAGNTEAWEDTHAKWEQATKLILNYPKAK

MEDGQAAESLHKTIVKRRMSHVSGGGSIDLSDTDSLQEWINMTGFLCALGGVCLQQR

SNSGLATYSPPMGPVSERKGSMISVMSSEGNADTPVSKFMDRLLSLMVCNHEKVGLQ

IRTNVKDLVGLELSPALYPMLFNKLKNTISKFFDSQGQVLLTDTNTQFVEQTIAIMK

NLLDNHTEGSSEHLGQASIETMMLNLVRYVRVLGNMVHAIQIKTKLCQLVEVMMARR

DDLSFCQEMKFRNKMVEYLTDWVMGTSNQAADDDVKCLTRDLDQASMEAVVSLLAGL

PLQPEEGDGVELMEAKSQLFLKYFTLFMNLLNDCSEVEDESAQTGGRKRGMSRRLAS

LRHCTVLAMSNLLNANVDSGLMHSIGLGYHKDLQTRATFMEVLTKILQQGTEFDTLA

ETVLADRFERLVELVTMMGDQGELPIAMALANVVPCSQWDELARVLVTLFDSRHLLY

QLLWNMFSKEVELADSMQTLFRGNSLASKIMTFCFKVYGATYLQKLLDPLLRIVITS

SDWQHVSFEVDPTRLEPSESLEENQRNLLQMTEKFFHAIISSSSEFPPQLRSVCHCL

YQATCHSLLNKATVKEKKENKKSVVSQRFPQNSIGAVGSAMFLRFINPAIVSPYEAG

ILDKKPPPRIERGLKLMSKILQSIANHVLFTKEEHMRPFNDFVKSNFDAARRFFLDI

ASDCPTSDAVNHSLSFISDGNVLAHRLLWNNQEKIGQYLSSNRDHKAVGRRPFDKM

ATLLAYLGPPEHKPVADTHWSSLNLTSSKFEEFMTRHQVHEKEEFKALKTLSIFYQA

GTSKAGNPIFYYVARRFKTGQINGDLLIYHVLLTLKPYYAKPYEIVVDLTHTGPSNR

FKTDFLSKWFVVFPGFAYDNVSAVYIYNCNSWVREYTKYHERLLTGLKGSKRLVFID

CPGKLAEHIEHEQQKLPAATLALEEDLKVFHNALKLAHKDTKVSIKVGSTAVQVTSA

ERTKVLGQSVFLNDIYYASEIEEICLVDENQFTLTIANQGTPLTFMHQECEAIVQSI

IHIRTRWELSQPDSIPQHTKIRPKDVPGTLLNIALLNLGSSDPSLRSAAYNLLCALT

CTFNLKIEGQLLETSGLCIPANNTLFIVSISKTLAANEPHLTLEFLEECISGFSKSS

IELKHLCLEYMTPWLSNLVRFCKHNDDAKRQRVTAILDKLITMTINEKQMYPSIQAK

IWGSLGQITDLLDVVLDSFIKTSATGGLGSIKAEVMADTAVALASGNVKLVSSKVIG

RMCKIIDKTCLSPTPTLEQHLMWDDIAILARYMLMLSFNNSLDVAAHLPYLFHVVTF

LVATGPLSLRASTHGLVINIIHSLCTCSQLHFSEETKQVLRLSLTEFSLPKFYLLFG

ISKVKSAAVIAFRSSYRDRSFSPGSYERETFALTSLETVTEALLEIMEACMRDIPTC

KWLDQWTELAQRFAFQYNPSLQPRALVVFGCISKRVSHGQIKQIIRILSKALESCLK

GPDTYNSQVLIEATVIALTKLQPLLNKDSPLHKALFWVAVAVLQLDEVNLYSAGTAL

LEQNLHTLDSLRIFNDKSPEEVFMAIRNPLEWHCKQMDHFVGLNFNSNFNFALVGHL

LKGYRHPSPAIVARTVRILHTLLTLVNKHRNCDKFEVNTQSVAYLAALLTVSEEVRS

RCSLKHRKSLLLTDISMENVPMDTYPIHHGDPSYRTLKETQPWSSPKGSEGYLAATY

PTVGQTSPRARKSMSLDMGQPSQANTKKLLGTRKSFDHLISDTKAPKRQEMESGITT

PPKMRRVAETDYEMETQRISSSQQHPHLRKVSVSESNVLLDEEVLTDPKIQALLLTV

LATLVKYTTDEFDQRILYEYLAEASVVFPKVFPVVHNLLDSKINTLLSLCQDPNLLN

PIHGIVQSVVYHEESPPQYQTSYLQSFGFNGLWRFAGPFSKQTQIPDYAELIVKFLD

ALIDTYLPGIDEETSEESLLTPTSPYPPALQSQLSITANLNLSNSMTSLATSQHSPG

IDKENVELSPTTGHCNSGRTRHGSASQVQKQRSAGSFKRNSIKKIV

-continued

Amino acid sequence of human TBR1
(SEQ ID NO: 3)
MQLEHCLSPSIMLSKKFLNVSSSYPHSGGSELVLHDHPIISTTDNLERSSPLKKITR

GMTNQSDTDNFPDSKDSPGDVQRSKLSPVLDGVSELRHSFDGSAADRYLLSQSSQPQ

SAATAPSAMFPYPGQHGPAHPAFSIGSPSRYMAHHPVITNGAYNSLLSNSSPQGYPT

AGYPYPQQYGHSYQGAPFYQFSSTQPGLVPGKAQVYLCNRPLWLKFHRHQTEMIITK

QGRRMFPFLSFNISGLDPTAHYNIFVDVILADPNHWRFQGGKWVPCGKADTNVQGNR

VYMHPDSPNTGAHWMRQEISFGKLKLTNNKGASNNNGQMVVLQSLHKYQPRLHVVEV

NEDGTEDTSQPGRVQTFTFPETQFIAVTAYQNTDITQLKIDHNPFAKGFRDNYDTTY

TGCDMDRLTPSPNDSPRSQIVPGARYAMAGSFLQDQFVSNYAKARFHPGAGAGPGPG

TDRSVPHTNGLLSPQQAEDPGAPSPQRWFVTPANNRLDFAASAYDTATDFAGNAATL

LSYAAAGVKALPLQAAGCTGRPLGYYADPSGWGARSPPQYCGTKSGSVLPCWPNSAA

AAARMAGANPYLGEEAEGLAAERSPLPPGAAEDAKPKDLSDSSWIETPSSIKSIDSS

DSGIYEQAKRRISPADTPVSESSSPLKSEVLAQRDCEKNCAKDISGYYGFYSHS

Amino acid sequence of mouse CTTNBP2 short form (the point
mutation is indicated in bold text with square frame)
(SEQ ID NO: 4)
MATDSASCEPDLSRTPGDTEGATAEAAKKEFDVDTLSKSELRMLLSVMEGELEARDL

VIEALRARRKEVFIQERYGRFNLNDPFLALQRDYEAGPGDKEKPVCTNPLSILEAVM

AHCRKMQERMSAQLVAAESRQKKLEMEKLQLQALEQEHKKLAAHLEEERGKNKHVVL

MLVKECKQLSGKVVEEAQKLEEVMAQLEEEKKKTSELEEQLSAEKQRSSGMEAQLEK

QLSEFDTEREQLRAKLSREEAHTTDLKEEIDKMKKMMEQMKKGSDGKPGLSLPRKTK

DKRLASISVATEGPVTRSVACQTDVVTESTDPVKKLPLTVPIKPSTGSPLVPTNTKG

NVGPSALLIRPGIDRQSSHSDLGPSPPTALPSSANRIEENGPSTGNAPDLSNSTPST

PSSTAPAAAQTPGTAPQNHSQAPTVHSLHSPCANTHPGLNPRIQAARFRFQGNANDP

DQNGNNTQSPPSRDVSPTSRDNLVAKQLARNTVTQALSRFTSPQAGASSRLGVSPGG

DAGTCPPVGRTGLKTPGAARVDRGNPPPIPPKKPGLSQTPSPPHPQLRASNAGAKVL

NKIVASPPSTLPQGTKVVNEENVPKSSSPQLPPKPSIDLTVAPAGCPVSALATSQAG

HPP

Amino acid sequence of mouse CTTNBP2 M120I mutant
(SEQ ID NO: 5)
MATDSASCEPDLSRTPGDTEGATAEAAKKEFDVDTLSKSELRMLLSVMEGELEARDL

VIEALRARRKEVFIQERYGRFNLNDPFLALQRDYEAGPGDKEKPVCTNPLSILEAVM

AHCRKIQERMSAQLVAAESRQKKLEMEKLQLQALEQEHKKLAAHLEEERGKNKHVVL

MLVKECKQLSGKVVEEAQKLEEVMAQLEEEKKKTSELEEQLSAEKQRSSGMEAQLEK

QLSEFDTEREQLRAKLSREEAHTTDLKEEIDKMKKMMEQMKKGSDGKPGLSLPRKTK

DKRLASISVATEGPVTRSVACQTDVVTESTDPVKKLPLTVPIKPSTGSPLVPTNTKG

NVGPSALLIRPGIDRQSSHSDLGPSPPTALPSSANRIEENGPSTGNAPDLSNSTPST

PSSTAPAAAQTPGTAPQNHSQAPTVHSLHSPCANTHPGLNPRIQAARFRFQGNANDP

```
DQNGNNTQSPPSRDVSPTSRDNLVAKQLARNTVTQALSRFTSPQAGASSRLGVSPGG

DAGTCPPVGRTGLKTPGAARVDRGNPPPIPPKKPGLSQTPSPPHPQLRASNAGAKVD

NKIVASPPSTLPQGTKVVNEENVPKSSSPQLPPKPSIDLTVAPAGCPVSALATSQAG

HPP

Amino acid sequence of mouse CTTNBP2 R533* mutant
                                                (SEQ ID NO: 6)
MATDSASCEPDLSRTPGDTEGATAEAAKKEFDVDTLSKSELRMLLSVMEGELEARDL

VIEALRARRKEVFIQERYGRFNLNDPFLALQRDYEAGPGDKEKPVCTNPLSILEAVM

AHCRKMQERMSAQLVAAESRQKKLEMEKLQLQALEQEHKKLAAHLEEERGKNKHVVL

MLVKECKQLSGKVVEEAQKLEEVMAQLEEEKKKTSELEEQLSAEKQRSSGMEAQLEK

QLSEFDTEREQLRAKLSREEAHTTDLKEEIDKMKKMMEQMKKGSDGKPGLSLPRKTK

DKRLASISVATEGPVTRSVACQTDVVTESTDPVKKLPLTVPIKPSTGSPLVPTNTKG

NVGPSALLIRPGIDRQSSHSDLGPSPPTALPSSANRIEENGPSTGNAPDLSNSTPST

PSSTAPAAAQTPGTAPQNHSQAPTVHSLHSPCANTHPGLNPRIQAARFRFQGNANDP

DQNGNNTQSPPSRDVSPTSRDNLVAKQLARNTVTQALSRFTSPQAGASSRLGVSPGG

DAGTCPPVGRTGLKTPGAA
```

REFERENCES

1. Lord C, Elsabbagh M, Baird G, Veenstra-Vanderweele J. Autism spectrum disorder. Lancet. 2018; 392(10146): 508-20. Epub 2018/08/07. doi: 10.1016/s0140-6736(18) 31129-2.
2. Sandin S, Lichtenstein P, Kuja-Halkola R, Hultman C, Larsson H, Reichenberg A. The Heritability of Autism Spectrum Disorder. Jama. 2017; 318(12):1182-4. Epub 2017/10/04. doi: 10.1001/jama.2017.12141. PubMed PMID: 28973605; PubMed Central PMCID: PMCPMC5818813.
3. Iossifov I, Ronemus M, Levy D, Wang Z, Hakker I, Rosenbaum J, et al. De novo gene disruptions in children on the autistic spectrum. Neuron. 2012; 74(2):285-99. Epub 2012/05/01. doi: S0896-6273(12)00340-6 [pii] 10.1016/j.neuron.2012.04.009 [doi]. PubMed PMID: 22542183.
4. De Rubeis S, He X, Goldberg A P, Poultney C S, Samocha K, Cicek A E, et al. Synaptic, transcriptional and chromatin genes disrupted in autism. Nature. 2014; 515 (7526):209-15. Epub 2014/11/05. doi: 10.1038/nature13772.
5. Sanders S J, He X, Willsey A J, Ercan-Sencicek A G, Samocha K E, Cicek A E, et al. Insights into Autism Spectrum Disorder Genomic Architecture and Biology from 71 Risk Loci. Neuron. 2015; 87(6):1215-33. Epub 2015/09/25. doi: 10.1016/j.neuron.2015.09.016. PubMed PMID: 26402605; PubMed Central PMCID: PMCPMC4624267.
6. Hering H, Sheng M. Activity-dependent redistribution and essential role of cortactin in dendritic spine morphogenesis. J Neurosci. 2003; 23(37):11759-69. PubMed PMID: 14684878.
7. Ohoka Y, Takai Y. Isolation and characterization of cortactin isoforms and a novel cortactin-binding protein, CBP90. Genes Cells. 1998; 3(9):603-12. PubMed PMID: 9813110.
8. Cheung J, Petek E, Nakabayashi K, Tsui L C, Vincent J B, Scherer S W. Identification of the human cortactin-binding protein-2 gene from the autism candidate region at 7q31. Genomics. 2001; 78(1-2):7-11. Epub 2001/11/15. doi: 10.1006/geno.2001.6651 [doi]S0888-7543(01) 96651-0 [pii]. PubMed PMID: 11707066.
9. Chen Y K, Hsueh Y P. Cortactin-binding protein 2 modulates the mobility of cortactin and regulates dendritic spine formation and maintenance. J Neurosci. 2012; 32(3):1043-55. Epub 2012/01/21. doi: 32/3/1043 [pii] 10.1523/JNEUROSCI.4405-11.2012 [doi]. PubMed PMID: 22262902.
10. Chen Y K, Chen C Y, Hu H T, Hsueh Y P. CTTNBP2, but not CTNBP2NL, regulates dendritic spinogenesis and synaptic distribution of the striatin-PP2A complex. Molecular Biology of Cell. 2012; 23:4383-92.
11. Li J, Zhang W, Yang H, Howrigan D P, Wilkinson B, Souaiaia T, et al. Spatiotemporal profile of postsynaptic interactomes integrates components of complex brain disorders. Nat Neurosci. 2017; 20(8):1150-61. Epub 2017/07/04. doi: 10.1038/nn.4594. PubMed PMID: 28671696; PubMed Central PMCID: PMCPMC5645082.
12. Shih P Y, Lee S P, Chen Y K, Hsueh Y P. Cortactin-binding protein 2 increases microtubule stability and regulates dendritic arborization. J Cell Sci. 2014; 127(Pt 16):3521-34. Epub 2014/06/15. doi: 10.1242/jcs.149476. PubMed PMID: 24928895.
13. Chen S, Chen J, Shi H, Wei M, Castaneda-Castellanos D R, Bultje R S, et al. Regulation of microtubule stability and organization by mammalian Par3 in specifying neuronal polarity. Dev Cell. 2013; 24(1):26-40. Epub 2013/ 01/01. doi: 10.1016/j.devcel.2012.11.014. PubMed Central PMCID: PMC3549028.
14. Naisbitt S, Kim E, Tu J C, Xiao B, Sala C, Valtschanoff J, et al. Shank, a novel family of postsynaptic density proteins that binds to the NMDA receptor/PSD-95/GKAP complex and cortactin. Neuron. 1999; 23(3):569-82.
15. Tu J C, Xiao B, Naisbitt S, Yuan J P, Petralia R S, Brakeman P, et al. Coupling of mGluR/Homer and PSD-95 complexes by the Shank family of postsynaptic density proteins. Neuron. 1999; 23(3):583-92. Epub 1999/08/05. doi: S0896-6273(00)80810-7 [pii]. PubMed PMID: 10433269.

16. Sheng M, Kim E. The Shank family of scaffold proteins. J Cell Sci. 2000; 113 (Pt 11):1851-6. Epub 2000/05/12.
17. Zimmer E R, Leuzy A, Souza D O, Portela L V. Inhibition of Protein Phosphatase 2A: Focus on the Glutamatergic System. Mol Neurobiol. 2016; 53(6):3753-5. Epub 2015/07/05. doi: 10.1007/s12035-015-9321-0.
18. Tu S, Okamoto S, Lipton S A, Xu H. Oligomeric Abeta-induced synaptic dysfunction in Alzheimer's disease. Molecular neurodegeneration. 2014; 9:48. Epub 2014/11/15. doi: 10.1186/1750-1326-9-48. PubMed Central PMCID: PMCPMC4237769.
19. Yasuda H, Yoshida K, Yasuda Y, Tsutsui T. Infantile zinc deficiency: association with autism spectrum disorders. Scientific reports. 2011; 1:129. Epub 2012/02/23. doi: 10.1038/srep00129. PubMed PMID: 28345660; PubMed Central PMCID: PMCPMC3216610.
20. Lee E J, Choi S Y, Kim E. NMDA receptor dysfunction in autism spectrum disorders. Current opinion in pharmacology. 2015; 20:8-13. Epub 2015/01/31. doi: 10.1016/j.coph.2014.10.007.
21. Pfaender S, Sauer A K, Hagmeyer S, Mangus K, Linta L, Liebau S, et al. Zinc deficiency and low enterocyte zinc transporter expression in human patients with autism related mutations in SHANK3. Scientific reports. 2017; 7:45190. Epub 2017/03/28. doi: 10.1038/srep45190. PubMed Central PMCID: PMCPMC5366950.
22. Curtin P, Austin C, Curtin A, Gennings C, Arora M, Tammimies K, et al. Dynamical features in fetal and postnatal zinc-copper metabolic cycles predict the emergence of autism spectrum disorder. Science advances. 2018; 4(5):eaat1293. Epub 2018/06/02. doi: 10.1126/sciadv.aat1293. PubMed Central PMCID: PMCPMC5976276.
23. Bolte S, Girdler S, Marschik P B. The contribution of environmental exposure to the etiology of autism spectrum disorder. Cell Mol Life Sci. 2019; 76(7):1275-97. Epub 2018/12/21. doi: 10.1007/s00018-018-2988-4. PubMed Central PMCID: PMCPMC6420889.
24. Jalali-Yazdi F, Chowdhury S, Yoshioka C, Gouaux E. Mechanisms for Zinc and Proton Inhibition of the GluN1/GluN2A NMDA Receptor. Cell. 2018; 175(6):1520-32.e15. Epub 2018/12/01. doi: 10.1016/j.cell.2018.10.043. PubMed Central PMCID: PMCPMC6333211.
25. Lee E J, Lee H, Huang T N, Chung C, Shin W, Kim K, et al. Trans-synaptic zinc mobilization improves social interaction in two mouse models of autism through NMDAR activation. Nature communications. 2015; 6:7168. Epub 2015/05/20. doi: 10.1038/ncomms8168. PubMed Central PMCID: PMC4479043.
26. Grabrucker A M, Knight M J, Proepper C, Bockmann J, Joubert M, Rowan M, et al. Concerted action of zinc and ProSAP/Shank in synaptogenesis and synapse maturation. Embo j. 2011; 30(3):569-81. Epub 2011/01/11. doi: 10.1038/emboj.2010.336. PubMed Central PMCID: PMCPMC3034012.
27. Grabrucker S, Jannetti L, Eckert M, Gaub S, Chhabra R, Pfaender S, et al. Zinc deficiency dysregulates the synaptic ProSAP/Shank scaffold and might contribute to autism spectrum disorders. Brain. 2014; 137(Pt 1):137-52. Epub 2013/11/28. doi: 10.1093/brain/awt303.
28. Grabrucker A M. A role for synaptic zinc in ProSAP/Shank PSD scaffold malformation in autism spectrum disorders. Developmental neurobiology. 2014; 74(2):136-46. Epub 2013/05/08. doi: 10.1002/dneu.22089. PubMed Central PMCID: PMCPMC4272576.
29. Hagmeyer S, Sauer A K, Grabrucker A M. Prospects of Zinc Supplementation in Autism Spectrum Disorders and Shankopathies Such as Phelan McDermid Syndrome. Frontiers in synaptic neuroscience. 2018; 10:11. Epub 2018/06/08. doi: 10.3389/fnsyn.2018.00011. PubMed Central PMCID: PMCPMC5974951.
30. Fourie C, Vyas Y, Lee K, Jung Y, Garner C C, Montgomery J M. Dietary Zinc Supplementation Prevents Autism Related Behaviors and Striatal Synaptic Dysfunction in Shank3 Exon 13-16 Mutant Mice. Front Cell Neurosci. 2018; 12:374. Epub 2018/11/09. doi: 10.3389/fncel.2018.00374. PubMed Central PMCID: PMCPMC6204368.
31. Stavridi E S, Harris K G, Huyen Y, Bothos J, Verwoerd P M, Stayrook S E, et al. Crystal structure of a human Mob protein: toward understanding Mob-regulated cell cycle pathways. Structure (London, England: 1993). 2003; 11(9):1163-70. Epub 2003/09/10.
32. Ponchon L, Dumas C, Kajava A V, Fesquet D, Padilla A. NMR solution structure of Mob1, a mitotic exit network protein and its interaction with an NDR kinase peptide. J Mol Biol. 2004; 337(1):167-82. Epub 2004/03/06. doi: 10.1016/j.jmb.2004.01.010. PubMed PMID: 15001360.
33. Hood W F, Compton R P, Monahan J B. D-cycloserine: a ligand for the N-methyl-D-aspartate coupled glycine receptor has partial agonist characteristics. Neurosci Lett. 1989; 98(1):91-5. Epub 1989/03/13.
34. Emmett M R, Mick S J, Cler J A, Rao T S, Iyengar S, Wood P L. Actions of D-cycloserine at the N-methyl-D-aspartate-associated glycine receptor site in vivo. Neuropharmacology. 1991; 30(11):1167-71. Epub 1991/11/01.
35. Won H, Lee H R, Gee H Y, Mah W, Kim J I, Lee J, et al. Autistic-like social behaviour in Shank2-mutant mice improved by restoring NMDA receptor function. Nature. 2012; 486(7402):261-5. Epub 2012/06/16. doi: nature11208 [pii]10.1038/nature11208 [doi]. PubMed PMID: 22699620.
36. Huang T N, Chuang H C, Chou W H, Chen C Y, Wang H F, Chou S J, et al. Tbr1 haploinsufficiency impairs amygdalar axonal projections and results in cognitive abnormality. Nat Neurosci. 2014; 17(2):240-7. Epub 2014/01/21. doi: 10.1038/nn.3626.
37. Lee E, Lee J, Kim E. Excitation/Inhibition Imbalance in Animal Models of Autism Spectrum Disorders. Biol Psychiatry. 2017; 81(10):838-47. Epub 2016/07/28. doi: 10.1016/j.biopsych.2016.05.011.
38. Huang T N, Yen T L, Qiu L R, Chuang H C, Lerch J P, Hsueh Y P. Haploinsufficiency of autism causative gene Tbr1 impairs olfactory discrimination and neuronal activation of the olfactory system in mice. Molecular autism. 2019; 10:5. Epub 2019/02/23. doi: 10.1186/s13229-019-0257-5. PubMed Central PMCID: PMCPMC6371489.
39. Montagrin A, Saiote C, Schiller D. The social hippocampus. Hippocampus. 2018; 28(9):672-9. Epub 2017/08/27. doi: 10.1002/hipo.22797.
40. Allsop S A, Vander Weele C M, Wichmann R, Tye K M. Optogenetic insights on the relationship between anxiety-related behaviors and social deficits. Front Behav Neurosci. 2014; 8:241. Epub 2014/08/01. doi: 10.3389/fnbeh.2014.00241. PubMed Central PMCID: PMCPMC4099964.
41. Okuyama T, Kitamura T, Roy D S, Itohara S, Tonegawa S. Ventral C A neurons store social memory. Science. 2016; 353(6307):1536-41. Epub 2016/10/07. doi: 10.1126/science.aaf7003. PubMed Central PMCID: PMCPMC5493325.

42. Quesnel-Vallieres M, Weatheritt R J, Cordes S P, Blencowe B J. Autism spectrum disorder: insights into convergent mechanisms from transcriptomics. Nature reviews Genetics. 2019; 20(1):51-63. Epub 2018/11/06. doi: 10.1038/s41576-018-0066-2.
43. Lin C W, Hsueh Y P. Sarm1, a neuronal inflammatory regulator, controls social interaction, associative memory and cognitive flexibility in mice. Brain Behav Immun. 2014; 37:142-51. doi: 10.1016/j.bbi.2013.12.002.
44. Chung W C, Huang T N, Hsueh Y P. Targeted Deletion of CASK-Interacting Nucleosome Assembly Protein Causes Higher Locomotor and Exploratory Activities. NeuroSignals. 2011; 19(3):128-41. Epub 2011/05/18. doi: 000327819 [pii]10.1159/000327819 [doi]. PubMed PMID: 21576927.
45. Hung Y F, Chen C Y, Shih Y C, Liu H Y, Huang C M, Hsueh Y P. Endosomal TLR3, TLR7, and TLR8 control neuronal morphology through different transcriptional programs. J Cell Biol. 2018; 217(8):2727-42. Epub 2018/05/20. doi: 10.1083/jcb.201712113. PubMed Central PMCID: PMCPMC6080926.
46. Brohee S, van Helden J. Evaluation of clustering algorithms for protein-protein interaction networks. BMC bioinformatics. 2006; 7:488. Epub 2006/11/08. doi: 10.1186/1471-2105-7-488. PubMed Central PMCID: PMCPMC1637120.
47. Nambot S, Faivre L, Mirzaa G et al., De novo TBR1 variants cause a neurocognitive phenotype with ID and autistic traits: report of 25 new individuals and review of the literature. Eur J Hum Genet. 2020; 28(6):770-782. Epub 2020/01/31. doi: 10.1038/s41431-020-0571-6. PMID: 32005960.
48. Hsueh Y P, Hsu T T, Huang T N. The evolutionarily conserved function of TBR1 in controlling the size of anterior commissure in human and mouse brains. Eur J Hum Genet. 2020; 28(8):997-998. Epub 2020/04/09. doi: 10.1038/s41431-020-0621-0. PMID:32273580.
49. Huang Y N, Chuang H C, Chou W H. Tbr1 haploinsufficiency impairs amygdalar axonal projections and results in cognitive abnormality. Nat Neurosci. 2014; 17(2):240-7. Epub 2014/01/19. doi: 10.1038/nn.3626. PMID: 24441682.
50. Huang Y N, Yen T L, Qiu L R. Haploinsufficiency of autism causative gene Tbr1 impairs olfactory discrimination and neuronal activation of the olfactory system in mice. Mol Autism. 2019; 11; 10:5. doi: 10.1186/s13229-019-0257-5. eCollection 2019. PMID: 30792833.
51. Lee H J, Lee H, Huang T N. Trans-synaptic zinc mobilization improves social interaction in two mouse models of autism through NMDAR activation. Nat Commun. 2015; 18; 6:7168. doi: 10.1038/ncomms8168. PMID: 25981743.
52. Bulfone A, Wang F, Hevner R. An olfactory sensory map develops in the absence of normal projection neurons or GABAergic interneurons. Neuron. 1998; 21(6):1273-82. doi: 10.1016/s0896-6273(00)80647-9. PMID: 9883721.

What is claimed is:

1. A method for treating a symptom or disease characteristics associated with autism spectrum disorder (ASD) or ASD-associated disorder in a subject in need thereof, comprising
administering to the subject a zinc ion source in an amount of about 0.10 mg to about 1.50 mg/kg body weight per day in combination with a serine component including L-serine or its precursor/analogue, and branched-chain amino acids (BCAAs).

2. The method of claim 1, wherein the subject suffers from ASD.

3. The method of claim 1, wherein the ASD-associated disorder is neurofibromatosis type 1 (NF1).

4. The method of claim 1, wherein the symptom or disease characteristics include impaired social interaction, hyperactivity and/or anxiolytic effect.

5. The method of claim 4, wherein the impaired social interaction includes deficits in social novelty preference (social memory) and/or reciprocal social interaction.

6. The method of claim 1, wherein the subject has a mutation in an endogenous gene encoding CTTNBP2 and/or TBR1 and/or neurofibromin resulting a defect in dendritic spine formation.

7. The method of claim 6, wherein the mutation in the endogenous gene encoding CTTNBP2 results in a modification at an amino acid position corresponding to amino acid position 42, 113, 121, G343, P354, R536 and/or 580 of the amino acid sequence set forth in SEQ ID NO: 1.

8. The method of claim 1, wherein the zinc ion source is administered in an amount of about 0.1 mg to about 1.2 mg/kg body weight per day.

9. The method of claim 1, wherein the serine component is administered in an amount resulting in an increased serine component level in the subject compared with a corresponding basal level for the subject.

10. The method of claim 1, wherein the BCAAs are administered in an amount resulting in an increased BCAAs level in the subject compared with a corresponding basal level for the subject.

11. The method of claim 1, wherein the zinc ion source is administered in amounts of about 0.2 mg to about 0.9 mg/kg body weight per day.

12. The method of claim 1, wherein the serine component and the BCAAs are administered in amounts with the zinc ion source to provide an improved effect in treating the symptom or disease characteristics associated with ASD or ASD-associated disorder, as compared with the zinc ion source, serine component and the BCAAs alone.

13. The method of claim 1, wherein the zinc ion source is administered in an amount of about 0.3 mg to about 0.7 mg/kg body weight per day.

14. The method of claim 1, further comprising measuring a basal serine component level of the subject before administration of the serine component, and then the serine component is administered in an amount sufficient to provide an increased serine component level in the subject compared with the basal serine component level.

15. The method of claim 1, further comprising measuring a basal BCAAs level of the subject before administration of the BCAAs, and then the BCAAs are administered in an amount sufficient to provide an increased BCAAs level in the subject compared with the basal BCAAs level.

16. The method of claim 1, wherein the BCAAs includes leucine, isoleucine and valine in a weight ratio of about 2:1:1.

17. The method of claim 1, wherein the the serine component is L-serine.

18. The method of claim 1, wherein the serine component is administered in an amount of about 0.01 g to about 0.50 g/kg body weight per day.

19. The method of claim 1, wherein the BCAAs are administered in an amount of about 0.01 g/kg to about 0.50 g/kg body weight per day.

20. The method of claim 1, wherein the zinc ion source, the serine component and the BCAAs are administered together in a composition or separately as a combination therapy.

21. The method of claim 1, wherein the zinc ion source, the serine component and the BCAAs are administered daily for a 1-10 day period, optionally at a proper time interval between each period.

* * * * *